(12) United States Patent
Anderson

(10) Patent No.: US 10,321,885 B2
(45) Date of Patent: Jun. 18, 2019

(54) VOXEL-RESOLUTION MYOCARDIAL BLOOD FLOW ANALYSIS

(71) Applicant: HOWARD UNIVERSITY, Washington, DC (US)

(72) Inventor: John M. M. Anderson, Washington, DC (US)

(73) Assignee: HOWARD UNIVERSITY, Washington, DC (US)

( * ) Notice: Subject to any disclaimer, the term of this patent is extended or adjusted under 35 U.S.C. 154(b) by 0 days.

(21) Appl. No.: 15/026,697

(22) PCT Filed: Oct. 3, 2014

(86) PCT No.: PCT/US2014/059062
§ 371 (c)(1),
(2) Date: Apr. 1, 2016

(87) PCT Pub. No.: WO2015/051256
PCT Pub. Date: Apr. 9, 2015

(65) Prior Publication Data
US 2016/0242718 A1    Aug. 25, 2016

Related U.S. Application Data

(63) Continuation-in-part of application No. 14/008,021, filed as application No. PCT/US2012/031263 on Mar. 29, 2012, now Pat. No. 9,149,244.
(Continued)

(51) Int. Cl.
*A61B 5/00* (2006.01)
*A61B 6/00* (2006.01)
(Continued)

(52) U.S. Cl.
CPC ............ *A61B 6/507* (2013.01); *A61B 5/0044* (2013.01); *A61B 5/02755* (2013.01);
(Continued)

(58) Field of Classification Search
CPC ... A61B 5/0044; A61B 5/02755; A61B 6/037; A61B 6/507; G16H 50/50; G06F 19/00;
(Continued)

(56) References Cited

U.S. PATENT DOCUMENTS

| 5,070,877 A | 12/1991 | Mohiuddin et al. |
| 5,135,000 A | 8/1992 | Akselrod et al. |

(Continued)

FOREIGN PATENT DOCUMENTS

| WO | 2012135526 | 10/2012 |
| WO | 2014130566 | 8/2014 |

OTHER PUBLICATIONS

Schwaiger et al. "Assessment of Myocardial Perfusion with 13N-Ammonia or 82RB." Cardiac Positron Emission Tomography. Springer US, 1996. 121-146.*

(Continued)

*Primary Examiner* — Katrina R Fujita
(74) *Attorney, Agent, or Firm* — Fitch, Even, Tabin & Flannery, LLP

(57) ABSTRACT

A myocardial blood flow analysis scan includes incorporating a pharmacological kinetic model with the standard factor analysis model where each time activity curve is assumed to be a linear combination of factor curves. Pharmacological kinetics based factor analysis of dynamic structures (K-FADS-II) model can be applied, whereby estimating factor curves in the myocardium can be physiologically meaningful is provided. Additional optional aspects include performing a discretization to transform continuous-time K-FADS-II model into a discrete-time K-FADS-II model and application of an iterative Improved Voxel-Resolution myocardial blood flow (IV-MBF) algorithm. Where the model is applied without assumption that a right ventricle tissue curve and a left ventricle tissue curve obey a particular (Continued)

mathematical relationship, a least squares objective function can be applied to obtain estimates for parameters of the pharmacological kinetic model by applying a majorize-minimize optimization technique to iteratively estimate the curves.

20 Claims, 5 Drawing Sheets

Related U.S. Application Data

(60) Provisional application No. 61/468,765, filed on Mar. 29, 2011, provisional application No. 61/887,290, filed on Oct. 4, 2013.

(51) Int. Cl.
   A61B 6/03        (2006.01)
   G06T 7/00        (2017.01)
   G16H 50/50       (2018.01)
   A61B 5/0275      (2006.01)
   G06F 19/00       (2018.01)

(52) U.S. Cl.
   CPC .............. *A61B 6/037* (2013.01); *G06F 19/00* (2013.01); *G06T 7/0016* (2013.01); *G16H 50/50* (2018.01); *G06T 2207/10104* (2013.01); *G06T 2207/30104* (2013.01)

(58) Field of Classification Search
   CPC ......... G06T 7/0016; G06T 2207/10104; G06T 2207/30104
   See application file for complete search history.

(56) References Cited

U.S. PATENT DOCUMENTS

| | | | |
|---|---|---|---|
| 5,732,707 A | 3/1998 | Widder et al. | |
| 5,926,568 A | 7/1999 | Chaney | |
| 7,127,095 B2 | 10/2006 | El Fakhri et al. | |
| 7,251,306 B2 | 7/2007 | Sauer | |
| 7,295,154 B2 | 11/2007 | Walton | |
| 7,519,211 B2 | 4/2009 | El Fakhri et al. | |
| 7,804,440 B1 | 9/2010 | Orr | |
| 8,207,886 B2 | 6/2012 | Chambers | |
| 8,570,208 B2 | 10/2013 | Sarkis | |
| 9,208,557 B2* | 12/2015 | Pautot ............. | A61B 5/02028 |
| 2003/0048937 A1* | 3/2003 | Gullberg ............ | G06T 5/001 382/131 |
| 2006/0022866 A1 | 2/2006 | Walton et al. | |
| 2006/0083415 A1* | 4/2006 | El Fakhri ............ | G06T 7/0012 382/128 |
| 2006/0104410 A1 | 5/2006 | Sauer et al. | |
| 2006/0187305 A1 | 8/2006 | Trivedi | |
| 2008/0230703 A1 | 9/2008 | Kadrmas et al. | |
| 2009/0226064 A1* | 9/2009 | El Fakhri ............ | G06T 7/0012 382/128 |
| 2010/0060509 A1 | 3/2010 | Chambers et al. | |
| 2010/0312118 A1 | 12/2010 | Horzewski | |
| 2011/0128816 A1 | 6/2011 | Baba et al. | |
| 2011/0150309 A1 | 6/2011 | Barfett | |
| 2012/0019406 A1 | 1/2012 | Sarkis | |
| 2013/0004044 A1 | 1/2013 | Ross | |
| 2013/0024126 A1 | 1/2013 | Weibrecht | |
| 2014/0016850 A1 | 1/2014 | Anderson | |
| 2014/0236004 A1 | 8/2014 | Rognin | |
| 2015/0279082 A1 | 10/2015 | Anderson | |

OTHER PUBLICATIONS

Hu, Chuanpu, William S. Lovejoy, and Steven L. Shafer. "Comparison of some control strategies for three-compartment PK/PD models." Journal of Pharmacokinetics and Biopharmaceutics 22.6 (1994): 525-550. (Year: 1994).*

Riabkov, Dmitri Y., and Edward VR Di Bella. "Blind identification of the kinetic parameters in three-compartment models." Physics in Medicine & Biology 49.5 (2004): 639. (Year: 2004).*

Schelbert, Heinrich R. "Quantifying myocardial perfusion for the assessment of preclinical CAD." Cardiac PET and PET/CT Imaging. Springer, New York, NY, 2007. 160-176. (Year: 2007).*

Candes, E., et al.; "Enhancing Sparsity by Reweighted l1 Minimization"; Research paper; Oct. 2007; 28 pages.

Chen, S., et al.; "Atomic Decomposition by Basis Pursuit"; SIAM Journal on Scientific Computing; vol. 43, No. 1, pp. 129-159; 2001.

Davis, G., et al.; "Adaptive Greedy Approximations"; Constructive Approximation; vol. 13, No. 1; 1997; 47 pages.

De Leeuw, J., et al.; "Sharp Quadratic Majorization in One Dimension"; Computational Statistics and Data Analysis; vol. 53, No. 1; 2009; 14 pages.

De Pierro, A.; "A Modified Expectation Maximization Algorithm for Penalized Likelihood Estimation in Emission Tomography"; IEEE Transactions on Medical Imaging; vol. 14, No. 1, pp. 132-137; Mar. 1995.

European Patent Office Extended European Search Report dated Jul. 17, 2014 for European Application No. 12764542.2; 7 pages.

Figueiredo, M., et al.; "Wavelet-Based Image Estimation: An Empirical Bayes Approach Using Jeffrey's Noninformative Prior"; IEEE Transactions on Image Processing; vol. 10, No. 9, pp. 1322-1331; Sep. 2001.

Hove, J., et al.; "Dual Spillover Problem in the Myocardial Septum with Nitrogen-13-Ammonia Flow Quantitation"; The Journal of Nuclear Medicine; vol. 39, pp. 591-598; Apr. 1998.

Hunter, D., et al.; "A Tutorial on MM Algorithms"; The American Statistician; vol. 58, pp. 30-37; Feb. 2004.

Hutchins, G., et al.; "Noninvasive Quantification of Regional Blood Flow in the Human Heart Using N-13 Ammonia and Dynamic Positron Emission Tomographic Imaging"; JACC; vol. 15, No. 5, pp. 1032-1042; Apr. 1990.

Klein, R., et al.; "Kinetic model-based factor analysis of dynamic sequences for 82-rubidium cardiac positron emission tomograph"; Medical Physics; vol. 37, No. 8, pp. 3995-4010; Aug. 2010.

Metje, N., et al.; "Mapping the Underworld—State-of-the-art review"; Tunnelling and Underground Space Technology; vol. 22, pp. 568-586; 2007.

Nguyen, L., et al,; "Mine Field Detection Algorithm Utilizing Data From an Ultrawideband Wide-Area Surveillance Radar"; Proc. SPIE 3392, Detection and Remediation Technologies for Mines and Minelike Targets III; vol. 3392, pp. 627-643; Apr. 1998.

Nguyen, L., et al.; "Supperssion of Sidelobes and Noise in Airborner SAR Imagery Using the Recursive Sidelobe Minimization Technique"; U.S. Army Research Laboratory; IEEE Radar Conference; pp. 522-525; May 2010.

Nguyen, L., et al.; "Obstacle Avoidance and Concealed Target Detection Using the Army Research Lab Ultra-Wideband Synchronous Impulse Reconstruction (UWB SIRE) Forward Imaging Radar"; U.S. Army Research Laboratory; Proc of SPIE vol. 6553; 2007; 8 pages.

Nguyen, L., et al.; "Signal Processing Techniques for Forward Imaging Using Ultra-Wideband Synthetic Aperture Radar"; U.S. Army Research Laboratory; Proc of SPIE vol. 5083, pp. 505-518; 2003.

Nguyen, L.; "Image Resolution Computation for Ultra-Wideband (UWB) Synchronous Impulse Reconstruction (SIRE) Radar"; Army Research Laboratory; Sep. 2007; 26 pages.

Nguyen, L.; "Signal and Image Processing Algorithms for U.S. Army Research Laboratory Ultra-wideband (UWB) Synchronous Impulse Re-construction (SIRE) Radar"; Army Research Lab; pp. 35-38; Apr. 2009.

Nguyen, L.; "SAR Imaging Techniques for Reduction of Sidelobes and Noise"; Army Research Laboratory; Proc of SPIE vol. 7308; 2009; 12 pages.

Notification Concerning Transmittal of International Preliminary Report on Patentability from the International Bureau of WIPO for International Application No. PCT/US2012/031263 dated Oct. 10, 2013, 5 pages.

(56) References Cited

OTHER PUBLICATIONS

Notification of Transmittal of the International Search Report and the Written Opinion of the International Searching Authority, or the Declaration from the International Bureau of WIPO for International Application No. PCT/US2012/031263 dated Oct. 30, 2012; 8 pages.
Notification of Transmittal of the International Search Report and the Written Opinion of the International Searching Authority, or the Declaration from the International Bureau of WIPO for International Application No. PCT/US2014/017185 dated Jun. 10, 2014; 17 pages.
Potter, L., et al.; "Sparsity and Compressed Sensing in Radar Imaging"; Proceedings of the IEEE; vol. 98, No. 6, pp. 1006-1020; Jun. 2010.
Ressler, M., et al.; "The Army Research Laboratory (ARL) Synchronous Impulse Reconstruction (SIRE) Forward-Looking Radar"; Proc. of SPIE vol. 6561; 2007; 12 pages.
Schmidt, M.; "Least Squares Optimization with L1-Norm Regularization"; Project Report; Dec. 2005; 12 pages.
Tan, X., et al.; "Sparse Learning via Iterative Minimization With Application to MIMO Radar Imaging"; IEEE Transactions on Siginal Processing; vol. 59, No. 3, pp. 1088-1101; Feb. 2011.
Tibshirani, R.; "Regression Shrinkage and Selection via the Lasso"; Journal of Royal Statistical Society; Series B, vol. 58, No. 1, pp. 267-288; 1996.
Vaida, F.; "Parameter Convergence for EM and MM Algorithms"; Statistica Sinica; vol. 15, No. 3, pp. 831-840; 2005.
Van Der Merwe, A., et al.; "A Clutter Reduction Technique for GPR Data from Mine Like Targets"; Proc. SPIE vol. 3719; Aug. 1999; 12 pages.
Wu, C.; "On the Convergence Properties of the EM Algorithm"; The Annals of Statistics; vol. 11, No. 1, pp. 95-103; Mar. 1983.
Wu, T.T., et al.; "The MM Alternative to EM"; Statistical Science; vol. 25, No. 4, pp. 492-505; Apr. 2011.
Wu, Z., et al.; "An Image Reconstruction Method Using GPR Data"; IEEE Transactions on Geoscience and Remote Sensing; vol. 37, No. 1; Jan. 1999; 8 pages.
Yang, A., et al.; "Fast L1-Minimization Algorithms and an Application in Robust Face Recognition: A Review"; Technical Report No. UCB/EECS-2010-13; Feb. 2010; 14 pages.
Yang, A., et al.; "Fast l1-Minimization Algorithms for Robust Face Recognition"; IEEE Transactions on Image Processing; vol. 22, No. 8, pp. 3234-3246; Jun. 2013.
Notification of Transmittal of the International Search Report and the Written Opinion of the International Searching Authority, or the Declaration from the International Bureau of WIPO for International Application No. PCT/US2014/059062 dated Jan. 14, 2015; 11 pages.
Notification of Transmittal of the International Search Report and the Written Opinion of the International Searching Authority, or the Declaration from the International Bureau of WIPO for International Application No. PCT/US14/42562 dated Mar. 18, 2015; 10 pages.
Ndoyle, M., et al.; "An MM-based Algorithm for L1-Regularized Least Squares Estimation in GPR Image Reonstruction"; IEEE Radar Conference; pp. 1-6; May 2013.
Gogineni, Sandeep, and Arye Nehorai. "Target estimation using sparse modeling for distributed MIMO radar." IEEE Transactions on Signal Processing 59.11 (2011 ): 5315-5325.
El Fakhri, G. et al., "Reproducibility and Accuracy of Quantitative Myocardial Blood Flow Assessment with 82Rb PET: Comparison with 13N-Ammonia PET." The Journal of Nuclear Medicine, vol. 50, No. 7, Jul. 2009; pp. 1062-1071.
Office Action Communication pursuant to Article 94(3) dated Jan. 4, 2019; European Patent Application No. 14850179.4 ; 6 pages.

\* cited by examiner

FIG. 3A
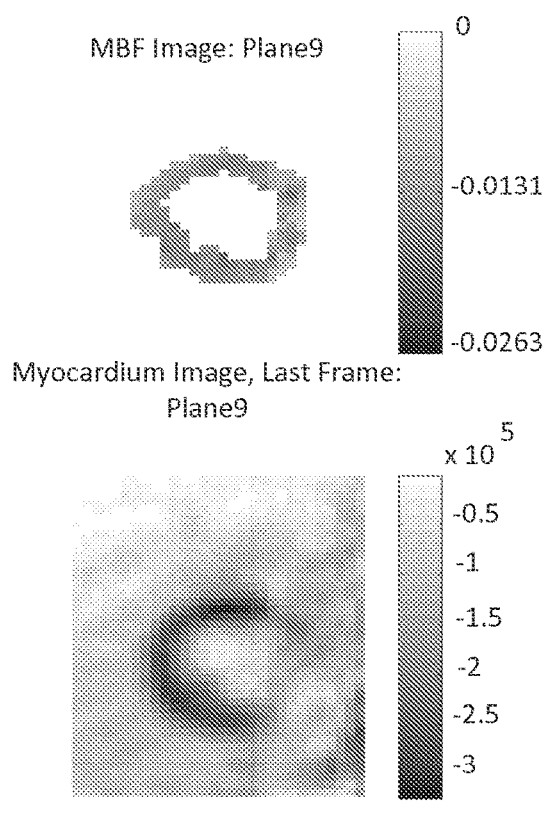
FIG. 3C
FIG. 3B
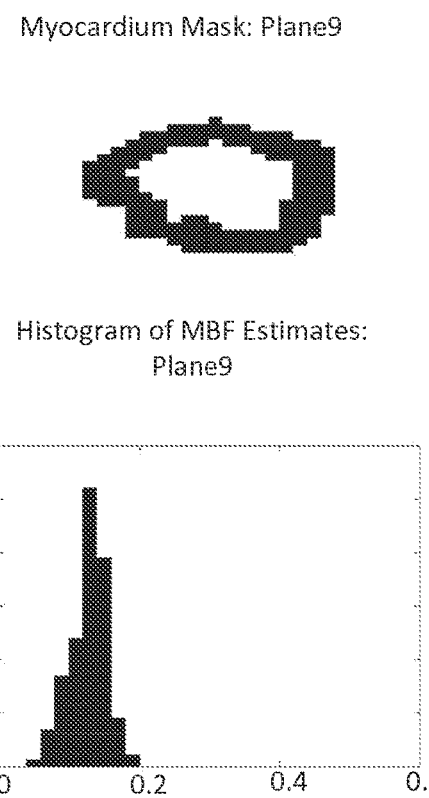
FIG. 3D

FIG. 4A
FIG. 4B
MBF Image:
Plane16
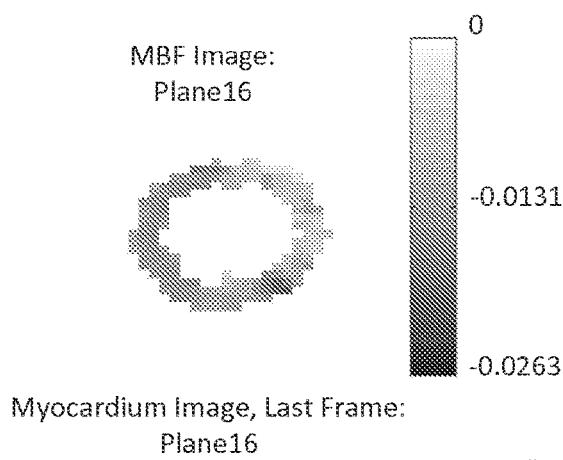
Myocardium Mask:
Plane16
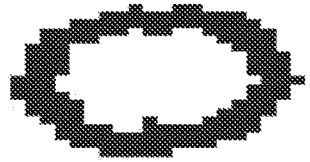
Myocardium Image, Last Frame:
Plane16
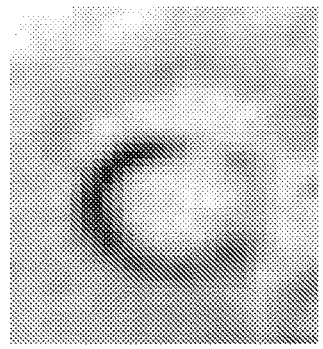
Histogram of MBF Estimates:
Plane16
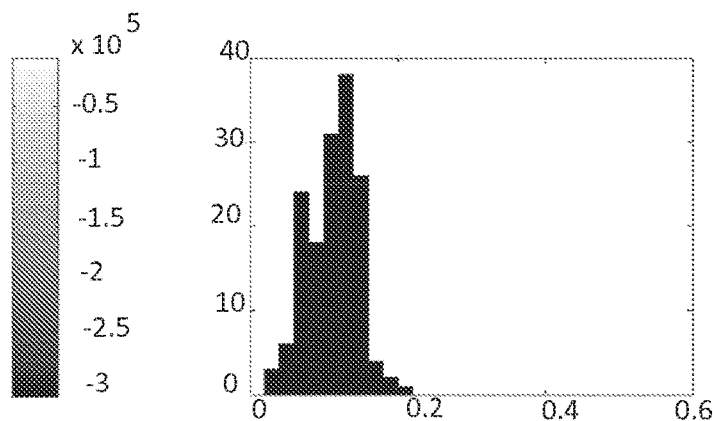
FIG. 4C
FIG. 4D

VOXEL-RESOLUTION MYOCARDIAL BLOOD FLOW ANALYSIS

RELATED APPLICATIONS

This application is a U.S. national phase application filed under 35 U.S.C. § 371 of International Application Number PCT/US2014/059062, filed Oct. 3, 2014, designating the United States, which is a continuation in part of U.S. application Ser. No. 14/008,021 filed Sep. 27, 2013, now U.S. Pat. No. 9,149,244, which is the National Stage of International Application No. PCT/US2012/031263, filed Mar. 29, 2012, which claims the benefit of U.S. Provisional application No. 61/468,765, filed Mar. 29, 2011, and this application also claims the benefit of U.S. Provisional application No. 61/887,290, filed Oct. 4, 2013, each of which is incorporated by reference in their entireties herein.

TECHNICAL FIELD

This invention relates generally to estimating myocardial blood flow (MBF) and more specifically to a positron emission tomography (PET) based method for estimating myocardial blood flow (MBF).

BACKGROUND

Imaging of blood flow through the heart and associated veins can improve diagnosis and treatment of cardiac diseases. In particular, estimation of myocardial blood flow or blood flow through heart muscular tissue can be useful as described below.

By one approach, nuclear based medicine can be used to produce useful medical images. In such an approach, radioactive elements are introduced into the bloodstream such that when the radioactive elements experience a radioactive decay, the byproducts of that decay (often the reaction with particles called positrons) can be sensed to produce an image of the area where the radioactive elements are placed. An example approach to this kind of imaging is called positron emission tomography (PET). Several radioactive elements, called positron emitting tracers, are available for these studies with the most common being $^{82}$Rb and $^{13}$N-Ammonia.

Currently, PET is a primary method for determining non invasive coronary flow reserve. Coronary flow reserve can be defined as a ratio of a maximum hyperemic flow to baseline flow. In normal patients this ratio can typically range between 3-5, which is a essentially a measure of the function of coronary circulation and is particularly useful in the detection of early abnormalities due to coronary artery disease. Because the coronary flow reserve determination is a ratio, it is unaffected by a uniform reduction in both baseline and maximal flow.

Unfortunately, coronary flow reserve does not reflect true vasodilation capacity. A reduction in coronary flow reserve could be caused either by increased flow in the baseline state or by reduced maximum hyperemic flow. Factors that increase myocardial oxygen demand, for example hypertension, increased left ventricular wall stress, increases in inotropic state, and tachycardia, can lead to an increased basal flow. Differentiating between this case and the reduced maximal hyperemic flow due to significant coronary stenosis is difficult without absolute myocardial blood flow measurements. Measurements of hyperemic blood flow in absolute units provide a more direct estimate of vasodilation capacity. Accordingly, only by accurate determination of absolute myocardial blood flow can the existence of uniform diffuse disease be determined.

Since the early 1990's there have been validated techniques for estimating absolute myocardial blood flow. Nevertheless, absolute myocardial flow estimation has not been adopted for routine use in a clinic setting because of technical limitations. These limitations can include lack of technical expertise in a clinical setting, time taken to perform the calculations, and the lack of widely available commercial products to perform the calculations and display the results. On the other hand, numerous reports indicate the effect on absolute myocardial blood flow of various interventions or conditions. Yet, calculating absolute blood flow for clinical studies remains rare. The result is that diagnostic decisions are usually based on relative myocardial blood flow or relative changes in myocardial blood flow between rest and stress, often aided by a software tool that compares images to a normal database.

There are at least three different kinetic models that have been used to understand the distribution over time of flow tracers in myocardial tissue. These works include spillover correction because of a finite resolution of the scanner and because the myocardium is moving during the scan. In one known approach, factor analysis was used to obtain spillover independent time activity curves of the right ventricle (RV) and left ventricle (LV) and myocardial blood tissue. By using curves generated from factor analysis, the spillover component in the model can be eliminated in theory; however, factor analysis does not correct for the under measurement due to the partial volume effect. Correction for this would require the use of a contrast recovery coefficient. Methods for addressing the non-uniqueness problem of kinetic modeling have been proposed. Also, kinetic modeling directly from sinograms from a dynamic sequence has been suggested.

In the following, let $a_{ij}$ denote the activity in voxel i of frame j. In factor analysis, it is assumed that the activity is a linear combination of K primary factor curves, where the summation coefficients are $$a_{ij} = \sum_{k=1}^{K} c_{ik} f_{kj}. \tag{1}$$

The primary factor curves for this application are the right ventricular blood pool, the left ventricular blood pool, and the myocardial tissue curve. The mathematical task is to find both the factors and coefficients so that the linear combination of factor curves for every pixel in the image matches the measured curve as close as possible. This problem is constrained by requiring that the tissue curves and the linear coefficients are all positive.

Ammonia or Rubidium uptake is generally analyzed with a two or three compartment model. The models all have a blood compartment in contact with an extracellular free distribution compartment, which is in turn in contact with a metabolically trapped compartment. These models are much easier to calculate if it is assumed that the clearance from the metabolically trapped compartment is zero (or near zero) over the duration of the experiment. As a result, for accurate myocardial blood flow modeling, several authors recommend collecting and analyzing only two minutes of data. When using smooth data generated by averaging all pixels within a large range of interest, this is a reasonable approach.

While there have been significant advances in the art, further advances are possible. For example, it is desirable to have a myocardial blood flow analysis with greater accuracy than is presently known in the art.

SUMMARY

Generally speaking, pursuant to these various embodiments, techniques for estimating myocardial blood flow (MBF) in each voxel in the myocardium, and specifically to a method for estimating myocardial blood flow in each voxel in the myocardium using a model using pharmacological kinetics based factor analysis of dynamic structures (K-FADS) and using a discretization that transforms the continuous-time K-FADS model into a discrete-time K-FADS model, then applying an iterative algorithm, such as a Voxel-Resolution myocardial blood flow (V-MBF) algorithm.

In one approach, a myocardial blood flow analysis includes a processing device applying a pharmacological kinetic model to a data set stored in a storage device. The data set may be compiled from a PET scan or other imaging approach that can monitor fluid flow in a voxel set. For example, the data set may be derived from an imaging technique based on monitoring fluid based tracers in a left ventricle, a right ventricle, and myocardium of a patient or animal subject. By one aspect, the pharmacological kinetic model includes incorporating a model of changing concentrations of bound fluid based tracers, unbound fluid based tracers, and blood plasma fluid based tracers into a standard factor analysis of dynamic structures model combined with a model of fluid based tracer activity in the left ventricle as a time shifted and dispersed function of blood flow from the right ventricle. In another approach, the tracer activity is modeled without assumption that a right ventricle tissue curve and a left ventricle tissue curve obey a particular mathematical relationship. The processing device is configured to output a processed data set based on the application of the pharmacological kinetic model to the data set for providing a representation of blood flow in the myocardium. The processed data set may be usable to create a visual representation, an audio representation, a textural description of the myocardial blood flow using known methods for conveying such information.

In other aspects, the processing device optionally estimates parameters of the standard factor analysis of dynamic structures model. The estimating may be done by estimating maximum values of fluid based tracer activity in one or both of the right ventricle or the left ventricle and modifying a corresponding signal vector value for the one of the right ventricle or the left ventricle using the estimated maximum values of fluid based tracer activity. In still another approach, the estimating may be done by estimating a left ventricle time activity curve, a right ventricle time activity curve, and a time activity curve, wherein the left ventricle time activity curve is assumed to be approximately equal to a response of an mth-order, all-pole filter applied to the right ventricle time activity curve and determining a set of parameters that produce a smallest least-squares error for the pharmacological kinetic model. This estimation may include for a given initial estimate right ventricle time activity curve and a given initial estimated left ventricle time activity curve, determining initial estimates for parameters of the pharmacological kinetic model.

Where the model is applied without assumption that a right ventricle tissue curve and a left ventricle tissue curve obey a particular mathematical relationship, a least squares objective function can be applied to obtain estimates for parameters of the pharmacological kinetic model. In one such approach, the least squares objective function is minimized by applying a majorize-minimize optimization technique to iteratively estimate the right ventricle tissue curve and the left ventricle tissue curve. At initialization, initial estimates for an initial estimated right ventricle time activity curve and an initial estimated left ventricle time activity curve are estimated and use the initial estimates for the initial estimate right ventricle time activity curve and the initial estimated left ventricle time activity curve to determine initial parameters of the pharmacological kinetic model. Where the data is noisy, the processing device smoothing estimates for blood flow for a given voxel by applying a limiting factor or penalty factor on data from voxels located within a given distance from the given voxel. Optionally, the pharmacological kinetic model includes a semi-parametric model configured to drive time activity curves for the right ventricle imaging activity from the fluid based tracers and the left ventricle imaging activity from the fluid based tracers to zero over time.

So configured, a more accurate derivation of myocardial blood flow is possible through the application of these modeling techniques. The advantages include increased resolutions and incorporation of kinetics. Further, unlike most known iterative algorithms for MBF estimation, such approaches explicitly describe a general procedure for initializing such algorithms. Other features will become more apparent to persons having ordinary skill in the art from the following description and claims.

BRIEF DESCRIPTION OF THE DRAWINGS

The foregoing features, as well as other features, will become apparent with reference to the description and figures below, in which like numerals represent elements, and in which:

FIG. 3 illustrates example results for plane 9 using the IV-MBF algorithm where FIG. 3A illustrates MBF estimates displayed as an image, FIG. 3B illustrates a mask used to define myocardium voxels, FIG. 3C illustrates the image obtained by averaging the PET images for the last six sub-scans, and FIG. 3D illustrates a histogram of the MBF estimates.

FIG. 4 illustrates example results for plane 16 using the IV-MBF algorithm, where FIG. 4A illustrates MBF estimates displayed as an image, FIG. 4B illustrates a mask used to define myocardium voxels. FIG. 4C illustrates the image obtained by averaging the PET images for the last six sub-scans, and FIG. 4D illustrates a histogram of the MBF estimates.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

A method and apparatus for estimating myocardial blood flow (MBF) in each voxel in the myocardium is described. The algorithm is based on a factor analysis of dynamic structures (FADS) model that has been enhanced to constrain the factor analysis curves to be physiologically appropriate.

Figure 1:
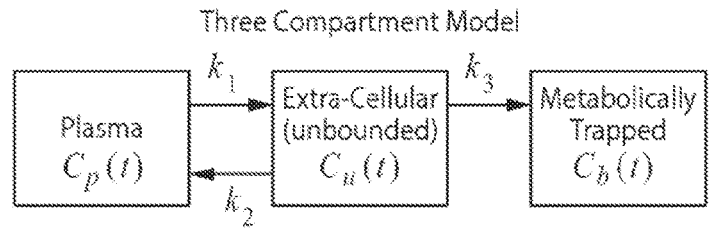
FIG. 1 illustrates a generalization of a 3-compartment model used to model Rubidium or Ammonia kinetics in the heart.

Turning now the figures, FIG. 1 illustrates a generalization of a 3-compartment model used to model Rubidium or Ammonia kinetics in the heart. Tracer in the second compartment is freely diffusible, while the tracer in the third compartment is trapped. The unknown parameters $k_1$, $k_2$, and $k_3$ are first order rate constants that describe the tracer movement between the compartments. The parameter $k_1$ (ml/min/g) is identified as myocardial blood flow. A first approach to analyzing MBF will now be described.

I. A First Approach

The kinetic behavior of ammonia in the myocardium is modeled with the compartment model shown in FIG. 1 and the following differential equations (note: assume $k_4$=0):

$$\frac{dC_u(t)}{dt} = k_1 C_p(t) - (k_2 + k_3)C_u(t) \quad (2)$$

$$\frac{dC_b}{dt} = k_3 C_u(t), \quad (3)$$

where $C_p$ is the ammonia concentration in blood plasma, $C_u$ is the concentration of the free (i.e., unbound) ammonia, and $C_b$ is the concentration of the trapped (i.e., bound) ammonia.

In one approach, a model is applied that incorporates a pharmacological kinetic model with the standard FADS model, which is a model where each time activity curve is assumed to be a linear combination of factor curves. The resulting model, which can be called the pharmacological kinetics based factor analysis of dynamic structures (K-FADS) model, provides a means for estimating factor curves in the myocardium that are physiologically meaningful. Further, a discretization is performed to transform continuous-time K-FADS model into a discrete-time K-FADS model. It should be noted that there is a simple relationship between the discrete-time and continuous-time K-FADS parameters.

Next, an iterative algorithm can be applied, such as the Voxel-Resolution myocardial blood flow (V-MBF) algorithm. This algorithm can iteratively estimate the MBF for each voxel in the myocardium. The V-MBF algorithm is reliably initialized using an input-output system identification method described by Steiglitz-McBride. This method can be applicable to a class of discrete-time systems that includes the discrete K-FADS model. This V-MBF algorithm was evaluated subjectively and objectively through experiments conducted using synthetic data and found to be reliable in considered test scenarios. Accordingly, the method disclosed herein is feasible for determining physiologically meaningful estimates of absolute MBF.

The initial model is a continuous-time K-FADS model from which a discrete-time K-FADS model can be obtained by applying a bilinear transform to the continuous-time K-FADS model. It should be noted that there is a simple relationship between the discrete-time and continuous-time K-FADS parameters. Using a systems theory framework, the problem of estimating the discrete-time K-FADS parameters is related to the problem of identifying a discrete-time system from given input and output data (i.e., input-output system identification). The V-MBF algorithm iteratively estimates the MBF for each voxel in the myocardium. The V-MBF algorithm can be initialized using an input-output system identification method, such as one described by Steiglitz-McBride, which is applicable to a class of discrete-time systems that includes the discrete K-FADS model. Each of these aspects will be described in turn with respect to a first approach to estimating the MBF for voxels of the cardiac system.

Continuous-Time K-FADS Model

For convenience, the RV factor, LV factor (i.e., Cp). Cu, and Cb can be denoted by the continuous-time functions $f_1(t)$, $f_2(t)$, $f_{i,3}(t)$, and $f_{i,4}(t)$, respectively, where i is the voxel index. With this notation it follows that $f_1$ and $f_2$ represent the activity concentration of the ammonia in the right ventricle and left ventricle, respectively. Additionally, $f_{i,3}(t)$, and $f_{i,4}(t)$ represent the activity concentration of free and trapped ammonia in myocardial tissue, respectively. It can be seen that it is assumed that the RV (right ventrical) and LV (left ventrical) factors are spatially constant (i.e., RV and LV factor are voxel independent). In the continuous-time K-FADS model the LV factor is modeled as a time shifted and dispersed function of the RV factor $$f_2(t)=\gamma f_1(t)*\exp(-\beta(t-\tau))u(t-\tau) \quad (4)$$

where γ, β, and τ (tau) are the unknown gain, time constant, and delay of the LV, respectively. Specifically, τ (tau) accounts for the fact that the ammonia activity first appears in the right ventricle and then, after a period of time, appears in the LV. The function u is the unit step function, and the notation * denotes the continuous-time convolution operator. The model for the LV factor in (4) can be motivated by observations of "isolated" RV and LV factors obtained from dynamic PET sequences and, in part, by the need for mathematical tractability. For example, consider if parameters $k_1$, $k_2$, and $k_3$ are pixel dependent and voxel i lies in the myocardium, then, applying the Laplace transform to (3) can lead to the following expressions for the activity concentration of the free and trapped ammonia in voxel i $$f_{i,3}(t)=k_{i,1}f_2(t)*\exp(-(k_{i,2}+k_{i,3})t)u(t) \quad (5)$$

$$f_{i,4}(t)=k_{i,3}f_{i,3}(t)*u(t). \quad (6)$$

It is noted that $k_{1,1}, k_{2,1}, \ldots, k_{I,1}$ are the preferred MBF parameters. In keeping with the assumptions behind (1), the activity for the ith pixel can be expressed as $$a_i(t) = c_{i,1} f_1(t) + c_{i,2} f_2(t) + c_{i,3} f_{i,3}(t) + c_{i,4} f_{i,4}(t). \quad (7)$$

The first term in (7) can be identified as the amount of spillover from the right ventricle, and the second term can be a combination of the ammonia activity in blood vessels within the myocardium and spillover from the left ventricle. More specifically, the constant $c_{i,1}$ accounts for the amount of the measured radioactivity in voxel in the case of a PET scan that is due to the blood plasma in the RV. Further, the constant $c_{i,2}$ accounts for the amount of the measured radioactivity in voxel i that is due to blood plasma in the LV (i.e., LV spill over) and blood plasma in the blood vessels of the myocardium. For this approach, it is assumed that $c_{i,2}=0.05$. The third and fourth terms in (7) are the activity of the free and trapped ammonia in the myocardial tissue, respectively. The coefficients $c_{i,3}$ and $c_{i,4}$ represent the fractional volume of voxel i that can be occupied by the radiotracer in either the free or trapped states. Given the free space for water in myocardial tissue is approximately 80 percent, it is assumed that $c_{i,3}=c_{i,4}=0.8$.

Within the descriptions herein, it can be convenient to let $f(t)=f_1(t)$ and $c_i=c_{i,1}$. From equations (4), (5), (6), and straightforward calculations, the functions $f_{i,3}(t)$ and $f_{i,4}(t)$ can be written as:

$$k_i = k_{i,2} + k_{i,3} \quad (8)$$

$$f_{i,3}(t) = -f(t) * [\exp(-\beta(t-\tau)) - \exp(-k_i(t-\tau))] u(t-\tau) \quad (9)$$

$$f_{i,4}(t) = \gamma k_{i,1} k_{i,3} f(t) * \left[ \frac{\exp(-\beta(t-\tau))}{\beta(\beta-k_i)} - \frac{\exp(-k_i(t-\tau))}{k_i(\beta-k_i)} + \frac{1}{\beta k_i} \right] u(t-\tau) \quad (10)$$

By substituting these equations into (7) it can be shown that $$a_i(t) = \quad (11)$$
$$c_i f(t) + f(t) * [b_{i,1} + b_{i,2} \exp(-\beta(t-\tau)) + b_{i,3} \exp(-k_i(t-\tau))] u(t-\tau),$$

where $$b_{i,1} \triangleq \frac{\gamma c_{i,4} k_{i,1} k_{i,3}}{\beta k_i} \quad (12)$$

$$b_{i,2} \triangleq \gamma \left( c_{i,2} - \frac{c_{i,3} k_{i,1}}{\beta - k_i} + \frac{c_{i,4} k_{i,1} k_{i,3}}{\beta(\beta - k_i)} \right) \quad (13)$$

$$b_{i,3} \triangleq \frac{\gamma k_{i,1}}{\beta - k_i} \left( c_{i,3} - \frac{c_{i,4} k_{i,3}}{k_i} \right) \quad (14)$$

It can also be shown from straightforward calculations that $$k_{i,1} = \frac{c_{i,2}}{c_{i,3}} \frac{(\beta - k_i) b_{i,3} + \beta b_{i,1}}{b_{i,1} + b_{i,2} + b_{i,3}}. \quad (15)$$

Thus, given estimates for the parameters $\beta$, $\{k_i\}$, $\{c_i\}$, $\{b_{i,1}\}$, $\{b_{i,2}\}$, and $\{b_{i,3}\}$, and using the assumed values for $\{c_{i,2}\}$ and $\{c_{i,3}\}$, the MBF parameters $\{k_{i,1}\}$ can be estimated from equations (15). As stated above, it is assumed that $c_{i,2}=0.05$ and $c_{i,3}=0.8$ for all i.

Discrete-Time K-FADS Model

The next aspect of this approach is to address the problem of estimating the parameters $\beta$, $\{k_i\}$, $\{c_i\}$, $\{b_{i,1}\}$, $\{b_{i,2}\}$, and $\{b_{i,3}\}$ from discrete-time Time Activity Curve (TAC) data because continuous-time TAC data is not available in practice.

In practice, only samples of the TACs are available so let $y_i[n]$, $i=1, 2, \ldots I$ and $x[n]$ denote the discrete-time signals obtained by sampling the ith TAC $a_i(t)$ and RV factor respectively $$y_i[n] \triangleq a_i(nT), n=0, 1, \ldots, N-1 \quad (16)$$

$$x[n] \triangleq f(nT), n=0, 1, \ldots, N-1, \quad (17)$$

where $f_s \triangleq 1/T$ is the sampling rate and T is the sampling interval. It is noted that in applications where scan durations for dynamic sequence PET protocols are not uniform, the assumption that the TACs are sampled uniformly is inappropriate. However, uniform samples of the TACs can be obtained from non-uniform samples of the TACs via a suitable interpolation. It follows that, in order to estimate the MBF parameters, the parameters $\beta$, $\{k_i\}$, $\{c_i\}$, $\{b_{i,1}\}$, $\{b_{i,2}\}$, and $\{b_{i,3}\}$ are estimated from the data $y_i[n]$, $n=0, 1, \ldots, N-1$. It can be observed that the parameters $\{c_i\}$ are really nuisance parameters because they do not show up in the expression for $k_{i,1}$ (see equation (15)).

It is of interest to determine a discrete-time system with the property that its response to the discrete-time RV factor $x[n]$ closely approximates the ith discrete-time TAC $y_i[n]$. The bilinear transformation is a way to transform a linear time-invariant continuous-time system into a linear time-invariant discrete-time system. A limitation of the bilinear transform is that a delay in a continuous-time system must be an integer multiple of the sampling interval. Taking the Laplace transform of (11), we get the following relationship $$A_i(s) = c_i F(s) + F(s) \left( b_{i,1} \frac{1}{s} + b_{i,2} \frac{1}{s+\beta} + b_{i,3} \frac{1}{s+ki} \right) \exp(-s\tau), \quad (18)$$

$$i = 1, 2, \ldots, I$$

As a result, it follows that the system function of the overall continuous-time system is given by $$H_{i,tot}(s) \triangleq \quad (19)$$

$$\frac{A_i(s)}{F(s)} = c_i + \left( b_{i,1} \frac{1}{s} + b_{i,2} \frac{1}{s+\beta} + b_{i,3} \frac{1}{s+ki} \right) \exp(-s\tau)$$

Assuming the delay t is a multiple of the sampling interval T, the system function of the desired discrete-time system, $H_i(z)$, can be obtained by applying the bilinear transformation to the overall continuous-time system $H_{i,tot}(s)$ $$H_i(z) = c_i + \left( \left[ b_{i,1} \frac{1}{s} + b_{i,2} \frac{1}{s+\beta} + b_{i,3} \frac{1}{s+ki} \right] \bigg|_{s=\frac{2}{T} \frac{1-s^{-1}}{1+s^{-1}}} \right) z^{-d} = \quad (20)$$

$$c_i + \left( b'_{i,1} \frac{1+z^{-1}}{1-r_1 z^{-1}} + b'_{i,2} \frac{1+z^{-1}}{1-r_2 z^{-1}} + b'_{i,3} \frac{1+z^{-1}}{1-r_{i,3} z^{-1}} \right) z^{-d} \quad (21)$$

where $\tau=dT$ for some integer d, $r_1=1$, $r_2=(2/T+\beta)^{-1}(2/T-\beta)$, $r_{i,3}=(2/T+k_i)^{-1}(2/T-k_i)$, $b'_{i,1}=b_{i,1}(2/T)^{-1}$, $b'_{i,2}=b_{i,2}(2/T+\beta)^{-1}$, and $b'_{i,3}=b_{i,3}(2/T+k_i)^{-1}$.

It is noted that for this approach, the z-transform is used. Here let g[n] be an arbitrary discrete-time sequence. The z-transform g[n] can be defined as $$G(z) = \sum_{n=-\infty}^{\infty} g[n] Z^{-n}.$$

It should be noted that the delay term (i.e., $z^{-d}$ term) in equation (21) follows from the $\tau$ second delay in the continuous-time K-FADS model, which is the delay between activity appearing in the right and left ventricles.

As known in the art, the bilinear transformation has the property that it maps a stable continuous-time system into a stable discrete-time system. Moreover, the bilinear transformation avoids the problem of aliasing by mapping the $j\Omega$ axis into the unit circle of the complex plane. However, "frequency warping" can occur as a result of mapping the entire $j\Omega$ axis into the unit circle. Note, the frequency warping problem can be ameliorated by choosing a sufficiently high sampling rate $f_s$.

It follows from the definition in equation (21) that the discrete-time K-FADS model for the ith TAC can be represented by the following input-output relationship $$Y_i(z) = X(z)H_i(z; d, r_2, r_{i,3}, \theta_i) = c_i X(z) + \qquad (22)$$
$$X(z)\left[b'_{i,1}\frac{1+z^{-1}}{1-r_1 z^{-1}} + b'_{i,2}\frac{1+z^{-1}}{1-r_2 z^{-1}} + b'_{i,3}\frac{1+z^{-1}}{1-r_3 z^{-1}}\right]z^{-d}$$

where $\theta_i \triangleq [b'_{i,1}, b'_{i,2}, b'_{i,3}, c_i]$ (recall $r_1=1$). The notation $H_i(z; d, r_2, r_{i,3}, \theta_i)$ explicitly illustrates the dependence of the ith system function on the unknown parameters. For the discussion below, it is beneficial to define the following notation:

$\theta_{r_3} \triangleq [r_{1,3}, r_{2,3}, \ldots, r_{I,3}]$ $\theta_{b'} \triangleq [b'_{1,1}, b'_{2,1}, \ldots, b'_{I,1}, b'_{1,2}, b'_{2,2}, \ldots, b'_{I,2}, b'_{1,3}, b'_{2,3}, \ldots, b'_{I,3}]$ $c \triangleq [c_1, c_2, \ldots, c_I]. \qquad (23)$ The problem of interest is to estimate parameters of the discrete-time K-FADS model from the sampled TACs $y_i[n]$, $I=1, 2, \ldots, I$. Therefore, the V-MBF algorithm of this approach solves the following least-squares problem $$(P)(\hat{x}, \hat{d}, \hat{r}_2, \hat{\theta}_{r_3}, \hat{\theta}_{b'}, \hat{c}) = \arg\min_{x \geq 0, \theta \in s_\theta} \phi(x, d, r_2, \theta_{r_3}, \theta_{b'}, c), \qquad (24)$$

where $$\phi(x, d, r_2, \theta_{r_3}, \theta_{b'}, c) \triangleq \qquad (25)$$
$$\sum_{i=1}^{I} \sum_{n=1}^{N} (y_i[n] - x[n] * h_i[n; d, r_2, r_{i,3}, \theta_i])^2$$

$$\theta \triangleq [d, r_2, \theta_{r_3}, \theta_{b'}, c]. \qquad (26)$$

Additionally, $S_\theta$ is a feasible set of the parameters $\theta$ and $h_i[n; d, r_2, r_{i,3}, \theta_i]$ is the inverse Z-transform of $H_i(z; d, r_2, r_{i,3}, \theta_i)$.

In the development of the V-MBF algorithm, the problem (P) is simplified by assuming that the discrete-time d delay is known. Next, this assumption is removed by estimating the parameter d along with the other parameters of the discrete-time K-FADS model. An initialization method is applied that exploits the well known Steiglitz-McBride algorithm.

A. Discrete-Time Delay Known

To minimize the objective function $\phi$ in (24), an algorithm is developed based on the group coordinate-descent method. By use of the term group coordinate-descent method it is understood that, in a cyclic fashion, the objective function $\phi$ is minimized with respect to a set of parameters while the other parameters are fixed.

Let $d_0$ denote the known discrete-time delay. Given initial estimates, $x^{(0)}, r_2^{(0)}, \theta_{r_3}^{(0)}, \theta_{b'}^{(0)}, c^{(0)}$ an algorithm for solving (P) proceeds as follows:

For m = 0, 1, . . . , M − 1 or repeat until some chosen criterion is met:

Step 1 $\quad x^{(m+1)} = \arg\min_{x \geq 0} \phi(x, d_0, r_2^{(m)}, \theta_{r_3}^{(m)}, \theta_{b'}^{(m)}, c^{(m)})$ Step 2 $\quad (r_2^{(m+1)}, \theta_{r_3}^{(m+1)}) = \arg\min_{0 < r_2, \theta_{r_3} < 1} \phi(x^{(m+1)}, d_0, r_2, \theta_{r_3}, \theta_{b'}^{(m)}, c^{(m)}) \qquad (27)$ Step 3 $\quad (\theta_{b'}^{(m+1)}, c^{(m+1)}) = \arg\min_{0 \leq c \leq 1} \phi(x^{(m+1)}, d_0, r_2^{(m+1)}, \theta_{r_3}^{(m+1)}, \theta_{b'}, c) \qquad (28)$ end Solution to Step 1 of the V-MBF Algorithm with Known Delay In the solution to Step 1 of the V-MBF algorithm with known delay d, it is convenient to denote the next estimate for the RV factor as $\bar{x} \triangleq x^{(m+1)}$. Given its simplicity, the coordinate descent algorithm is used to iteratively determine $\bar{x}$. Let $e_1, e_2, \ldots, e_N$ be the search directions, where $e_j$ is an N×1 vector of zeros except for a 1 at the jth position. The steps of the coordinate descent algorithm for determining the update $x^{(m+1)}$ are as follows: Let $z_1 = x^{(m)}, \bar{x}^{(0)} = x^{(m)}, j=1$, and $l=0$, and choose $\epsilon > 0$ Step 1.1 Determine $\lambda_j = \arg\min_\lambda \phi(z_j + \lambda e_j), d_0, r_2^{(m)}, \theta_{r_3}^{(m)}, \theta_{b'}^{(m)}, c^{(m)})$ Step 1.2 Let $z_{j+1} = z_j + \lambda_j e_j$. If jth component of $z_{j+1}$ is negative, then this value is set to zero. Note, this operation accounts for the nonnegativity constraint of the discrete-time RV factor. If j<N, then increment j and repeat Step 1.1. Otherwise, if j=N, then go to Step 1.3.

Step 1.3 Let $\bar{x}^{(l+1)} = z_{N+1}$. If $\|\bar{x}^{(l+1)} - \bar{x}^{(l)}\| < \epsilon$ (or a specified number of desired iterations is reached), then stop and let $x^{(m+1)} = \bar{x}^{(l+1)}$. Else, let $z_1 \triangleq \bar{x}^{(l+1)}$ and j=1, increment l, and go to Step 1.1. Note, the step size $\lambda_j$ has a closed form expression.

Solution to Step 2 of the V-MBF Algorithm with Known Delay

Again, the simplicity of the coordinate descent method is exploited to compute a solution to the problem in Step 2. However, the coordinate descent method is expressed in a manner that is more convenient for this problem:

repeat until
$$\|\theta_r^{(m+1)} - \theta_r^{(m)}\| < \epsilon \text{ where } \theta_r^{(m)} \triangleq [r_2^{(m)}, r_{1,3}^{(m)}, r_{2,3}^{(m)}, \ldots, r_{I,3}^{(m)}]$$

Step 2.1: $r_2^{(m+1)} = \arg\min_{0<r_2<1} \phi(x^{(m+1)}, d_0, r_2, \theta_{r_3}^{(m)}, \theta_{b'}^{(m)}, c^{(m)})$ Step 2.2: for $i = 1, 2, \ldots, I$, $$r_{i,3}^{(m+1)} = \arg\min_{0<r_3<1} \sum_{n=1}^{N} (y_i[n] - x^{(m+1)}[n] * h_i[n; d, r_2^{(m+1)}, r_3, \theta_i^{(m+1)}])^2 \quad (29)$$

end
end

It should be observed that in Step 2.2 advantage is taken of the fact that the objective function $\phi$ is de-coupled in terms of the parameters $r_{1,3}, r_{2,3}, \ldots, r_{I,3}$. Also, a 1-D line search algorithm such as the golden section method can be used to solve the 1D minimization problems in Steps 2.1 and 2.2.

Solution to Step 3 of the V-MBF Algorithm with Known Delay

Referring to equation (25), it follows that the problem in equation (28) is equivalent to the following problems, $i=1,2,\ldots,I$, $$\theta_i^{(m+1)} = \arg_{0 \leq c_i \leq 1} \min_{b'_{i,1}, b'_{i,2}, b'_{i,3}} \sum_{n=1}^{N} (y_i[n] - c_i x^{(m+1)}[n] - b'_{i,1} w_1^{(m+1)}[n] - b'_{i,2} w_2^{(m+1)}[n] - b'_{i,3} w_3^{(m+1)}[n])^2 \quad (30)$$

where, $w_p^{(m+1)}[n]$, $p=1, 2$, is the inverse Z-transform of $$W_p^{(m+1)}(z) = X^{(m+1)}(z) \frac{1 + z^{-1} z^{-d}}{1 - r_p z^{-1}}, \; p = 1, 2, \quad (31)$$

and $w_{i,3}^{(m+1)}[n]$ is the inverse Z-transform of $$W_{i,3}^{(m+1)}(z) = X^{(m+1)}(z) \frac{1 + z^{-1} z^{-d}}{1 - r_{i,3}^{(m+1)} z^{-1}}. \quad (32)$$

An optimization problem in equation (30) is a linear least-squares problem under the constraint $0 \leq c_i \leq 1$. If the constraint on $c_i$ ignored, then the update $\theta_i^{(m+1)}$ could be computed by solving the normal equations associated with the least-squares objective function in (30). Thus, if the solution to an unconstrained version of the least-squares problem in (30) is such that $0 \leq c_i^{(m+1)} \leq 1$ for all i, then no other steps should be necessary. Alternatively, if without loss of generality, the constraint is not satisfied for $i=i_0$, then additional steps should be taken. A straightforward strategy could be to first compute the updates $b'^{(m+1)}_{i_0,1}$, $b'^{(m+1)}_{i_0,2}$, and $b'^{(m+1)}_{i_0,3}$ by solving the normal equations associated with the following least-squares problem $$(b'^{(m+1)}_{i_0,1}, b'^{(m-1-\pi)}_{i_0,2}, b'^{(m+1)}_{i_0,3}) = \quad (33)$$

$$\arg\min_{b'_{i_0,1}, b'_{i_0,2}, b'_{i_0,3}} \sum_{n=1}^{N} (y_{i_0}[n] - c_{i_0}^{(m)} x^{(m+1)}[n] - b'_{i_0,1} w_1^{(m+1)}[n] - b'_{i_0,2} w_2^{(m+1)}[n] - b'_{i_0,3} w_3^{(m+1)}[n])^2$$

The update $c_{i_0}^{(m+1)}$ could then be computed using the coordinate descent method $$c_{i_0}^{(m+1)} = \arg\min_{0 \leq c \leq 1} \sum_{n=1}^{N} (y_{i_0}[n] - cx^{(m+1)}[n] - b'^{(m+1)}_{i_0,1} w_1^{(m+1)}[n] - b'^{(m+1)}_{i_0,2} w_2^{(m+1)}[n] - b'^{(m+1)}_{i_0,3} w_{i_0,3}^{(m+1)}[n])^2 \quad (34)$$

Iterating between equations (33) and (34) may lead to improved estimates for $c_{i_0}$, $b'_{i_0,1}$, $b'_{i_0,2}$, and $b'_{i_0,3}$.

Discrete-Time Delay Unknown

In the example above, the discrete-time delay d was assumed as known. Nevertheless, in practice it must be estimated. Let the integers $d_{min}$ and $d_{max}$ be the assumed minimum and maximum values for d. Then, the complete V-MBF algorithm follows for $d=d_{min}, \ldots, d_{max}$.

1. minimize $\phi(x, d, r_2, \theta_{r_3}, \theta_{b'}, c)$ using the algorithm in the V-MBF algorithm assuming known discrete-time delay section within Section A (i.e., V-MBF algorithm assuming know discrete-time delay)

2. Store parameter estimates and value of least-squares objective function end

The preferred estimates for the K-FADS parameters in this approach produce the smallest least-square error. The estimates for the MBF parameters are obtained using equation (15) and the estimates:

$$\hat{\beta} = \frac{2}{T} \frac{1 - \hat{r}_2}{1 + \hat{r}_2} \quad (35)$$

$$\hat{k}_i = \frac{2}{T} \frac{1 - \hat{r}_{i,3}}{1 + \hat{r}_{i,3}} \quad (36)$$

$$\hat{b}_{i,1} = \hat{b}'_{i,1} \frac{2}{T} \quad (37)$$

-continued $$\hat{b}_{i,2} = \hat{b}'_{i,2}\left(\frac{2}{T} + \hat{\beta}\right) \quad (38)$$

$$\hat{b}_{i,3} = \hat{b}'_{i,3}\left(\frac{2}{T} + \hat{k}_i\right), \quad (39)$$

and the assumed values $c_{i,2}=0.05$ and $c_{i,3}=0.8$ for all i.

Initialization Procedure

To start the V-MBF algorithm, initial estimates for the RV factor x, $r_2$, and $\theta_{r_3}$ needed. One method for obtaining an initial estimate for the RV factor $x^{(0)}$ is for a user selected TAC of a voxel to be used that can essentially remain in the right ventricle throughout the duration of the scan. To generate initial estimates for $r_2$, and $\theta_{r_3}$, the known Steiglitz-McBride algorithm may be used.

To develop a method for computing an initial estimate, first observations can be used from equation (22) that for some 3rd-order polynomial $Q_i(z)$ and 2nd-order polynomial $P'_i(z)$, the z-transform of the ith TAC, is given by $$Y_i(z) = c_i X(z) + X(z)\frac{P'_i(z)(1+z^{-1})}{Q_i(z)}z^{-d}, i = 1, 2, \ldots, I, \quad (40)$$

where the roots of Qi(z) are $r_1$, $r_2$, and $r_{i,3}$. Alternatively, for some polynomial $P'_i(z)$, equation (40) can be written as $$Y_i(z) = X(z)\frac{P_i(z)}{Q_i(z)}, i = 1, 2, \ldots, I, \quad (41)$$

where the unknown numerator polynomial is of the form $P_i(z)=p_{i,0}+p_{i,1}z^{-1}+p_{i,2}z^{-2}+p_{i,3}z^{-3}+p_{i,d}z^{-d}+p_{i,d+1}z^{-(d+1)}+p_{i,d+2}z^{-(d+2)}+p_{i,d+3}z^{-(d+3)}$ because $P_i(z)=c_iQ_i(z)+P'_i(z)(1+z^{-1})z^{-d}$. In other words, each TAC is the output of an autoregressive moving-average (ARMA) model known in the art that is driven by the RV factor x[n].

Given an input-output pair for a linear, time-invariant system modeled as an ARMA model, the Steiglitz-McBride algorithm can provide estimates for ARMA parameters. Thus, given a TAC, $y_i[n]$, and initial RV factor $x^{(0)}$, the Steiglitz-McBride algorithm can be used, which is an iterative algorithm, to estimate $P_i(z)$ and $Q_i(z)$. The Steiglitz-McBride algorithm can be summarized below $$(p_i^{(m+1)}, q_i^{(m+1)}) = \quad (42)$$

$$\underset{p,q}{\mathrm{argmin}}\,\frac{1}{2\pi}\int_{-\pi}^{\pi}\left|\frac{Y_i(e^{j\omega})Q(e^{j\omega})}{Q_i^{(m)}(e^{j\omega})} - \frac{X^{(0)}(e^{j\omega})P(e^{j\omega})}{Q_i^{(m)}(e^{j\omega})}\right|^2 d\omega,$$

where the discrete-time Fourier transform is used to obtain:

$$Y_i(e^{j\omega}) = \sum_{k=0}^{N-1} y_i[k]e^{-j\omega k} \quad (43)$$

$$X^{(0)}(e^{j\omega}) = \sum_{k=0}^{N-1} x^{(0)}[k]e^{-j\omega k} \quad (44)$$

$$P(e^{j\omega}) = \sum_{k=0}^{3} p_k e^{-j\omega k} + \sum_{k=0}^{3} p_{d+k}e^{-j\omega k} \quad (45)$$

$$Q(e^{j\omega}) = 1 + \sum_{k=1}^{3} q_k e^{-j\omega k} \quad (46)$$

$$p = [p_0, p_1, p_2, p_3, p_d, p_{d+1}, p_{d+2}, p_{d+3}] \quad (47)$$

$$q = [q_1, q_2, q_3]. \quad (48)$$

Also $P_i^{(m)}(e^{jw})$, $Q_i^{(m)}(e^{jw})$, $p_i^{(m+1)}$, and $q_i^{(m+1)}$ can be similarly defined, and $Q_i^{(0)}(e^{jw})=1$ is the chosen initial estimate for $Q(e^{j\omega})$. Note, from Parseval's theorem, the objective function in (42) can be equivalent to a linear least-squares objective function. Thus, at the mth iteration, the Steiglitz-McBride algorithm entails a filtering step (i.e., initial RV factor $x^{(0)}[n]$ and ith TAC, $y_i[n]$, are filtered by $1/Q_i^{(m)}(z)$) and minimization of a linear least-squares objective function.

Let $\hat{Q}_i(z)$ denote the resulting estimate for $Q_i(z)$ using the Steiglitz-McBride algorithm and $z_{i,1} \geq z_{i,2} \geq z_{i,3}$ the roots of $\hat{Q}_i(z)$. The estimates for $r_2$ and $r_{i,3}$ are obtained from the roots of $\hat{Q}_i(z)$, I=1, 2, ..., I, in the following manner. Because if $\beta<1$ and $\beta>k_i$ by an order of magnitude and one of the roots of $Q_i(z)$ equals one, in theory, the initial estimates for the parameters $r_2$ and $r_{i,3}$ can be $r_2^{(0)}=\mathrm{avg}\{z_{1,2}, z_{2,2}, \ldots, z_{I,2}\}$ and $r_{i,3}^{(0)}=z_{i,3}$, respectively.

The Steiglitz-McBride algorithm is not used instead of the V-MBF algorithm to estimate the discrete-time K-FADS parameters when given an estimate for the RV factor because, for one reason, the roots of $\hat{Q}_i(z)$ are not guaranteed to be real with one root constrained to equal one, as required by the discrete K-FADS model. Another reason is that simulations discovered that estimating c and $\theta_b$, from the estimates $\hat{P}_i(z)$, $\hat{Q}_i(z)$, i=1, 2, ..., I, was not reliable.

Simulation Studies

To assess the potential of the V-MBF algorithm, simulated data was applied that modeled patient data used for cardiac health assessments. The model for the RV curve was $$f(t)=A(t-t_0)\exp(-\alpha(t-t_0))u(t-t_0), \quad (49)$$

where A=2700, $t_0$=14 seconds, and $\alpha$=0.12. Referring to equations (4), (5), (6), and (7), the parameters of the simulated data were $\gamma$=0.2, $\beta$=0.1, $\tau$=13 seconds, and for all i, $k_{i,2}$=0.001 s$^{-1}$, $k_{i,3}$=0.01 s$^{-1}$, $c_i$=0.03, $c_{i,2}$=0.05, $c_{i,3}$=0.8, $c_{i,4}$=0.8. Note, the V-MBF algorithm does not require that the parameters $c_i$, $k_{i,2}$, and $k_{i,3}$ be voxel independent. The values for these parameters were simply chosen for exemplary purposes. The MBF parameters $\{k_{i,1}\}$ (units s$^{-1}$) for the 20 voxel scenario that were considered were $k_1$=[0.0075,0.0462,0.0371,0.0233,0.0534,0.0281,
0.0320,0.0336,0.0433,0.0036,0.0083 0.0034,
0.0021,0.0103,0.0096,0.0345,0.0316,0.0031,
0.0257,0.0346]. (50)

The simulated TACs $a_i(t)$, I=1, 2, ..., I were computed using equation (11) and the above parameter values.

To model the integration characteristic of the scanner, the simulated TACs were integrated using a time-varying window. The resulting integrated data simulated the activity data that would actually be available in practice. A typical protocol used at an exemplary PET Center could leads to the following specification for the simulated integrated TACs (I-TACs)

$$g_k = \begin{cases} \frac{1}{T_1} \int_{(k-1)T_1}^{kT_1} a_i(t)\,dt, & k = 1, 2, \ldots, 20 \\ \frac{1}{T_2} \int_{(k-1)T_2}^{kT_2} a_i(t)\,dt, & k = 21, 22, \ldots, 25, \\ \frac{1}{T_3} \int_{(k-1)T_3}^{kT_3} a_i(t)\,dt, & k = 26, 27, \ldots, 31 \end{cases} \quad (51)$$

where $T_1=3$ seconds, $T_2=12$ seconds, and $T_3=30$ seconds.

The V-MBF algorithm can be based on standard TAC data (i.e., $a_i(nT)$). Consequently, the I-TAC data is preferably pre-processed. The I-TAC data is assumed to be nearly piece-wise linear. It follows using a known method from Kuhle that the standard TAC data at the midpoints of the windows is approximately:

$$a_i(0.5(kT_1+(k-1)T_1)) \approx g_k, \quad k=1, 2, \ldots, 20 \quad (52)$$

$$a_i(0.5(kT_2+(k-1)T_2)) \approx g_k, \quad k=21, 22, \ldots, 25 \quad (53)$$

$$a_i(0.5(kT_3+(k-1)T_3)) \approx g_k, \quad k=26, 27, \ldots, 31 \quad (54)$$

Now, standard sampled TAC data can be estimated from the measured activity data $\{g_k\}$ using interpolation. Specifically, the "known" values for $a_i(t)$, $\{a_i(0.5\,(kT_1+(k-1)T_1))\}_{k=1}^{20}$, $\{a_i(0.5\,(kT_2+(k-1)T_2))\}_{k=21}^{25}$, and $\{a_i(0.5\,(kT_3+(k-1)T_3))\}_{k=31}^{26}$ can be used (see equations (52), (53), and (54)), and linear interpolation to obtain estimates for $y_i[n]=a_i(nT)$, $n=0, 1, \ldots, N-1$. In the simulations, a preferred sampling interval is $T=0.05$ sec. It is noted that the approach described above for obtaining standard sampled TAC data would also be used to generate an initial RV factor from I-TAC data located in the RV.

Figure 2:
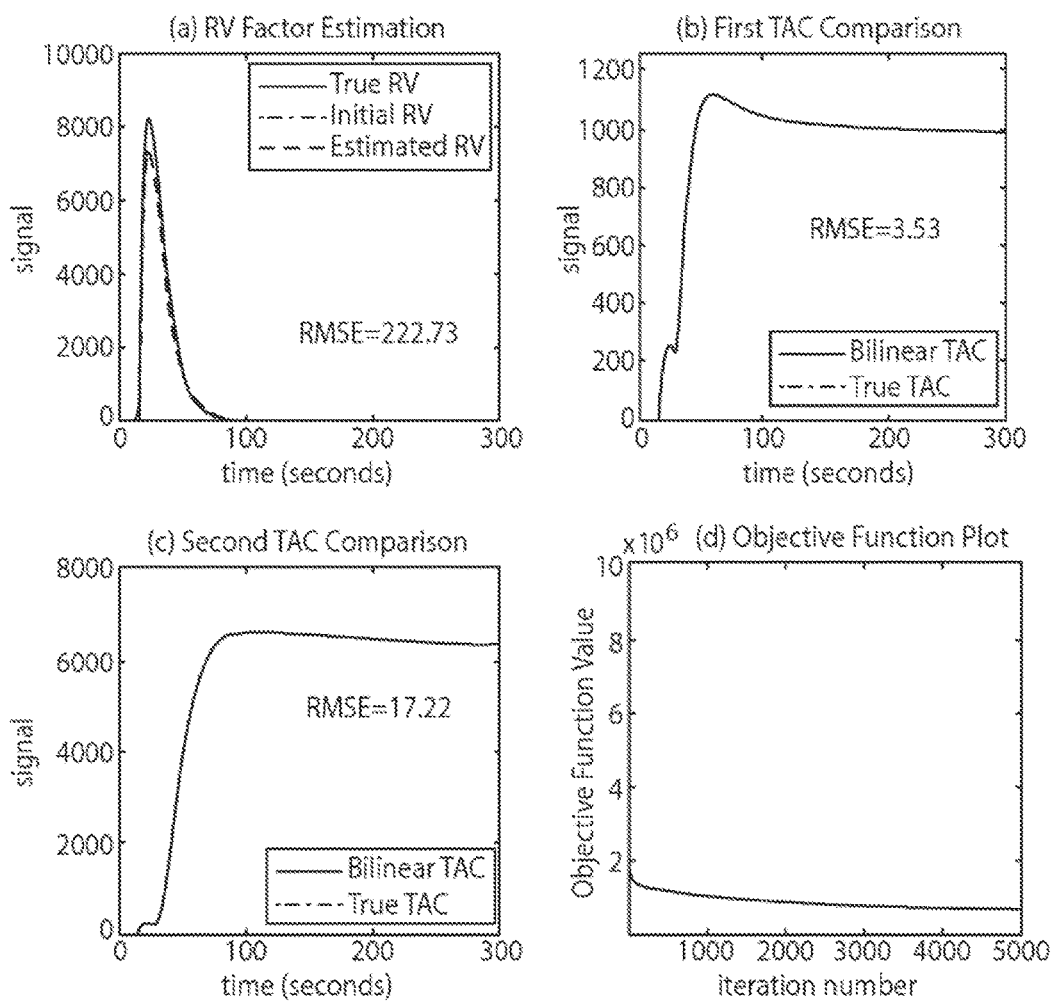
FIG. 2 illustrates results from a V-MBF algorithm applied to synthetic data: (a) true, initial, and estimated RV factor, (b) comparison of true TAC (computed analytically) and estimated TAC generated using the discrete-time K-FADS model and estimated parameters, (c) same as (b) except for a different TAC, and (4) least-squares objective function as a function of iteration number.

The V-MBF algorithm described above was applied for 5000 iterations where one sub-iteration was used to update the estimate for the RV curve. In this simulation, the maximum error in the MBF estimates was 1.5 percent. A typical result of a V-MBF algorithm is summarized in the FIG. 2, where (a) shows a true, initial, and estimated RV factor, (b) compares a true TAC (computed analytically) and with one generated using the discrete-time K-FADS model and estimated parameters, (c) is the same as (b) except for a different voxel, and (d) is a plot of the least-squares objective function as a function of iteration number. In the exemplary study, the V-MBF algorithm was stable and monotonically decreased the least-squares objective function (see FIG. 2(d)).

Thus, the V-MBF algorithm can be based on a model that accounts for the fact that the shape of TACs due to ischemic and normal tissue are different. In fact, the model can allow for the factors that represent free and trapped ammonia to be voxel dependent and physiologically appropriate. By contrast, in a standard FADS model, it is assumed that TACs in ischemic and normal tissue can be modeled as a linear combination of the same three factors. The present methods and systems represent a significant improvement in the art as a more appropriate model to provide more accurate MBF estimates than available methods.

The V-MBF algorithm presented herein performs well in simulation studies where unknown MBF parameters varied by an order of magnitude. This suggests that the V-MBF algorithm is robust and would perform well in practice, where MBF values due to ischemic and normal tissue can vary over a wide range. Although random noise was not added to the simulated TAC data, interpolation noise and noise due to the discretization of the continuous-time K-FADS model were present. Also, because only the integrated RV factor is available, the first time point where the RV factor is nonzero can never be known with certainty. With these three sources of noise, the maximum error of the MBF parameters estimates was 1.5 percent. It should be noted that including more data points should, lead to improved MBF estimates because the parameter $\beta$ is voxel independent.

II. A Second Approach

A second approach to MBF analysis will be described as follows. For clarity, equations will be renumbered to start with equation (1) within the discussion of this other approach.

As discussed above, the problem of estimating the weights and signal vectors of the above described models is a blind inverse problem. In this case, the data are nonnegative $J\times 1$ vectors $\{a_1, a_2, \ldots, a_J\}$ that are modeled as a weighted sum of signal vectors plus noise $$a_i = \sum_{k=1}^{K} c_{ik} f_k + e_i, \quad i = 1, 2, \ldots, I \quad (1)$$

where the $J\times 1$ signal vectors, $\{f_k\}$, and signal weights, $\{c_{i,k}\}$, are nonnegative and unknown, and $\{e_i\}$ is the noise. In our discussion of this approach, it will be convenient to use an equivalent expression for the model $$a_{ij} = \sum_{k=1}^{K} c_{ik} f_{jk} + e_{ij}, \quad (2)$$

$$i = 1, 2, \ldots, I, \; j = 0, 1, 2, \ldots, J-1,$$

where $a_{ij}$ and $e_{ij}$ are the jth components of $a_i$ and $e_i$, respectively, and $f_{jk}$ is the jth value of the kth signal vector. An example where this model is used is cardiac imaging using dynamic positron emission tomography (PET), where $a_{ij}$ is a measure of the radiopharmaceutical concentration in the ith voxel at the jth time point. Another example is multispectral imaging, where $a_{ij}$ represent the value of the ith pixel in the jth spectral plane.

Given the data $\{a_{ij}\}$, the problem is to estimate the weights $\{c_{jk}\}$ and signal vector values $\{f_{jk}\}$. The least-squares estimates of the weights and signal vector values are obtained by minimizing the least-squares objective function L subject to a non-negativity constraint.

$$(\hat{c}, \hat{f}) = \arg\min_{c\geq 0, f\geq 0} L(c, f), \quad (3)$$

where $$L(c, f) = \sum_{i=1}^{I} \sum_{j=0}^{J-1} \left( a_{ij} - \sum_{k=1}^{K} c_{ik} f_{jk} \right)^2. \quad (4)$$

The vectors c and f contain the signal weights and signal vector values, respectively:

$$c \triangleq [c_{11}, c_{21}, \ldots, c_{I1}, c_{12}, c_{22}, \ldots, c_{I2}, \ldots, c_{1K},$$
$$c_{2K}, \ldots, c_{IK}] \quad (5)$$

$$f \triangleq [f_{11}, f_{21}, \ldots, f_{J1}, f_{12}, f_{22}, \ldots, f_{J2}, \ldots,$$
$$f_{1K}, f_{2K}, \ldots, f_{JK}] \quad (6)$$

The least squares estimation problem is ill-posed, so the results are highly dependent on the initial estimates.

Estimation of Signal Vectors and Weights

A known standard least-squares algorithm by Lee and Seung monotonically decreased the least-squares objective function, L, and produced nonnegative estimates. In this section, this "standard least-squares algorithm" is re-derived using a known technique called the majorize-minimize method (MM). This derivation will place the proposed least-squares extensions in context so that their advantages over the standard least-squares algorithm are clear.

An approach for minimizing the least-squares objective function, L, would be, in an alternating fashion, to minimize L with respect to the signal weights while holding the signal vectors fixed to their current value, and then minimize L with respect to the signal vectors while holding the signal weights fixed to their current value. Given initial estimates $\{c_{ik}^{(0)}\}$ and $\{f_{jk}^{(0)}\}$, this algorithm can be expressed mathematically as follows:

Step 1'  $c^{(n+1)} = \arg\min_{c \geq 0} L(c, f^{(n)})$

Step 2'  $f^{(n+1)} = \arg\min_{f \geq 0} L(c^{(n+1)}, f)$

Step 3'  Repeat Steps 1' and 2' for a fixed number of iterations or until some desired stopping criterion is met Here, Steps 1' and 2' imply that the resulting algorithm monotonically decreases the least-squares objective function $$L(c^{(n+1)}, f^{(n+1)}) \leq L(c^{(n)}, f^{(n)}) \text{ for all } n = 0, 1, 2, \ldots \quad (7)$$

Introduction to the MM Method

The minimizations problems in Steps 1' and 2' are difficult so an alternative approach is needed. In this section, the MM method is introduced: then, the following section demonstrates how the MM method can be used to develop an algorithm that, by construction, monotonically decreases the least-squares objective function, produces nonnegative estimates, and is straightforward to implement.

Consider a real valued function f with domain $D \in \mathbb{R}^n$ that is to be minimized. A real valued function g with domain $\{(x_1, x_2): x_1, x_2 \in D\}$ is said to majorize the function f if the following conditions hold for all $x, y \in D$:

$$g(x, y) \geq f(x) \text{ and} \quad (C1')$$

$$g(x, x) = f(x). \quad (C2')$$

MM algorithms are a viable approach provided a majorizing function can be found that is easier to minimize than the original objective function. Assuming that g is a suitable majorizing function for f, the corresponding MM algorithm is $$x^{(k+1)} = \arg\min_{x \in D} g(x, x^{(k)}) \quad (8)$$

It follows from (C1') and (C2') that the MM algorithm defined by (8) is monotonic $$f(x^{(k+1)}) \leq g(x^{(k+1)}, x^{(k)}) \leq g(x^{(k)}, x^{(k)}) = f(x^{(k)}). \quad (9)$$

Standard Least-Squares Algorithm

The following describes an MM algorithm for estimating signal vectors and signal weights that is equivalent to the least-squares algorithm of Lee and Seung.

In the discussion that follows, it will be convenient to define sets $D_c$ and $D_f$, where $D_c$ and $D_f$ are the set of non-negative vectors of dimension $IK \times 1$ and $JK \times 1$, respectively. Let $c^{(n)}$ and $f^{(n)}$ be the current estimates for the signal weights and signal vectors, respectively. Further, let q and r be certain majorizing functions that satisfy the following conditions for $x, y, c \in D_c$ and $s, t, f \in D_f$ be $$q(x, y, f) \geq L(x, f) \quad (C1)$$

$$q(x, x, f) = L(x, f) \quad (C2)$$

$$r(s, t, c) \geq L(c, s) \quad (C3)$$

$$r(x, x, c) = L(c, x). \quad (C4)$$

Using the idea behind equation (8), CLA put forth the following MM algorithm for minimizing the least-squares objective function L $$c^{(n+1)} = \arg\min_{c \geq 0} q(c, c^{(n)}, f^{(n)}) \quad (10)$$

$$f^{(n+1)} = \arg\min_{f \geq 0} r(f, f^{(n)}, c^{(n+1)}). \quad (11)$$

It is straightforward to show that least-squares objection function monotonically decreases with increasing iterations. First, from (C1) and equation (10) it follows, respectively that $$L(c^{(n+1)}, f^{(n)}) \leq q(c^{(n+1)}, c^{(n)}, f^{(n)}) \quad (12)$$

$$q(c^{(n+1)}, c^{(n)}, f^{(n)}) \leq q(c^{(n)}, c^{(n)}, f^{(n)}). \quad (13)$$

Similarly, from (C3) and equation (11) it follows, respectively, that $$L(c^{(n+1)}, f^{(n+1)}) \leq r(f^{(n+1)}, f^{(n)}, c^{(n+1)}) \quad (14)$$

$$r(f^{(n+1)}, f^{(n)}, c^{(n+1)}) \leq r(f^{(n)}, f^{(n)}, c^{(n+1)}). \quad (15)$$

Now, from (C2) and (C4) it follows, respectively, that $$q(c^{(n)}, c^{(n)}, f^{(n)}) = L(c^{(n)}, f^{(n)}) \quad (16)$$

$$r(f^{(n)}, f^{(n)}, c^{(n+1)}) = L(c^{(n+1)}, f^{(n)}). \quad (17)$$

Consequently, we can conclude from equations (12)-(17) that $$L(c^{(n+1)}, f^{(n+1)}) \leq L(c^{(n)}, f^{(n)}). \quad (18)$$

At this point, all that remains is to determine the majorizing functions q and r. From equation (4), the least-squares objection function can be written as $$L(c, f) = \sum_{i=1}^{L} \sum_{j=0}^{J-1} \left[ a_{ij}^2 - 2a_{ij} \sum_{k=1}^{K} c_{ik} f_{jk} + \left( \sum_{k=1}^{K} c_{ik} f_{jk} \right)^2 \right]. \quad (19)$$

Using a known approach, the convexity of the square function is exploited to obtain the following inequality:

$$\left( \sum_{k=1}^{K} c_{ik} f_{jk} \right)^2 = \left\{ \sum_{k=1}^{K} \frac{c_{ik}^{(n)} f_{jk}}{\left[ \sum_{k'=1}^{K'} c_{ik'}^{(n)} f_{jk'} \right]} \left[ \frac{\left[ \sum_{k'=1}^{K'} c_{ik'}^{(n)} f_{jk'} \right] c_{ik}}{c_{ik}^{(n)}} \right]^2 \right\} \quad (20)$$

-continued $$\leq \sum_{k=1}^{K} \frac{c_{ik}^{(n)} f_{jk}}{\left[\sum_{k'=1}^{K'} c_{ik'}^{(n)} f_{jk'}\right]} \left(\frac{\left[\sum_{k'=1}^{K'} c_{ik'}^{(n)} f_{jk'}\right] c_{ik}}{c_{ik}^{(n)}}\right)^2 \quad (21)$$

$$\leq \hat{a}_{ij}(c^{(n)}, f) \sum_{k=1}^{K} \left(\frac{c_{ik}^2}{c_{ik}^{(n)}} f_{jk}\right), \quad (22)$$

where $c^{(n)} \in D_c$, $f \in D_f$, and $$\hat{a}_{ij}(c, f) \triangleq \sum_{k=1}^{K} c_{ik} f_{jk}. \quad (23)$$

It should be noted that (20) is a convex combination with weights $w_{ijk} \triangleq c_{ik}^{(n)} f_{jk} [\sum_{k'=1}^{K} c_{ik'}^{(n)} f_{jk'}]^{-1}$, where $w_{ijk} \geq 0$ and $\sum_{k=1}^{K} w_{ijk} = 1$ for all i, j. Replacing the $(\sum_{k=1}^{K} c_{ik} f_{jk})^2$ term in (19) by the right hand side of (22), we get the following majorizing function for L $$q(c, c^{(n)}, f) \triangleq \quad (24)$$

$$\sum_{i=1}^{I} \sum_{j=0}^{J-1} \left\{ a_{ij}^2 - 2a_{ij} \sum_{k=1}^{K} c_{ik} f_{jk} + \hat{a}_{ij}(c^{(n)}, f) \sum_{k=1}^{K} \left(\frac{c_{ik}^2}{c_{ik}^{(n)}} f_{jk}\right) \right\},$$

where, by construction, $q(c, c^{(n)}, f) \geq L(c, f)$ and $q(c, c, f) = L(c, f)$ for all $c, c^{(n)} \in D_c$ and $f \in D_f$.

By repeating the steps used to derive equation (24) with the roles of c and f switched, the majorizing function $$r(f, f^{(n)}, c) \triangleq \quad (25)$$

$$\sum_{i=1}^{I} \sum_{j=0}^{J-1} \left\{ a_{ij}^2 - 2a_{ij} \sum_{k=1}^{K} c_{ik} f_{jk} + \hat{a}_{ij}(c, f^{(n)}) \sum_{k=1}^{K} \left(\frac{f_{jk}^2}{f_{jk}^{(n)}} c_{jk}\right) \right\},$$

which satisfies the properties $r(f, f^{(n)}, c) \geq L(c, f)$ and $r(f, f, c) = L(c, f)$ for all $c \in D_c$ and $f, f^{(n)} \in D_f$.

To determine updates defined in equations (10) and (11), the partial derivatives of $q(c, c^{(n)}, f^{(n)})$ and $r(f, f^{(n)}, c^{(n+1)})$ are computed with respect to c and f, respectively, with the corresponding equations set to zero. It is straightforward to show that the derivatives are given by $$\frac{\partial q(c, c^{(n)}, f^{(n)})}{\partial c_{i'k'}} = \sum_{j=0}^{J-1} \left[ -2a_{i'j} f_{jk'}^{(n)} + 2\frac{c_{i'k'}}{c_{i'k'}^{(n)}} f_{jk'}^{(n)} \hat{a}_{ij}(c^{(n)}, f^{(n)}) \right] \quad (26)$$

$$\frac{\partial r(f, f^{(n)}, c^{(n+1)})}{\partial f_{j'k'}} = \quad (27)$$

$$\sum_{i=1}^{I} \left[ -2a_{ij'} c_{ik'}^{(n+1)} + 2\frac{f_{j'k'}}{f_{j'k'}^{(n)}} c_{ik'}^{(n+1)} \hat{a}_{ij}(c^{(n+1)}, f^{(n)}) \right].$$

Setting the derivatives in equations (26) and (27) to zero leads to the following least-squares algorithm for estimating the signal weights and signal vectors:

$$c_{ik}^{(n+1)} = c_{ik}^{(n)} \frac{\sum_{j=0}^{J-1} f_{jk}^{(n)} a_{ij}}{\sum_{j=0}^{J-1} f_{jk}^{(n)} \hat{a}_{ij}(c^{(n)}, f^{(n)})}, \quad (28)$$

$i = 1, 2, \ldots, I, k = 1, 2, \ldots, K$ $$f_{jk}^{(n+1)} = f_{jk}^{(n)} \frac{\sum_{i=0}^{I-1} c_{ik}^{(n+1)} a_{ij}}{\sum_{i=0}^{I-1} c_{ik}^{(n)} \hat{a}_{ij}(c^{(n+1)}, f^{(n)})}, \quad (29)$$

$j = 0, 1, 2, \ldots, I, k = 1, 2, \ldots, K.$

As shown above, the starting point for developing the proposed MM algorithm was equations (10) and (11). Alternatively, an MM algorithm can be developed by updating the signal vectors first and then the signal weights:

$$f^{(n+1)} = \underset{f \geq 0}{\mathrm{argmin}}\, r(f, f^{(n)}, c^{(n)}) \quad (30)$$

$$c^{(n+1)} = \underset{c \geq 0}{\mathrm{argmin}}\, q(c, c^{(n)}, f^{(n+1)}). \quad (31)$$

In this case, the resulting MM algorithm is $$f_{jk}^{(n+1)} = f_{jk}^{(n)} \frac{\sum_{i=1}^{I} c_{ik}^{(n)} a_{ij}}{\sum_{i=1}^{I} c_{ik}^{(n)} \hat{a}_{ij}(c^{(n)}, f^{(n)})}, \quad j = \quad (32)$$

$0, 1, 2, \ldots, J-1, k = 1, 2, \ldots, K$ $$c_{ik}^{(n+1)} = c_{ik}^{(n)} \frac{\sum_{j=0}^{J-1} f_{jk}^{(n+1)} a_{ij}}{\sum_{j=0}^{J-1} f_{jk}^{(n+1)} \hat{a}_{ij}(c^{(n)}, f^{(n+1)})}, \quad i = \quad (33)$$

$1, 2, \ldots, I, k = 1, 2, \ldots, K.$

Additive Least-Squares Algorithm

The standard least-squares algorithm defined by equations (28) and (29) (see also (32) and (33)) is referred to as a multiplicative algorithm. In this section, we derive an additive algorithm by developing an alternative majorizing function for the least-squares objective function L.

Exploiting the convexity of the square function we obtain the following inequality $$\left(\sum_{k=1}^{K} c_{ik} f_{jk}\right)^2 = \left[\sum_{k=1}^{K} \frac{f_{jk}}{\bar{f}_j} (\bar{f}_j c_{ik} - \bar{f}_j c_{ik}^{(n)} + \hat{a}_{ij}(c^{(n)}, f))\right]^2 \quad (34)$$

$$\leq \sum_{k=1}^{K} \frac{f_{jk}}{\bar{f}_j} (\bar{f}_j c_{ik} - \bar{f}_j c_{ik}^{(n)} + \hat{a}_{ij}(c^{(n)}, f))^2 \quad (35)$$

where $\bar{f}_j \triangleq \sum_{k=1}^{K} f_{jk}$, $c^{(n)} \in D_c$, and $f \in D_f$. It should be noted that (34) is a convex combination with weights $w_{jk} \triangleq f_{jk}/\bar{f}_j$, where $w_{jk} \geq 0$ for all j,k and $\Sigma_{k=1}^{K} w_{jk}=1$ for all j. Replacing the $(\Sigma_{k=1}^{K} c_{ik}f_{jk})^2$ term in (19) by the right hand side of (35), we get the following majorizing function for L $$q_A(c, c^{(n)}, f) \triangleq \sum_{i=1}^{I} \sum_{j=0}^{J-1} \left\{ a_{ij}^2 - 2a_{ij} \sum_{k=1}^{K} c_{ik} f_{jk} + \sum_{k=1}^{K} \frac{f_{jk}^2}{\overline{f}_{jk}^{(n)}} (\overline{f}_j c_{ik} - \overline{f}_j c_{ik}^{(n)} + \hat{a}_{ij}(c^{(n)}, f))^2 \right\}, \quad (36)$$

where, by construction, $q_A(c, c^{(n)}, f) \geq L(c, f)$ and $q_A(c, c, f) = L(c, f)$ for all $c, c^{(n)} \in D_c$ and $f \in D_f$.

When the steps used to derive equation (24) are repeated with the roles of c and f switched, we get the following majorizing function:

$$r_A(f, f^{(n)}, c) \triangleq \sum_{i=1}^{I} \sum_{j=0}^{J-1} \left\{ a_{ij}^2 - 2a_{ij} \sum_{k=1}^{K} c_{ik} f_{jk} + \sum_{k=1}^{K} \frac{c_{ik}}{\overline{c}_i} (\overline{c}_i f_{jk} - \overline{c}_i f_{jk}^{(n)} + \hat{a}_{ij}(c, f^{(n)}))^2 \right\}, \quad (37)$$

which satisfies the properties, $r_A(f, f^{(n)}, c) \geq L(c, f)$ and $r_A(f, f, c) = L(c, f)$ for all $c \in D_c$ and $f, f^{(n)} \in D_f$.

The updates defined by equations (10) and (11) are determined with q and r replaced by $q_A$ and $r_A$, respectively. Specifically, the partial derivatives of $q_A(c, c^{(n)}, f^{(n)})$ and $r_A(f, f^{(n)}, c^{(n+1)})$ are computed with respect to c and f, respectively, and then the resulting equations are set to zero. The desired derivatives can be given by $$\frac{\partial q_A(c, c^{(n)}, f^{(n)})}{\partial c_{i,k}} = -2 \sum_{j=0}^{J-1} a_{i,j} f_{jk'}^{(n)} + 2 \sum_{j=0}^{J-1} \frac{f_{jk'}^{(n)}}{\overline{f}_j^{(n)}} [\overline{f}_j^{(n)} c_{i,k}, -\overline{f}_j^{(n)} c_{i'k'}^{(n)} + \hat{a}_{i,j}(c^{(n)}, f^{(n)})] \overline{f}_j^{(n)} \quad (38)$$

$$\frac{\partial r_A(f, f^{(n)}, c^{(n+1)})}{\partial f_{i,k}} = -2 \sum_{i=0}^{I} a_{i,j} f_{jk'}^{(n+1)} + 2 \sum_{i=0}^{i-1} \frac{c_{ik'}^{(n+1)}}{\overline{c}_i^{(n+1)}} [\overline{c}_i^{(n+1)} f_{j,k}, -\overline{c}_i^{(n+1)} f_{j'k'}^{(n)} + \hat{a}_{ij}, (c^{(n+1)}, f^{(n)})] \overline{c}_i^{(n+1)} \quad (39)$$

Setting the derivatives in equations (38) and (39) to zero leads to the following additive least-squares algorithm for estimating the signal weights and signal vectors $$c_{ik}^{(n+1)} = \left[ c_{ik}^{(n)} + \frac{\sum_{j=0}^{J-1} f_{jk}^{(n)} [a_{ij} - \hat{a}_{ij}(c^{(n)}, f^{(n)})]}{\sum_{j=0}^{J-1} f_{jk}^{(n)} \overline{f}_j^{(n)}} \right]_+, \quad i = 1, 2, \ldots, I, k = 1, 2, \ldots, K \quad (40)$$

$$f_{jk}^{(n+1)} = \left[ f_{jk}^{(n)} + \frac{\sum_{i=1}^{i} c_{jk}^{(n+1)} [a_{ij} - \hat{a}_{ij}(c^{(n+1)}, f^{(n)})]}{\sum_{j=0}^{J-1} c_{ik}^{(n+1)} \overline{c}_i^{(n+1)}} \right]_+, \quad j = 0, 1, \ldots, J-1, k = 1, 2, \ldots, K, \quad (41)$$

where $[x]_+ \triangleq \max(0, x)$. Now, when the signal vectors are updated first and then the signal weights, the corresponding additive least-squares algorithm is given by $$f_{jk}^{(n+1)} = \left[ f_{jk}^{(n)} + \frac{\sum_{i=1}^{J} c_{ik}^{(n)} [a_{ij} - \hat{a}_{ij}(c^{(n)}, f^{(n)})]}{\sum_{i=1}^{I} c_{ik}^{(n)} \overline{c}_i^{(n)}} \right]_+, \quad j = 0, 1, \ldots, J-1, k = 1, 2, \ldots, K, \quad (42)$$

$$c_{ik}^{(n+1)} = \left[ c_{ik}^{(n)} + \frac{\sum_{j=0}^{J-1} f_{jk}^{(n+1)} [a_{ij} - \hat{a}_{ij}(c^{(n)}, f^{(n+1)})]}{\sum_{j=0}^{J-1} f_{jk}^{(n+1)} \overline{f}_j^{(n+1)}} \right]_+, \quad i = 1, 2, \ldots, I, k = 1, 2, \ldots, K. \quad (43)$$

Extensions of Standard Least-Squares Algorithm: Application to Myocardial Blood Flow Estimation Using Positron Emission Tomography In this section, the standard least-squares algorithm application to the problem of estimating absolute myocardial blow (MBF) noninvasively using positron emission tomography is addressed. Then, extensions of the standard least-squares algorithm are presented that lead to improved MBF estimates. These extensions are also applicable to the additive least-squares algorithm.

To assess the heart of a patient, it is desirable to estimate the patient's MBF noninvasively. One way to obtain this information is to first perform a dynamic PET scan of the patient's heart and then apply estimation algorithms that are based on equation (2) and other available models for dynamic cardiac PET data. Note, in the PET literature, the terms factor curves and factor weights are used for the terms signal vectors and signal weights. For PET based MBF estimation, the least-squares algorithm in equations (28) and (29) could first be used to estimate the factor curves and weights for a given dynamic PET data set. Then, using the resulting estimates, standard methods could be used to estimate the absolute myocardial blood flow of the patient. The accuracy of the MBF estimates would greatly depend on the performance of the standard least-squares algorithm, which, as mentioned previously, is highly dependent on the initial estimates. Therefore, we develop extensions of the least-squares method that greatly reduce the parameter space by incorporating a priori information. In practice, the proposed algorithms are expected to be more stable and produce more accurate estimates of the factor curves and weights than the standard least-squares algorithm. Therefore, improved MBF estimation is anticipated when the proposed algorithms are used instead of the standard least-squares algorithm.

Model

Let $a_i(t)$ denote the continuous-time activity in voxel i at time t, where $t \in [0, T]$ and T is the duration of the scan. In practice, only samples of the data are available so $a_{ij}$ denotes the activity in voxel i at time $t=jT_s$ (i.e., time frame j)

$$a_{ij} \triangleq a_i(jT_s), i=1,2,\ldots,I, j=0,1,2,\ldots,J-1 \quad (44)$$

where $T_s$ is the sampling interval, I is the number of voxels, and J is the number of time frames. Referring to equation (2), it is typically assumed that the activity $a_{ij}$ is a linear combination of K=3 unknown factor curves representing the sampled right ventricular blood pool, left ventricular blood pool, and myocardial tissue curves, respectively. Note, the factor weights for a particular time frame can be viewed as an image and therefore are collectively referred to as a factor image.

Physiological Based Constraints: Right and Left Ventricle Tissue Curves go to Zero Due to the physiology of the heart and half-life of the radiopharmaceuticals used in nuclear cardiology, the factor curves for the right and left ventricles go to zero as t approaches 0, which a priori information is incorporated into the estimation problem. Thus, an alternative to the least-squares formulation is to add a penalty term to the least-squares objective function that "forces" the factor curves for the right ventricle $f_1 \triangleq [f_{11}, f_{21}, \ldots, f_{J1}]$ and left ventricle $f_2 \triangleq [f_{12}, f_{22}, \ldots, f_{J2}]$ to go to zero. Given its potential advantage over the standard least-squares method, we propose the following penalized least-squares method $$(\bar{c}, \hat{f}) = \arg \min_{c \geq 0, f \geq 0} L(c, f) + \beta_1 \Lambda(f_1) + \beta_2 \Lambda(f_2), \tag{45}$$

where the penalty parameters $\beta_1$ and $\beta_2$ control the degree of influence of the penalty terms $\Lambda(f_1)$ and $\Lambda(f_2)$, respectively. Although there are many possible choices for the penalty function $\Lambda$, in this approach the following function is used:

$$\overline{\Lambda}(g) = (\Sigma_{j > j_0}^{J-1} g_j)^2 \tag{46}$$

where g is a real J×1 vector. It can be seen that $\Lambda(g)$ is the energy of g after the user chosen time frame $j_0$.

The desired MM algorithm is obtained by setting the partial derivatives of $r(f, f^{(n)}, c^{(n+1)}) + \beta_1 \Lambda(f_1) + \beta_2 \Lambda(f_2)$ with respect to f to zero. For k=1, 2, the partial derivatives of the penalty function $\Lambda$ are $$\frac{\partial \Lambda(f_k)}{\partial f_{j',k'}} = \begin{cases} 2f_{j',k}, & j' > j_0, k' = k \\ 0, & \text{otherwise,} \end{cases} \tag{47}$$

Using this result and equation (27), the following iterative algorithm is derived for estimating the right and left ventricle tissue curves $$f_{jk}^{(n+1)} = f_{jk}^{(n)} \frac{\sum_{i=1}^{J} c_{ik}^{(n+1)} a_{ij}}{\sum_{i=1}^{I} c_{ik}^{(n+1)} \hat{a}_{ij}(c^{(n+1)}, f^{(n)}) + \beta_k f_{jk}^{(n)} I_S(j)}, j = 0, 1, 2, \ldots, J-1, k = 1, 2 \tag{48}$$

where I is the indicator function and S={j0+1, j0+2, . . . , J} (i.e., $I_s(j)=1$ for $j \in S$ and $I_s(j)=0$ for $j \ni S$). The updates for the factor weights and tissue curve (i.e., $f_3$) are given by equations (28) and (29), respectively. The proposed algorithm, refer to herein as the PLS algorithm, monotonically decreases the penalized least-squares (PLS) objective function in equation (45) and is guaranteed to produce nonnegative estimates for the values of the factor curves, f, and factor weights, c. It should be noted that the PLS algorithm provides least-squares estimates when $\beta_1 = \beta_2 = 0$. Also, the update for the factor weights is the same for both the LS and PLS algorithms.

Due to the nonnegativity of the factor curves for the right and left ventricles, another penalty function optionally can be used to account for the fact that they decrease for t sufficiently large is $$\overline{\Lambda}(g) = (\Sigma_{j > j_0}^{J-1} g_j)^2 \tag{49}$$

Also, with a small modification, the PLS framework can incorporate other known penalty functions.

Exploit Fact that Maximum of Right and Left Ventricle Tissue Curves can be Reliably Estimated When the radiopharmaceutical is administered to a patient, the physiology of the body is such that the activity shows up in the right ventricle first, then the left ventricle, and finally the myocardium. These delays are such that the maximum values of the right and left ventricles are essentially free of activity from the myocardium, despite the motion of the heart and point spread function of the PET system. Thus, an estimate of the maximum value of the right ventricle can be estimated by averaging the maximum values of TACs that lie in the central region of the right ventricle. In a similar way, an estimate of the maximum value of the left ventricle can be obtained. Methods are available that identify the voxels that lie in the right and left ventricles, and myocardium.

Let $\mu_1$ and $\mu_2$ represent the unknown maximum values of the right and left ventricles, respectively, and $j_1$ and $j_2$ denote the locations of the maximum values of the right and left ventricles. To incorporate knowledge of $\mu_1$ and $\mu_2$, we estimate the tissue factors using $$f^{(n+1)} = \arg \min r(f, f^{(n)}, c^{(n)}) \text{ subject to } f \geq 0, |f_{j_1 1} - \hat{\mu}_1| \leq \in, |f_{j_2 2} - \hat{\mu}_2| \leq \in, \tag{50}$$

where $\in$ is a tolerance parameter chosen by the user, and $\hat{\mu}_1$ and $\hat{\mu}_2$ are estimates of the maximum values $\mu_1$ and $\mu_2$.

The function $r(f, f^{(n)}, c^{(n)})$ is decoupled in the sense that there are no terms of the form $f_{jk} f_{j'k'}$, except when j=j' and k=k'. Thus, the solution to the optimization problem in equation (50) is straightforward and leads to the following update for the right and left ventricle tissue factors (i.e., k=1, 2):

$$f_{jk}^{(n+1)} = f_{jk}^{(n)} \frac{\sum_{i=1}^{I} c_{ik}^{(n+1)} a_{ij}}{\sum_{i=1}^{I} c_{ik}^{(n+1)} \hat{a}_{ij}(c^{(n+1)}, f^{(n)})}, \text{ for all } j \neq j_k, k = 1, 2 \tag{51}$$

$$f_{jk}^{(n+1)} = \left[ f_{jk}^{(n)} \frac{\sum_{i=1}^{I} c_{ik}^{(n+1)} a_{ij}}{\sum_{i=1}^{I} c_{ik}^{(n+1)} \hat{a}_{ij}(c^{(n+1)}, f^{(n)})} \right]_{\mu_k - c}^{\mu_k + c}, \text{ for } j = j_k, k = 1, 2 \tag{52}$$

where $$[a]_l^u \triangleq \begin{cases} a, & l \leq a \leq u \\ l, & a < l \\ u, & a > u \end{cases} \tag{53}$$

The updates for the factor weights and tissue curve are given by equations (28) and (29), respectively. Also, the denominator terms in equations (51) and (52) would be $\Sigma_{i=1}^{I} c_{ik}^{(n+1)} \hat{a}_{ij}(c^{(n+1)}, f^{(n)}) + \beta_k f_{jk}^{(n)} I_S(j)$ if we included the penalties on the right and left ventricle tissue curves that were discussed in the previous section.

Reduce Unknown Parameters Via a Suitable Model for Left Ventricle Tissue Curve

It has been postulated that the left ventricle tissue curve can be modeled as the convolution of the right ventricle tissue curve with a gamma function. Described below is an exploitation of this idea and development of an extension of the standard least-squares algorithm that has significantly fewer unknowns.

1) Model: Let r(t) and l(t) denote the unknown continuous-time tissue curves for the right and left ventricles, respectively. The left ventricle tissue curve is modeled as the convolution of the right tissue curve with a delayed, gamma function $\bar{h}_c(t)$ $$l(t) = r(t) * \bar{h}_c(t-\tau), \tag{54}$$

where "*" denotes the convolution operator $$\bar{h}_c(t) = a \frac{t^{m-1}}{(m-1)!} \exp(-bt) u(t) \quad (a > 0, b > 0, \text{ and } m = 1, 2, \ldots),$$

u(t) is the unit step function, and $\tau > 0$ is the delay. It should be noted that the delay is due to the fact that the radiopharmaceutical activity first appears in the right ventricle and then the left ventricle. From (54) it follows that $L(s) = R(s) \bar{H}_c(s) \exp(-s\tau)$, where $$\bar{H}_c(s) \triangleq \frac{a}{(s+b)^m}. \tag{55}$$

As noted previously, we let $f_{j1}$ and $F_{j2}$, $j=0, 1, 2, \ldots, J-1$ denoted the sampled right and left ventricle tissue curves. Where the scan durations for dynamic sequence PET protocols are not uniform, the assumption that the TACs are sampled uniformly is inappropriate. However, uniform samples of the TACs can be obtained from non-uniform samples of the TACs via a suitable interpolation. It is of interest to determine a discrete-time system with the property that its response to the right ventricle tissue curve $f_1$ closely approximates the left ventricle tissue curve $f_2$. The bilinear transformation is a popular way to transform a linear time-invariant continuous-time system into a linear time-invariant discrete-time system. A limitation of the bilinear transform is that a delay in a continuous-time system must be an integer multiple of the sampling interval. Assuming the delay $\tau$ is a multiple of the sampling interval Ts, the system function of the desired discrete time system, H(z), can be obtained by applying the bilinear transformation to the continuous-time system $H_c(s) = \bar{H}_c(s) \exp(-s\tau)^3$ $$H(z) = H_c(s) \Big|_{s=\frac{2}{T}\frac{1-z^{-2}}{1+z^{-1}}} \tag{56}$$

$$= a \left[ \frac{1}{(s+b)^m} \right]_{s=\frac{2}{T}\frac{1-z^{-2}}{1+z^{-1}}} z^{-d} \tag{57}$$

$$= g \left( \frac{1+z^{-1}}{1-pz^{-1}} \right)^m z^{-d}, \tag{58}$$

where $\tau = dT_s$ for some inter d, $g = a(2/T_s+b)^{-(m+1)}$, and $p=(2/T_s+b)^{-1}(2/T_s-b)$ (note: $h_c(t) \triangleq \bar{h}_c(t-\tau)$).

Let hj(θ) denote the inverse z-transform of H(z), using a notation that illustrates its dependence on the parameters θ=(g, p, m, d). Then, the assumed relationship between the sampled right ventricle and left ventricle tissue curves can be written as $$f_{j2} = f_{j1} * h_j(\theta) = \sum_{s=0}^{J-1} f_{s1} h_{j-s}(\theta) \tag{59}$$

where, for simplicity, our notation for $f_{j2}$ does not account for its dependence on θ. Moreover, the corresponding least-squares objective function, $L_\theta$, has the same form as L (see equation (4))

$$L_\theta(c, f_1, f_3, \theta) = \sum_{i=1}^{I} \sum_{j=0}^{J-1} \left( a_{ij} - \sum_{k=1}^{K} c_{ik} f_{jk} \right)^2, \tag{60}$$

except it depends on θ because $f_{j2} = f_{j1} * h_j(\theta)$. To insure that $h_j(\theta)$ is a nonnegative function, the following feasible set for θ is chosen:

$$D_\theta \triangleq \{g, p, m, d: g \geq 0, 0 \leq p \leq 1, m = 0, 1, 2, \ldots, \\ d = 0, 1, 2, \ldots \}. \tag{61}$$

Hence, for $\theta \in D_\theta$, $f_{j2}$ is a nonnegative function provided $f_{j1}$ is a nonnegative function.

Convolution Least-Squares Algorithm

Given the similarity of $L_\theta$ and L, it follows that the corresponding majorizing functions for $L_\theta$ are $$q_\theta(c, c^{(n)}, f_1, f_3, \theta) \triangleq \tag{62}$$
$$\sum_{i=1}^{I} \sum_{j=0}^{J-1} \left\{ a_{ij}^2 - 2a_{ij} \sum_{k=1}^{K} c_{ik} f_{jk} + \hat{a}_{ij}(c^{(n)}, f) \sum_{k=1}^{K} \frac{c_{ik}^2}{c_{ik}^{(n)}} f_{jk} \right\}$$

$$r_\theta(f_1, f_3, f_1^{(n)}, f_3^{(n)}, c, \theta) \triangleq \tag{63}$$
$$\sum_{i=1}^{I} \sum_{j=0}^{J-1} \left\{ a_{ij}^2 - 2a_{ij} \sum_{k=1}^{K} c_{ik} f_{jk} + \hat{a}_{ij}(c, f^{(n)}) \sum_{k=1}^{K} \frac{f_{jk}^2}{f_{jk}^{(n)}} c_{ik} \right\}$$

where, again, fj2=fj1*hj(θ). By construction, for all c, $c^{(n)} \in D_c$, $f_1, f_3 \geq 0$, and $\theta \in D_\theta$, $$q_\theta(c, c^{(n)}, f_1, f_3, \theta) \geq L_\theta(c, f_1, f_3, \theta) \tag{64}$$

$$q_\theta(c, c, f_1, f_3, \theta) = L_\theta(c, f_1, f_3, \theta) \tag{65}$$

$$r_\theta(f_1, f_3, f_1^{(n)}, f_3^{(n)}, c, \theta) \geq L_\theta(c, f_1, f_3, \theta) \tag{66}$$

$$r_\theta(f_1, f_3, f_1, f_3, c, \theta) = L_\theta(c, f_1, f_3, \theta) \tag{67}$$

Using the MM methodology, the updates for estimating the factor weights and tissue curves, given the current parameters estimates, are given by $$c^{(n+1)} = \operatorname*{argmin}_{c \geq 0} q_\theta(c, c^{(n)}, f_1^{(n)}, f_3^{(n)}, \theta^{(n)}) \tag{68}$$

$$(f_1^{(n+1)}, f_3^{(n+1)}) = \arg\min_{f_1, f_3 \geq 0} r_\theta(f_1, f_3, f_1^{(n)}, f_3^{(n)}, c^{(n+1)}, \theta^{(n)}) \tag{69}$$

$$\theta^{(n+1)} = \operatorname*{argmin}_{\theta \in D_\theta} L_\theta(c^{(n+1)}, f_1^{(n+1)}, f_3^{(n+1)}, \theta) \tag{70}$$

The optimization problem in equation (69) is not straightforward because the objective function in (69) has "cross terms" of the form $f_{j1} f_{j'1}$, $j \neq j'$. These cross terms are due to the $f_{j2}^2$ term in equation (63). Thus, it will be beneficial to construct a majorizing function for $f_{j2}^2$. It is straightforward to show that the steps used to derive the inequality in equation (22) can be repeated to get the following inequality $$f_{j2}^2 \leq \upsilon(f_1, f_1^{(n)}, \theta) \triangleq \left[\sum_{s'=0}^{J-1} f_{s'1}^{(n)} h_{j-s'}(\theta)\right] \sum_{s=0}^{J-1} h_{j-s}(\theta) \frac{f_{s1}^2}{f_{s1}^{(n)}}, \quad (71)$$

which has the property that $\upsilon(f_1, f_1, \theta) = f_{j2}^2$ for all $f_1 \geq 0$ and $\theta \in D_\theta$. Now, equation (71) is substituted into equation (63) to get a majorizing function that satisfies equations (66) and (67) and can be easily minimized with respect to $f_1$ $$\bar{r}_\theta(f_1, f_3, f_1^{(n)}, f_3^{(n)}, c, \theta) \quad (72)$$

$$\triangleq \sum_{i=1}^{I} \sum_{j=0}^{J-1} \left\{ a_{ij}^2 - 2a_{ij} \sum_{k=1}^{K} c_{ik} f_{jk} + \right. \quad (73)$$

$$\left. \hat{a}_{ij}(c, f^{(n)}) \left( c_{i1} \frac{f_{j1}^2}{f_{j1}^{(n)}} + c_{i1} \sum_{s=0}^{J-1} h_{j-s}(\theta) \frac{f_{s1}^2}{f_{s1}^{(n)}} + c_{i3} \frac{f_{j3}^2}{f_{j3}^{(n)}} \right) \right\},$$

where $$f_{j2}^{(n)} = f_{j1}^{(n)} * h_j(\theta^{(n)}) = \sum_{s=0}^{J-1} f_{s1}^{(n)} h_{j-s}(\theta^{(n)}) \quad (74)$$

Comparing equations (24) with (62), and (25) with (63), it is evident that the update for the factor weights c (see equation (68)) and the third factor curve $f_3$ (see equation (69)) are given by equations (28) and (29), respectively, except that now $f_{j2}^{(n)}$ is given by equation (74). In order to get the update for the right ventricle $f_1$ (see equation (69)), we take the partial derivative of $\bar{r}_\theta((f_1, f_3, f_1^{(n)}, f_3^{(n)}, c^{(n+1)}, \theta^{(n)})$ with respect to $f_1$ and set the result to zero. From straightforward calculations, the derivative of $\bar{r}_\theta((f_1, f_3, f_1^{(n)}, f_3^{(n)}, c^{(n+1)}, \theta^{(n)})$ with respect to $f_{j'1}$ is $$\frac{\partial \bar{r}_\theta(f_1, f_3, f_1^{(n)}, f_3^{(n)}, c^{(n+1)}, \theta^{(n)})}{\partial f_{j'1}} = -2 \sum_{i=1}^{I} \sum_{j=0}^{J-1} c_{i1} a_{ij'} - \quad (75)$$

$$2 \sum_{i=1}^{I} \sum_{j=0}^{J-1} c_{i2} a_{ij} h_{j-j'}(\theta^{(n)}) + 2 \frac{f_{j'1}}{f_{j'1}^{(n)}} \sum_{i=1}^{I} c_{i1} \hat{a}_{ij'}(c^{(n+1)}, f^{(n)}) +$$

$$2 \frac{f_{j'1}}{f_{j'1}^{(n)}} \sum_{i=1}^{I} \sum_{j=0}^{J-1} c_{i2} \hat{a}_{ij'}(c^{(n+1)}, f^{(n)}) h_{j-j'}(\theta^{(n)})$$

$$= -2 \sum_{i=1}^{I} c_{i1} \hat{a}_{ij} - 2 \sum_{i=1}^{I} c_{i2} [a_{ij} * h_{-j}(\theta^{(n)})] + \quad (76)$$

$$2 \frac{f_{j'1}}{f_{j'1}^{(n)}} \sum_{i=1}^{I} c_{i1} \hat{a}_{ij'}(c^{(n+1)}, f^{(n)}) +$$

$$2 \frac{f_{j'1}}{f_{j'1}^{(n)}} \sum_{i=1}^{I} c_{i2} [\hat{a}_{ij'}(c^{(n+1)}, f^{(n)}) * h_{-j'}(\theta^{(n)})].$$

Now, equation (76) is set to zero to get the desired update for the right ventricle tissue curve, which is $$f_{j1}^{(n+1)} = f_{j1}^{(n)} \frac{\sum_{i=1}^{I} c_{i1} a_{ij} + \sum_{i=1}^{I} c_{i2} [a_{ij} * h_{-j}(\theta^{(n)})]}{\sum_{i=1}^{I} c_{i1} \hat{a}_{ij}\left(\begin{array}{c} c^{(n+1)}, \\ f^{(n)} \end{array}\right) + \sum_{i=1}^{I} c_{i2} \left[\hat{a}_{ij}\left(\begin{array}{c} c^{(n+1)}, \\ f^{(n)} \end{array}\right) * h_{-j}(\theta^{(n)})\right]}, \quad j \quad (77)$$

$$= 0, 1, \ldots, J-1.$$

When knowledge about the maximum value of the right ventricle tissue curve is incorporated, as well as the penalty function $\Lambda$, then the update for the right ventricle tissue curve is $$f_{j1}^{(n+1)} = \left[ f_{j1}^{(n)} \frac{\sum_{i=1}^{I} c_{i1} a_{ij} + \sum_{i=1}^{I} c_{i2} [a_{ij} * h_{-j}(\theta^{(n)})]}{\sum_{i=1}^{I} c_{i1} \hat{a}_{ij}\left(\begin{array}{c} c^{(n+1)}, \\ f^{(n)} \end{array}\right) + \sum_{i} c_{i2} \left[\hat{a}_{ij}\left(\begin{array}{c} c^{(n+1)}, \\ f^{(n)} \end{array}\right) * h_{-j}(\theta^{(n)})\right]} \right]_{\mu_k - \epsilon}^{\mu_k + \epsilon}, j \quad (78)$$

$$= 0, 1, \ldots, J-1.$$

With the update for the right ventricle curve in hand (i.e., update in equations (77) or (78)), the algorithm for minimizing the least-squares function $L_\theta$, is proposed, which is referred to herein as the convolution least-squares (CLA) algorithm. First, let $d_{min}$ and $d_{max}$ denote the minimum and maximum delay considered, respectively, and $m_{max}$ denote the maximum value considered for the parameter m. The CLA algorithm follows:

get initial estimates: $f_1^{(0)}$, $f_3^{(0)}$, $g^{(0)}$, and $p^{(0)}$
for $\hat{d} = d_{min}, d_{min} + 1, \ldots, d_{max}$,
  for $\hat{m} = 1, 2, \ldots, m_{max}$,
    for n=0,1,2, . . .
      let $\theta^{(n)} = [g^{(n)} \ p^{(n)} \ \hat{m} \ \hat{d}]$
      get $c^{(n+1)}$ using (28) with $f_{j2}^{(n)}$ given by (74)
      get $f_1^{(n+1)}$ using (77)
      get $f_3^{(n+1)}$ using (29) with $f_{j2}^{(n)}$ given by (74)

$$(g^{(n+1)}, p^{(n+1)}) = \arg\min_{\theta \geq 0, 0 \leq p \leq 1} L_\theta(c^{(n+1)}, f_1^{(n+1)}, f_3^{(n+1)}, g, p, \hat{m}, \hat{d}) \quad (79)$$

end
    store current parameter estimates and corresponding value for $L_\theta$
  end
end The desired parameter estimates are the estimates from the CLA algorithm that produce the smallest least-squares error. It should be noted that the objective function $L_\theta$ decreases monotonically with increasing iterations.

The problem in equation (79) can be solved using the following iterative coordinate descent method. It will be convenient to express $h_j(\theta)$ as $h_j(\theta) = g\bar{h}_j(p, m, d)$, where $\bar{h}_j(p, m, d)$ is the inverse Z-transform of $$\bar{H}(z) = \left(\frac{1 + z^{-1}}{1 - pz^{-1}}\right)^m z^{-d}. \quad (80)$$

With this notation, the objective function in (79) can be written as $$L_\theta(c^{(n+1)}, f_1^{(n+1)}, f_3^{(n+1)}, g, p, m, \hat{d}) = \alpha^{(n+1)}g^2 - 2\beta^{(n+1)}g + \gamma^{(n+1)}, \quad (81)$$

where $$\alpha^{(n+1)}(c^{(n+1)}, f_1^{(n+1)}, f_3^{(n+1)}) \triangleq \quad (82)$$

$$\sum_{i=1}^{I} \sum_{j=0}^{J-1} [a_{ij} - (c_{i1}^{(n+1)} f_{j1}^{(n+1)} + c_{i3}^{(n+1)} f_{j3}^{(n+1)})]$$

$$\beta^{(n+1)}(c^{(n+1)}, f_1^{(n+1)}, f_3^{(n+1)}, p, \hat{m}, \hat{d})$$

$$\triangleq \sum_{i=1}^{I} \sum_{j=0}^{J-1} [a_{ij} - (c_{i1}^{(n+1)} f_{j1}^{(n+1)} + c_{i3}^{(n+1)} f_{j3}^{(n+1)})] \times \quad (83)$$

$$c_{i2}^{(n+1)}(f_{j1}^{(n+1)} * \hat{h}_j(\hat{p}, \hat{m}, \hat{d}))$$

$$\gamma^{(n+1)}(c^{(n+1)}, f_1^{(n+1)}, f_3^{(n+1)}, p, \hat{m}, \hat{d}) \triangleq \quad (84)$$

$$\sum_{i=1}^{I} \sum_{j=0}^{J-1} [c_{i2}^{(n+1)}(f_{j1}^{(n+1)} * \hat{h}_j(\hat{p}, \hat{m}, \hat{d}))]^2.$$

Thus, the unconstrained minimizer of $L_\theta(c^{(n+1)}, f_1^{(n+1)}, f_3^{(n+1)}, g, \hat{p}, \hat{m}, \hat{d})$ with respect to g is simply $$\hat{g} = \frac{\beta^{(n+1)}(c^{(n+1)}, f_1^{(n+1)}, f_3^{(n+1)}, \hat{p}, \hat{m}, \hat{d})}{\alpha^{(n+1)}(c^{(n+1)}, f_1^{(n+1)}, f_3^{(n+1)}, \hat{p}, \hat{m}, \hat{d})}, \quad (84)$$

where $\hat{p}$ denotes the current estimate for the filter parameter p. With the above result, the steps for solving the optimization problem of equation (79) is given using the coordinate descent method: Let $p^{old} = p^{(n)}$ and $[x]_+ = \max(0, x)$ IC Step 1:

$$g^{new} = \arg\min_{g \geq 0} L_\theta(c^{(n+1)}, f_1^{(n+1)}, f_3^{(n+1)}, p^{old}, \hat{m}, \hat{d}) \quad (84)$$

$$= \left[\frac{\beta^{(n+1)}(c^{(n+1)}, f_1^{(n+1)}, f_3^{(n+1)}, p^{old}, \hat{m}, \hat{d})}{\alpha^{(n+1)}(c^{(n+1)}, f_1^{(n+1)}, f_3^{(n+1)}, p^{old}, \hat{m}, \hat{d})}\right]_+, \quad (87)$$

IC Step 2: Using a 1D line search, such as the golden section method [17], get $p^{new}$:

$$p^{new} = \arg\min_{0 \leq p \leq 1} L_\theta(c^{(n+1)}, f_1^{(n+1)}, f_3^{(n+1)}, g^{new}, p, \hat{m}, \hat{d}) \quad (88)$$

IC Step 3: Set $p^{old} = p^{new}$ and repeat the above two steps, for a set number of iterations or until some desired stopping criterion is met.

IC Step 4: Set $g^{(n+1)} = g^{new}$ and $p^{(n+1)} = p^{new}$.

So configured, the CLA algorithm is monotonic and guaranteed to produce nonnegative estimates.

Initialization

User-dependent and user-independent methods are available for determining initial estimates for the right and left ventricle tissues curves, and myocardial tissue curve. The initial factor weights are typically chosen to be uniform in the sense that $c_{ik} = 1/3$ for all i, k. Regarding the range of values for the delay, suitable values for the minimum and maximum delay between the right and left ventricle tissue curves are available from the literature in human physiology.

It is expected that a suitable maximum value for the filter order, $m_{max}$, can be determined through experiments. Consequently, the following addresses computing initial estimates for the filter parameters g and p.

Because $F_2(z) = H(z) F_1(z)$ from equation (59), it follows that $F_2^{(0)}(z) \approx H(z) F_1^{(0)}(z)$, where $f_{1j}^{(0)}$ and $f_{2j}^{(0)}$ denote the initial right and left ventricle tissue curves, and H(z) is given by equation (58). Therefore, $$F_2^{(0)}(z) \approx H(z) F_1^{(0)}(z) \quad (89)$$

$$F_2^{(0)}(z) \approx g \left(\frac{1 + z^{-1}}{1 - pz^{-1}}\right)^m z^{-d} F_1^{(0)}(z) \quad (90)$$

$$F_2^{(0)}(z) \approx g \frac{1}{(1 - pz^{-1})^m} z^{-d} \overline{F}_1^{(0)}(z) \quad (91)$$

where $$\overline{F}_1^{(0)}(z) = F_1^{(0)}(z)(1 + z^{-1})^m z^{-d}. \quad (92)$$

Thus, the initial left ventricle tissue curve is assumed to be approximately equal to the response of a certain mth-order, all-pole filter to the initial right ventricle tissue curve. This observation and equation (91) forms the basis of the following method for obtaining initial estimates for g and p:

--- for $\hat{d} = d_{min}, d_{min} + 1, \ldots, d_{max}$,
  for $m = 1, 2, \ldots, m_{max}$,
    Initial g, p - Step 1: Using an input-output system identification method, such as the Steiglitz-McBride algorithm, find the parameters $b_0$, $a_1, a_2, \ldots, a_m$ that provide the best least-squares fit for the following model:

$$F_2^{(0)}(z) = b_0 \frac{1}{(1 + a_1 z^{-1} + a_2 z^{-2} + \ldots + a_m z^{-m})} \overline{F}_1^{(0)}(z) \quad (93)$$

Initial g, p - Step 2: Let $\hat{b}_0, \hat{a}_1, \hat{a}_2, \ldots, \hat{a}_m$ be the resulting estimates for $b_0$, $a_1, a_2, \ldots, a_m$, respectively, from the first step. Comparing equations (91) and (93), an estimate for g is $\hat{g} = \hat{b}_0$. Moreover, an estimate for p can be obtained by determining the best least-squares fit between $(1 - pz^{-1})^m$ and $(1 + a_1 z^{-1} + a_2 z^{-2} + \ldots + a_m z^{-m})$. For Example, when m = 2, an estimate for p is:

$$\hat{p} = \arg\min_{0 \leq p \leq 1} (-2p - \hat{a}_1)^2 + (p^2 - \hat{a}_2)^2, \quad (94)$$

Initial g, p - Step 3: Store the current parameter estimates $\{\hat{g}, \hat{p}, \hat{m}, \hat{d}\}$ and the corresponding least-squares error $$(95)$$

$$L_{init}(\hat{g}, \hat{p}, \hat{m}, \hat{d}) \triangleq \sum_{j=0}^{J-1} (f_{j2}^{(0)} - \tilde{f}_{j1}^{(0)}(\hat{m}, \hat{d}) * \tilde{h}_j(\hat{g}, \hat{p}, \hat{m}))^2,$$

where $\tilde{f}_{j1}^{(0)}(\hat{m}, \hat{d})$ and $\tilde{h}_j(g, p, m)$ are, respectively, the inverse Z-transforms of $\overline{F}_1^{(0)}(z)$ (see (92)) and $$(96)$$

$$\tilde{H}(z) \triangleq g \frac{1}{(1 - pz^{-1})^m}.$$

end
end

---

The set of parameters that produce the smallest least-squares error are the desired initial estimates for the parameters g, p, m, and d, which we denote respectively as $g^{(0)}$, $p^{(0)}$, $m^{(0)}$, and $d^{(0)}$.

The initial estimates for the parameters m and d are not explicitly used in the CLA algorithm. However, they could be used to reduce the range of values considered for the parameters m and d. For example, the "for loop" for the delay in the CLA algorithm could be instead: for $\hat{d}=d^{(0)}-\Delta$: $d^{(0)}+\Delta$, where $\Delta>0$, would be an integer chosen by the user.

III. An Approach without Assumption of a Mathematical Relationship Between Right Ventricle and Left Ventricle Curves In a further approach to estimating MBF, we first incorporate the Hutchins pharmacological kinetic model into the standard FADS model in a way to not assume that the RV and LV tissue curves obey any particular mathematical relationship unlike the methods described above. The improved model, which we refer to as the second pharmacological kinetics based FADS (K-FADS-II) model, provides another way for estimating voxel dependent myocardium tissue curves that are physiologically meaningful. In our next step, we perform a discretization that transforms the continuous-time K-FADS-II model into a discrete-time K-FADS-II model. It should be noted that there is a simple relationship between the discrete-time and continuous-time K-FADS-II parameters. Lastly, we develop an algorithm, which we call the Improved Voxel-Resolution Myocardial Blood Flow (IV-MBF) algorithm that estimates the parameters of the discrete-time K-FADS-II model by iteratively minimizing a certain least-squares (LS) objective function. The desired MBF estimates are computed in a straightforward manner from the estimated discrete-time K-FADS-II model parameters. The IV-MBF algorithm was evaluated subjectively and objectively through experiments conducted using synthetic data and patient data, and found to be accurate and stable in the test scenarios we considered. Hence, we believe the proposed method is feasible for determining physiologically meaningful estimates of MBF.

To avoid confusion in view of the discussion above regarding other approaches, we start again from the fundamentals and restart the numbering of equations. The kinetic behavior of ammonia in the myocardium is modeled by the compartment model shown in FIG. 1 and the following differential equations (note: we assume $k_4=0$).

$$\frac{dC_F(t)}{dt} = k_1 C_P(t) - (k_2+k_3)C_F(t) \quad (1)$$

$$\frac{dC_T(t)}{dt} = k_3 C_F(t), \quad (2)$$

where $C_P$ is the ammonia concentration in blood plasma, $C_F$ is the concentration of the free (i.e., unbound) ammonia, and $C_T$ is the concentration of the trapped (i.e., bound) ammonia.

In the standard FADS model, it is assumed that $a_{ij}$, the activity in voxel i of frame j, is a linear combination of K primary factor curves $$a_{i,j} = \sum_{k=1}^{K} c_{ik} f_{kj} \quad (3)$$

where $\{f_{kj}\}$ are the values of the factor curves and the coefficients $\{c_{ik}\}$ are the factor weights. The primary factor curves for conventional MBF estimation applications are the right ventricle (RV), left ventricle (LV), and myocardial tissue curves, which model the ammonia concentration as a function of time in the RV, LV, and myocardium, respectively. The mathematical task is to find both the factor curves and weights so that the linear combination of factor curves for every voxel in the myocardium matches the corresponding measured time activity curve (TAC) as close as possible. This problem is constrained by requiring that the factor curves and weights all be nonnegative.

Other approaches include spillover correction because of the finite resolution of the scanner and because the myocardium is moving during the scan. In one known approach, factor analysis was used to obtain, in theory, spillover independent time activity curves of the RV, LV, and myocardial blood tissue. By using curves generated from factor analysis, the spillover component in the model can be eliminated in theory. However, it is noted that factor analysis does not correct for the under measurement due to the partial volume effect. Correcting errors due to the partial volume effect would require the use of a contrast recovery coefficient.

A. K-Fads-II Model

In this section, we first present a model that combines Hutchins' pharmacological kinetic model with the standard factor analysis model (see equation (3)). The resulting model is an improvement over an earlier version discussed above, so we call it the second pharmacological kinetics based FADS model (K-FADS-II). Next, we discuss a discretization that transforms the continuous-time K-FADS-II model into a discrete-time K-FADS-II model. Specifically, the discrete-time K-FADS-II model is obtained by applying the bilinear transform to the continuous-time K-FADS-II model. It should be noted that there is a simple relationship between the discrete-time and continuous-time K-FADS-II parameters.

1. Continuous-Time Model for Activity in the Myocardium

The unknown ammonia concentrations in the RV and LV (i.e., $C_P$) are assumed to be spatially independent, whereas the unknown concentrations of the free ammonia (i.e., $C_F$) and trapped ammonia (i.e., $C_T$) are assumed to spatially dependent. With these assumptions in mind, we let the RV and LV tissue curves be denoted by the continuous-time functions $f(t)$ and $g(t)$, respectively, and the free and trapped ammonia concentrations in the $i^{th}$ voxel within the myocardium (i.e., the $i^{th}$ myocardium voxel) be denoted by $g_{i,F}(t)$, and $g_{i,T}(t)$, respectively.

Under the above assumptions it follows that the rate constants in Hutchin's model are spatially dependent. After applying the Laplace transform to voxel dependent versions of equations (1) and (2), we get the following expressions for the concentrations of the free and trapped ammonia in the $i^{th}$ voxel within the myocardium $$g_{i,F}(t)=k_{i,1}g(t)*\exp(-\overline{k}_i t)u(t) \quad (4)$$

$$g_{i,T}(t)=k_{i,3}g_{i,F}(t)*u(t) \quad (5)$$

where $\overline{k}_i \triangleq k_{i,2}+k_{i,3}$, I is the number of voxels within the myocardium, and * denotes convolution operator. We note that $k_{1,1}, k_{2,1}, \ldots, k_{I,1}$ are the desired MBF parameters. In keeping with the assumptions behind (3), we assume the true TAC for the $i^{th}$ voxel in the myocardium is a superposition of the ammonia activity in the RV and LV, and free and trapped ammonia activity in the myocardial tissue $$a_i(t)=c_{i,1}f(t)+c_{i,2}g(t)+c_{i,3}g_{i,F}(t)+c_{i,4}g_{i,T}(t), i=1,2\ldots,I. \quad (6)$$

The first term in (6) is identified as the amount of spillover from the RV, and the second term is a combination of the ammonia activity in blood vessels within the myocardium and spillover from the LV. More specifically, the constant $c_{i,1}$ accounts for the amount of the ammonia activity in voxel i that is due to the blood plasma in the RV. Further, the constant $c_{i,2}$ accounts for the amount of the ammonia activity in voxel i that is due to the blood plasma in the LV (i.e., LV spill over) and blood plasma in the blood vessels of the myocardium. The third and fourth terms in (6) model the free and trapped ammonia activity in the myocardium, respectively. The coefficients $c_{i,3}$ and $c_{i,4}$ represent the fractional volume of voxel i that can be occupied by the ammonia activity in either the free or trapped states, respectively. Given that the free space for water in myocardial tissue is approximately 80%, we assume that $c_{i,3}=c_{i,4}=0.8$.

2. Discrete-Time Model for Activity in Myocardium

When a dynamic PET scan of the heart is taken, the images are separated into three sets of voxels that lie in the RV, LV, and myocardium such as that described by V. Appia, B. Ganapathy, A. Yezzi, and T. Faber in "Localized principal component analysis based curve evolution: A divide and conquer approach," 2011 International Conference on Computer Vision, pp. 1981-1986, 2011, which is incorporated by reference. Let the measured TACs associated with the set of voxels in the RV, LV, and myocardium be referred to as the RV TACs, LV TACs, and myocardium TACs, respectively. To model the underlying sampling process of dynamic PET scanning protocols, we let $d_i[n]$, $r[n]$, and $l[n]$ represent the discrete-time signals obtained by sampling $a_i(t)$, $f(t)$, and $g(t)$, respectively $$d_i[n] \triangleq a_i(nT_s), n=0, 1, \ldots, N-1, i=1, 2, \ldots, I \quad (7)$$

$$r[n] \triangleq f(nT_s), n=0,1, \ldots, N-1, \quad (8)$$

$$l[n] \triangleq g(nT_s), n=0,1, \ldots, N-1, \quad (9)$$

where $$f_s \triangleq \frac{1}{T}$$

is the sampling rate and T is the sampling interval. We will refer to the quantities $d_i[n]$ as the $i^{th}$ sampled myocardium TAC, and the discrete time signals $r[n]$ and $l[n]$, which are unknown, as the sampled RV tissue curve and sampled LV tissue curve, respectively. In applications where the scan durations for dynamic sequence PET protocols are not uniform, the assumption that the TACs are sampled uniformly is inappropriate. However, uniform samples of the TACs can be obtained from non-uniform samples of the TACs via a suitable interpolation using known methods.

It is of interest to determine a discrete-time system with the property that its response to the sampled RV and LV tissue curves closely approximates the $i^{th}$ sampled myocardium TAC. The bilinear transformation is a popular way to transform a linear time-invariant continuous-time system into a linear time-invariant discrete-time system. Specifically, the system function of a continuous-time system, H(s), can be converted into the system function of a discrete-time system $H_d(z)$ using $$H_d(z) = H(s) \Big|_{s=\frac{2}{T_s}\frac{1-z^{-1}}{1+z^{-1}}} \quad (10)$$

In our analysis, we make use of the z-transform. Let $x[n]$ be an arbitrary discrete-time sequence. The z-transform of $x[n]$ is defined to be $X(z) = \sum_{n=-\infty}^{\infty} x[n]z^{-n}$.

Taking the Laplace transform of (6), we get the following relationship $$A_i(s) = c_{i,1}F(s) + c_{i,2}G(s) + G(s)H_{i,F}(s) + G(s)H_{i,T}(s) \quad (11)$$

where $$H_{i,F}(s) \triangleq c_{i,3} \frac{k_{i,1}}{s+k_i} \quad (12)$$

$$H_{i,T}(s) \triangleq c_{i,4} \frac{k_{i,1}}{s+k_i} \frac{k_{i,3}}{s}. \quad (13)$$

After sampling $a_i(t)$, and applying the bilinear transformation to the system functions $H_{i,F}(s)$ and $H_{i,T}(s)$, we get the desired discrete-time model $$D_i(z) = c_{i,1}R(z) + c_{i,2}L(z) + c_{i,3}k_{i,1}(2/T_s+k_i)^{-1}L(z)\frac{1+z^{-1}}{1-p_iz^{-1}} + \quad (14)$$

$$c_{i,4}k_{i,1}k_{i,3}(2/T_s+k_i)^{-1}(2/T_s)^{-1}L(z)\frac{1+z^{-1}}{1-p_iz^{-1}}\frac{1+z^{-1}}{1-z^{-1}}$$

where $p_i \triangleq (2/T_s - k_i)(2/T_s+k_i)^{-1}$.

The bilinear transformation has the property that it maps a stable continuous-time system into a stable discrete-time system. Moreover, the bilinear transformation avoids the problem of aliasing by mapping the $j\Omega$ axis into the unit circle of the complex plane. However, frequency warping occurs as a result of mapping the entire $j\Omega$ axis into the unit circle. Note, the frequency warping problem can be ameliorated by choosing a sufficiently high sampling rate $f_s$.

From equation (14), it follows that the $i^{th}$ myocardium TAC, which is noisy in practice, can be expressed as $$d_i(n) = c_{i,1}r(n) + c_{i,2}l(n) + k_{i,1}(2/T_s+k_i)^{-1}l[n]*h_F[n;p_i] + k_{i,1}k_{i,3}(2/T_s+k_i)^{-1}(2/T_s)^{-1}l[n]*h_T[n;p_i] + e[n] \quad (15)$$

where $e[n]$ is the noise and * denotes discrete-time convolution. Also, $$h_F[n;\alpha] \triangleq c_{i,3}\mathcal{Z}^{-1}\left[\frac{1+z^{-1}}{1-\alpha z^{-1}}\right] \quad (16)$$

$$h_T[n;\alpha] \triangleq c_{i,4}\mathcal{Z}^{-1}\left[\frac{(1+z^{-1})^{-2}}{(1-\alpha z^{-1})(1-z^{-1})}\right] \quad (17)$$

where $\mathcal{Z}^{-1}$ denotes the inverse z-transform. Given the data $\{d_i[n]\}$, the problem is estimate the K-FADS-II model parameters:

$$r \triangleq [r[0], r[1], \ldots, r[N-1]] \quad (18)$$

$$l \triangleq [l[0], l[1], \ldots, l[N-1]] \quad (19)$$

$$c \triangleq \{c_{1,1}, c_{2,1}, \ldots, c_{I,1}, c_{1,2}, c_{2,2}, \ldots, c_{I,2}\} \quad (20)$$

$$k_1 \triangleq [k_{1,1}, k_{2,1}, \ldots, k_{I,1}] \quad (21)$$

$$k_2 \triangleq [k_{1,2}, k_{2,2}, \ldots, k_{I,2}] \quad (22)$$

$$k_3 \triangleq [k_{1,3}, k_{2,3}, \ldots, k_{I,3}] \quad (23)$$

Recall the parameters $k_1$, are the desired MBF parameters. Thus, the parameters $r$, $l$, $c$, $k_2$, and $k_3$ can be viewed as nuisance parameters because they must be accounted for in the analysis even though they are not of direct interest.

In the next section, we develop an algorithm for estimating the sampled RV and LV tissue curves and K-FADS-II parameters that we call the Improved Voxel Resolution MFB (IV-MBF) algorithm. The IV-MBF algorithm is based on a model that accounts for the fact that the shape of TACs due to ischemic and normal tissue are different. In fact, the model allows for tissue curves that represent free and trapped ammonia to be voxel dependent and physiologically appropriate. By contrast, in the standard FADS model, it is assumed that TACs in ischemic and normal tissue can be modeled as a linear combination of the same three factors.

$$L(r,l,c,k_1,k_2,k_3) \triangleq \sum_{i=1}^{I}\sum_{n=0}^{N-1}\{d_i[n] - (c_{i,1}r[n] + c_{i,2}l[n] + k_{i,1}(2/T_s+k_i)^{-1}l[n]*h_F[n;p_i] + k_{i,1}k_{i,3}(2/T_s)^{-1}(2/T_s+k_1)^{-1}l[n]*h_T[n;p_i])\}^2 \quad (26)$$

$$= \sum_{i=0}^{I}\sum_{n=0}^{N-1}\{d_i[n] - (c_{i,1}r[n] + l[n]*h[n;\theta_{i,h}])\}^2 \quad (27)$$

We believe the use of a more appropriate model offers the possibility of more accurate MBF estimates than available methods.

The IV-MBF algorithm performed well in a limited study using real patient data. The results of the study suggest that the IV-MBF algorithm is robust and would perform well in practice, where MBF values due to ischemic and normal tissue can vary over a wide range.

B. IV-MBF Algorithm

Consider the problem of minimizing a real valued function f with domain $D \in \mathbb{R}^n$. The majorize-minimize (MM) technique can be used to develop an algorithm that produces a sequence of iterates $\{x^{(m)}\}$ such that $f(x^{(m)})$ is a monotonically decreasing function such as those described by D. Hunter and K. Lange, "A Tutorial on MM Algorithms," The American Statistician, vol. 58, pp. 30-37, 2004, which is incorporated by reference. In this section, we first briefly introduce the MM technique and then we develop the IV-MBF algorithm by applying this technique to a certain LS objective function.

1. Review of the Majorize-Minimize Optimization Technique

A real valued function g with domain $\{(x_1, x_2): x_1, x_2 \in D\}$ is said to majorize the function $f$ if the following conditions hold for all x, y∈D:

$$g(x, y) \geq f(x) \quad (C1)$$

$$g(x, x) = f(x). \quad (C2)$$

MM algorithms are a viable approach provided a majorizing function can be found that is easier to minimize than the original objective function. Assuming that g is a suitable majorizing function for $f$, the corresponding MM algorithm is $$x^{(k+1)} = \arg\min_{x \in D} g(x, x^{(k)}), \quad (24)$$

where $x^{(k)}$ is the current estimate for the minimizer of $f$. It follows from (C1) and (C2) that the MM algorithm defined by equation (24) satisfies the monotonicity property [20]

$$f(x^{(k+1)}) \leq g(x^{(k+1)}, x^{(k)}) \leq g(x^{(k)}, x^{(k)}) = f(x^{(k)}) \quad (25)$$

2. IV-MBF Algorithm: LS Estimation of K-FADS-II Model Parameters

In our discussion we assume that suitable initial estimates are available. Later, in Section VII, we present a procedure for determining initial estimates for the K-FADS-II model parameters.

1) Construction of a LS Objective Function L:

Because no statistical information about the noise is available, we propose to estimate the K-FADS-II parameters using the LS estimation method. From equation (15), the LS objective function is given by where $h[n; \theta_{i,h}] \triangleq c_{i,2}\delta[n] + k_{i,1}(2/T_S+k_i)^{-1}h_F[n; p_i] + k_{i,1}k_{i,3}(2/T_S)^{-1}(2/T_S+k_i)^{-1}h_T[n; p_i]$ and $\theta_{i,h} \triangleq [c_{i,2}, k_{i,1}, k_{i,2}, k_{i,3}]$. It follows that a LS estimate of the K-FADS-II parameters is a solution to the following constrained optimization problem $$(\hat{r},\hat{l},\hat{c},\hat{k}_1,\hat{k}_2,\hat{k}_3) = \arg\min_{k_1,k_2,k_3 \geq 0} L(r,l,c,k_1,k_2,k_3) \text{ subject to } r,l,c, \quad (28)$$

b) Minimization of Least-Square Objective Function L:

We propose to minimize the LS objective function L by using the block coordinate descent method. In this method, the coordinates are partitioned into a fixed number of blocks and, at each iteration, the objective function is minimized with respect to one of the coordinate blocks while the remaining coordinates are fixed to their current estimates. Let $r^{(m)}$, $l^{(m)}$, $c^{(m)}$, $k_1^{(m)}$, $k_2^{(m)}$, and $k_3^{(m)}$ denote the current estimates for r, l, c, $k_1$, $k_2$, and $k_3$, respectively. An outline of an algorithm that, in principle, could be used for minimizing L follows Step 1

$$(r^{(m+1)}, l^{(m+1)}) \triangleq \arg\min_{r \geq 0, l \geq 0} L(r, l, c^{(m)}, k_1^{(m)}, k_2^{(m)}, k_3^{(m)}) \quad (29)$$

Step 2

$$k_2^{(m+1)} \triangleq \arg\min_{k_2 \geq 0} L(r^{(m+1)}, l^{(m+1)}, c^{(m)}, k_1^{(m)}, k_2, k_3^{(m)}) \quad (30)$$

$$k_3^{(m+1)} \triangleq \arg\min_{k_3 \geq 0} L(r^{(m+1)}, l^{(m+1)}, c^{(m)}, k_1^{(m)}, k_2^{(m+1)}, k_3) \quad (31)$$

Step 3

$$(c^{(m+1)}, k_1^{(m+1)}) \triangleq \arg\min_{c \geq 0, k_1 \geq 0} L(r^{(m+1)}, l^{(m+1)}, c, k_1, k_2^{(m+1)}, k_3^{(m+1)}) \quad (32)$$

A simpler alternative to Step 1 is to use the MM technique described above to obtain iterates $r^{(m+1)}$ and $l^{(m+1)}$ that decrease the least-squares objective L in the sense that, for all m=0, 1, 2, ..., $$L(r^{(m-1)},l^{(m+1)},c^{(m)},k_1^{(m)},k_2^{(m)},k_3^{(m)}) \leq L(r^{(m)},l^{(m)},c^{(m)},k_1^{(m)},k_2^{(m)},k_3^{(m)}) \quad (33)$$

Applying the same reasoning, we determine iterates $c^{(m+1)}$ and $k_1^{(m+1)}$ such that $$L(r^{(m+1)}, l^{(m+1)}, c^{(m)}, k_1^{(m+1)}, k_2^{(m+1)}, k_3^{(m+1)}) \le \\ L(r^{(m+1)}, l^{(m+1)}, c^{(m)}, k_1^{(m)}, k_2^{(m+1)}, k_3^{(m+1)}) \quad (34)$$

Taking this approach, steps 1 and 3 of the proposed algorithm are now

[Step 1a] Find iterates $r^{(m+1)}$ and $l^{(m+1)}$ such that $$L(r^{(m+1)}, l^{(m+1)}, c^{(m)}, k_1^{(m)}, k_2^{(m)}, k_3^{(m)}) \le \\ L(r^{(m)}, l^{(m)}, c^{(m)}, k_1^{(m)}, k_2^{(m)}, k_3^{(m)}) \quad (35)$$

[Step 3a] Find iterates $c^{(m+1)}$ and $k_1^{(m+1)}$ such that $$L(r^{(m+1)}, l^{(m+1)}, c^{(m+1)}, k_1^{(m+1)}, k_2^{(m+1)}, k_3^{(m+1)}) \le \\ L(r^{(m+1)}, l^{(m+1)}, c^{(m)}, k_1^{(m)}, k_2^{(m+1)}, k_3^{(m+1)}) \quad (36)$$

Solution to Step 1a:

To construct a majorizing function for $L$ at $(r^{old}, l^{old})$, where $r^{old}$ and $l^{old}$ are the current estimates for the sampled RV and LV tissue curves, respectively, we first construct a majorizing function for $(c_{i,1}r[n]+l[n]*h[n;\theta_{i,h}])^2$ by exploiting the following result, which is proven in the Proof of Result 1 section below:

Result 1:

Let $z_1[n]$, $z_2[n]$, and $w[n]$ be causal positive sequences (a sequence $w[n]$ is said to be causal if $w[n]=0$ for $n<0$), where $z_1[n]$ and $z_2[n]$ are of length N. A majorizing function for $(z_1[n]+z_2[n]*w[n])^2$ is $$(z_1^{old}[n] + z_2^{old}[n]*w[n])\left(\frac{(z_1[n])^2}{z_1^{old}[n]} + \sum_{k=0}^{N-1} w[n-k]\frac{(z_2[k])^2}{z_2^{old}[k]}\right) \quad (37)$$

where $z_1^{old}[n]$ and $z_2^{old}[n]$ are causal positive sequences of length N. From Result 1, it follows that a majorizing function for $L$ at $(r^{old}, l^{old})$ is $$q_L(r, l, c, k_1, k_2, k_3; r^{old}, l^{old}) = \quad (38)$$

$$\sum_{i=1}^{I}\sum_{n=0}^{N-1}\left\{d_i[n]^2 - 2d_i[n](c_{i,1}r[n]+l[n]*h[n;\theta_{i,h}]) + \right.$$

$$(c_{i,1}r^{old}[n]+l^{old}[n]*h[n;\theta_{i,h}]) \times$$

$$\left.\left(\frac{(c_{i,1}r[n])^2}{c_{i,1}r^{old}[n]} + \sum_{k=0}^{K-1} h[n-k;\theta_{i,h}]\frac{(l[k])^2}{l^{old}[k]}\right)\right\}$$

It should be observed that, as expected, $q_L(r^{old}, l^{old}, c, k_1, k_2, k_3; r^{old}, l^{old}) = L(r^{old}, l^{old}, c, k_1, k_2, k_3)$.

As discussed above, MM algorithms are attractive because they have the property that their respective objective functions are monotonically decreased with increasing iterations. Thus, it follows from this property that Step 1a can be obtained by solving the following optimization problem:

$$(r^{(m+1)}, l^{(m+1)}) \triangleq \arg\min_{r\ge 0, l\ge 0} q_L(r, l, c^{(m)}, k_1^{(m)}, k_2^{(m)}, k_3^{(m)}; r^{(m)}, l^{(m)}) \quad (39)$$

Before solving equation (39), we make the following definition $$\hat{d}_i[n; \theta_{i,d}] \triangleq c_{i,1}r[n]+l[n]*h[n;\theta_{i,h}] \quad (40)$$

where $\theta_{i,d} \triangleq [r, l, c_{i,1}, c_{i,2}, k_{i,1}, k_{i,2}, k_{i,3}]$. Now, to determine an update for $r$ and $l$, we take the partial derivative of the objective function on the right hand side of equation (39) with respect to $r$ and $l$, respectively, and set the results to zero. For $s=0, 1, \ldots, N-1$ the desired partial derivatives are $$\frac{\partial q_L(r, l, c^{(m)}, k_1^{(m)}, k_2^{(m)}, k_3^{(m)}; r^{(m)}, l^{(m)})}{\partial r[s]} = \sum_{i=1}^{I}\left(-2d_i[n]c_{i,1}^{(m)} + 2\hat{d}_i[n;\theta_{i,d}^{(m)}]c_{i,1}^{(m)}\frac{r[s]}{r^{(m)}[s]}\right) \quad (41)$$

$$\frac{\partial q_L(r, l, c^{(m)}, k_1^{(m)}, k_2^{(m)}, k_3^{(m)}; r^{(m)}, l^{(m)})}{\partial l[s]} = \sum_{i=1}^{I}\sum_{n=0}^{N-1}\left(-2d_i[n]h[n-s;\theta_{i,h}^{(m)}] + 2\hat{d}_i[n;\theta_{i,d}^{(m)}]h[n-s;\theta_{i,h}^{(m)}]\frac{l[s]}{l^{(m)}[s]}\right) \quad (42)$$

$$= \sum_{i=1}^{I}\left(-2\sum_{n=0}^{N-1}d_i[n]h[n-s;\theta_{i,h}^{(m)}] + 2\frac{l[s]}{l^{(m)}[s]}\sum_{n=0}^{N-1}\hat{d}_i[n;\theta_{i,d}^{(m)}]h[n-s;\theta_{i,h}^{(m)}]\right) \quad (43)$$

$$= \sum_{i=1}^{I}\left\{-2d_i[s]*h[-s;\theta_{i,h}^{(m)}] + 2\frac{l[s]}{l^{(m)}[s]}(\hat{d}_i[s;\theta_{i,d}^{(m)}]*h[-s;\theta_{i,h}^{(m)}])\right\} \quad (44)$$

where $\theta_{i,d}^{(m)} \triangleq [r^{(m)}, l^{(m)}, c_{i,1}^{(m)}, c_{i,2}^{(m)}, k_{i,1}^{(m)}, k_{i,2}^{(m)}, k_{i,3}^{(m)}]$ and $\theta_{i,h}^{(m)} \triangleq [c_{i,2}^{(m)}, k_{i,1}^{(m)}, k_{i,2}^{(m)}, k_{i,3}^{(m)}]$, and $\hat{d}_i[n; \theta_{i,d}^{(m)}]$ is the current estimate of the data point $d_i[n]$. Setting equations (41) and (44) to zero leads to the desired updates for the sampled RV and LV tissue curves:

$$r^{(m+1)}[n] = r^{(m)}[n]\frac{\sum_{i=1}^{I}c_{i,1}^{(m)}d_i[n]}{\sum_{i=1}^{I}c_{i,1}^{(m)}\hat{d}_i[n;\theta_{i,d}^{(m)}]}, n=0,1,\ldots,N-1 \quad (45)$$

$$l^{(m+1)}[n] = l^{(m)}[n]\frac{\sum_{i=1}^{I}d_i[n]*h[-n;\theta_{i,h}^{(m)}]}{\sum_{i=1}^{I}\hat{d}_i[n;\theta_{i,d}^{(m)}]*h[-n;\theta_{i,h}^{(m)}]}, n=0,1,\ldots,N-1 \quad (46)$$

The iterates defined by equations (45) and (46) have two important properties: (i) they satisfy the desired monotonicity properties given in equations (35), and (ii) are nonnegative provided the initial estimates, $r^{(m)}$, $l^{(m)}$, $c^{(m)}$, $k_{i,1}^{(m)}$, $k_{i,2}^{(m)}$, and $k_{i,3}^{(m)}$ are nonnegative. In preliminary simulation studies, we have found that the iteration in equation (45) has not consistently resulted in accurate estimates for the sampled RV tissue curve. We believe the inaccuracy may be due to the fact that the myocardium TACs contains limited information about the RV tissue curve. Therefore, although the update in equation (45) is theoretically meaningful, it may be advisable to use the estimate for the RV tissue curve obtained from the algorithm described below based on a semi-parametric model.

Solution to Step 2:

The minimization in Step 2 is equivalent to the following I minimization problems:

For $i = 1, 2, \ldots, I$, $$k_{i,2}^{(m+1)} \triangleq \arg\min_{k_{i,2} \geq 0} \sum_{n=0}^{N-1} \{d_i[n] - (c_{i,1}^{(m)} r^{(m+1)}[n] + c_{i,2}^{(m)} l^{(m+1)}[n] + \qquad (47)$$

$$k_{i,1}^{(m)}(2/T_S + (k_{i,2} + k_{i,3}^{(m)}))^{-1} l^{(m+1)}[n] * h_F[n; p_{i,2}^{(m)}] +$$

$$k_{i,1}^{(m)} k_{i,3}^{(m)}(2/T_S)^{-1}(2/T_S + (k_{i,2} + k_{i,3}^{(m)}))^{-1} l^{(m+1)}[n] * h_T[n; p_{i,2}^{(m)}])\}^2 \qquad (48)$$

$$k_{i,3}^{(m+1)} \triangleq \arg\min_{k_{i,2} \geq 0} \sum_{n=0}^{N-1} \{d_i[n] - (c_{i,1}^{(m+1)} r^{(m+1)}[n] + c_{i,2}^{(m)} l^{(m+1)}[n] +$$

$$k_{i,1}^{(m)}(2/T_S + (k_{i,2}^{(m+1)} + k_{i,3}))^{-1} l^{(m+1)}[n] * h_F[n; p_{i,3}^{(m+1)}] +$$

$$k_{i,1}^{(m)} k_{i,3}(2/T_S)^{-1}(2/T_S + (k_{i,2}^{(m+1)} + k_{i,3}))^{-1} l^{(m+1)}[n] * h_T[n; p_{i,2}^{(m+1)}])\}^2$$

where $$p_{i,2}^{(m)} \triangleq (2/T_S + (k_{i,2} + k_{i,3}^{(m)}))(2/T_S + (k_{i,2} + k_{i,3}^{(m)}))^{-1} \qquad (49)$$

$$p_{i,3}^{(m)} \triangleq (2/T_S + (k_{i,2}^m + k_{i,3}))(2/T_S + (k_{i,2}^{(m)} + k_{i,3}))^{-1} \qquad (50)$$

Each of the above one-dimensional optimization problems can be solved using a line search algorithm such as the golden section method [21].

Solution to Step 3a:

The minimization in Step 3 is equivalent to the following $I$ one-dimensional minimization problems:

For $i = 1, 2, \ldots, I$, $$\theta_i^{(m+1)} \triangleq \arg\min_{\theta_i \geq 0} \sum_{n=0}^{N-1} \{d_i[n] - (c_{i,1} r^{(m+1)}[n] + c_{i,2} l^{(m+1)}[n] + \qquad (51)$$

$$k_{i,1}(2/T_s + \overline{k}_i^{(m+1)})^{-1} l^{(m+1)}[n] * h_F[n; p_i^{(m+1)}] +$$

$$k_{i,3}^{(m+1)}(2/T_s)^{-1}(2/T_s + k_i^{(m+1)})^{-1} l^{(m+1)}[n] * h_T[n; p_i^{(m+1)}])\}^2$$

where $\theta_i \triangleq [c_{i,1}, c_{i,2}, k_{i,1}]$ and $\theta_i^{(m)} \triangleq [c_{i,1}^{(m)}, c_{i,2}^{(m)}, k_{i,1}^{(m)}]$. Also, $p_i^{(m)} \triangleq (2/T_s - k_i^{(m)})(2/T_s + k_i^{(m)})^{-1}$ where $\overline{k}_i^{(m)} \triangleq k_{i,2}^{(m)} + k_{i,3}^{(m)}$.

For all $n, i$ let $$s_{i,1}^{(m)}[n] \triangleq r^{(m)}[n] \qquad (52)$$

$$s_{i,2}^{(m)}[n] \triangleq l^{(m)}[n] \qquad (53)$$

$$s_{i,3}^{(m)}[n] \triangleq (2/T_s + \overline{k}_i^{(m)})^{-1} l^{(m)}[n] * h_F[n; p_i^{(m)}] + \qquad (54)$$

$$k_{i,3}^{(m)}(2/T_s)^{-1}(2/T_s + \overline{k}_i^{(m)})^{-1} l^{(m)}[n] * h_T[n; p_i^{(m)}]$$

It follows that equation (51) can be conveniently expressed as:

$$\theta_i^{(m+1)} \triangleq \arg\min_{\theta_i \geq 0} \sum_{n=0}^{N-1} \{d_i[n] - (c_{i,1} s_{i,1}^{(m+1)}[n] + \qquad (55)$$

$$c_{i,2} s_{i,2}^{(m+1)}[n] + k_{i,1} s_{i,3}^{(m+1)}[n])\}^2$$

$$= \arg\min_{\theta_i \geq 0} \| d_i - A_i^{(m+1)} \theta_i \|_2^2 \qquad (56)$$

where $\| \cdot \|_2$ is the $L_2$-norm,
$d_i = [d_i[0], d_i[1], \ldots, d_i[N-1]]^T$, and $$A_i^{(m+1)} = \begin{pmatrix} s_{i,1}^{(m+1)}[0] & s_{i,2}^{(m+1)}[0] & \ldots & s_{i,3}^{(m+1)}[0] \\ s_{i,1}^{(m+1)}[1] & s_{i,2}^{(m+1)}[1] & \ldots & s_{i,3}^{(m+1)}[1] \\ \vdots & \vdots & \ddots & \vdots \\ s_{i,1}^{(m+1)}[N-1] & s_{i,2}^{(m+1)}[N-1] & \ldots & s_{i,3}^{(m+1)}[N-1] \end{pmatrix} \qquad (57)$$

Observe that Step 3 requires the solution to equation (56) for all $i=1,2,\ldots,I$. However, since we propose to solve Step 3a instead of Step 3, we use a majorizing function for a certain class of linear LS objective functions that was put forth by De Pierro in "On the relation between the ISRA and the EM algorithms for positron emission tomography," IEEE Transactions on Medical Imaging, vol. 12, pp. 328-333, 1993, which is incorporated by reference. Given that $\theta_i$, $d_i$, and the matrix $A_i^{(m+1)}$ are nonnegative, De Pierro's result can be used to obtain the following majorizing function for $\| d_i - A_i^{(m+1)} \theta_i \|_2^2$ about the point $\theta_i^{(m)}$ $$q_1(\theta_i, \theta_i^{(m)}) \triangleq \sum_{j=0}^{N-1} d_i[j]^2 - \qquad (58)$$

$$2 \sum_{j=0}^{N-1} d_i[j][A_i^{(m+1)} \theta_i]_j + \sum_{j=0}^{N-1} \sum_{k=1}^{3} [A_i^{(m+1)} \theta_i^{(m)}]_j A_{i,j,k}^{(m+1)} \frac{\theta_{i,k}^2}{\theta_{i,k}^{(m)}}$$

where $A_{i,j,k}^{(m+1)}$ is the element in $j^{th}$ row and $k^{th}$ column of the matrix $A_i^{(m+1)}$, and $\theta_{i,k}$ is the $k^{th}$ element of the vector $\theta_i$. Additionally, for a vector $v$ the quantity $[v]k$ is defined to be the $k^{th}$ element of $v$. Now, the partial derivative of the majorizing function $q_1$ with respect to $\theta_{i,k}$ equals $$\frac{\partial q_1(\theta_i, \theta_i^{(m)})}{\partial \theta_{i,k}} = -2\left[ (A_i^{(m+1)})^T d_i \right]_k + 2 \frac{\theta_{i,k}}{\theta_{i,k}^{(m)}} \left[ (A_i^{(m+1)})^T (A_i^{(m+1)} \theta_i^{(m)}) \right]_k \qquad (59)$$

Setting this partial derivative to zero yields the desired update, which is also known as the iterative space image reconstruction algorithm (IRSA) as described in M. E. Daube-Witherspoon and G. Muehllehner, "Treatment of axial data in three-dimensional PET," Journal of Nuclear Medicine, vol. 28, pp. 1717-1724, 1987, which is incorporated by reference.

$$\theta_{i,k}^{(m+1)} = \theta_{i,k}^{(m)} \frac{\left[ (A_i^{(m+1)})^T d_i \right]_k}{\left[ (A_i^{(m+1)})^T (A_i^{(m+1)} \theta_i^{(m)}) \right]_k} \quad k = 1, 2, 3 \qquad (60)$$

From equation (60), the updates for the parameters $c_{i,1}$, $c_{i,2}$, and $k_{i,1}$ can be equivalently written as $$c_{i,k}^{(m+1)} = c_{i,k}^{(m)} \frac{\left[(A_i^{(m+1)})^T d_i\right]_k}{\left[(A_i^{(m+1)})^T (A_i^{(m+1)}) \theta_i^{(m)}\right]_k} \quad k = 1, 2 \quad (61)$$

$$k_{i,1}^{(m+1)} = k_{i,1}^{(m)} \frac{\left[(A_i^{(m+1)})^T d_i\right]_3}{\left[(A_i^{(m+1)})^T (A_i^{(m+1)}) \theta_i^{(m)}\right]_3} \quad (62)$$

C. Penalized MBF Algorithm

When the myocardium TACs are noisy, the MBF estimates generated by the iteration in equation (62) may be so noisy that some smoothing is necessary. Our approach for the addressing the noise is to add a limiting factor or penalty function that penalizes solutions where the MBF estimates for adjacent voxels differ significantly. Specifically, we develop the following penalized least-squares (PLS) method:

$$\theta_i^{(m+1)} \triangleq \arg\min_{\theta_i \geq 0} \| d_i - A_i^{(m+1)} \theta_i \|_2^2 + \lambda P(k_1) \quad (63)$$

where $P(k_1)$ is a penalty function, $N_i$ is a neighborhood about the $i^{th}$ voxel, and the penalty parameter, $\lambda$, determines the level of influence of the penalty function. For the penalty function, we choose the following quadratic penalty function:

$$P(k_1) = \sum_{i=1}^{I} \sum_{j \in N_i} (k_{i,1} - k_{j,1})^2 \quad (64)$$

A choice for $N_i$ is the intersection of the set of eight nearest voxels to the $i^{th}$ voxel and the set of voxels that lie in the myocardium. Note, penalty functions could also be used to enforce smoothness on the other parameters $c$, $k_2$, and $k_3$.

The following majorizing function for the penalty function P about the point $k_{i,1}(m)$ was provided in G. Wang and J. Qi, "Penalized likelihood PET image reconstruction using patch-based edge-preserving regularization," IEEE Transactions on Medical Imaging, vol. 31, pp. 2194-2204, 2012, which is incorporated herein by reference:

$$q_2(k_1, k_1^{(m)}) \triangleq$$

$$\sum_{i=1}^{I} \sum_{j \in N_i} \left[ 2\left(k_{i,1} - \frac{k_{i,1}^{(m)} + k_{j,1}^{(m)}}{2}\right)^2 + 2\left(k_{i,j} - \frac{k_{i,1}^{(m)} + k_{j,1}^{(m)}}{2}\right)^2 \right] \quad (65)$$

Because $q_1$ is a majorizing function for the LS objective function $\|d_i - A_i^{(m+1)} \theta_i\|_2^2$, it follows that $$q(\theta_i, \theta_i^{(m)}) \triangleq q_1(\theta_i, \theta_i^{(m)}) + \lambda q_2(k_1, k_1^{(m)}) \quad (66)$$

is a majorizing function for the PLS objective function in equation (63) about the point $\theta_i^{(m)}$. Consequently, an MM algorithm for obtaining PLS estimates of the MBF parameters can be expressed as $$\theta_i^{(m+1)} \triangleq \arg\min_{\theta_i \geq 0} q(\theta_i, \theta_i^{(m)}) \quad (67)$$

To get the update for $k_{i,1}$ using the PLS formulation, we first take the derivative of q with respect to $k_{i,1}$:

$$\frac{\partial q(\theta_i, \theta_i^{(m)})}{\partial k_{i,1}} = -2\left[(A_i^{(m+1)})^T d_i\right]_3 + 2\frac{k_{i,1}}{k_{i,1}^{(m)}} \left[(A_i^{(m+1)})^T (A_i^{(m+1)}) \theta_i^{(m)}\right]_3 + \quad (68)$$

$$8\lambda k_{i,1} |N_i| - 8\lambda \sum_{j \in N_i} \left[\left(\frac{k_{i,1}^{(m)} + k_{j,1}^{(m)}}{2}\right)\right]$$

where $|N_i|$ is the number of elements in the set $N_i$. Now, equating this result to zero leads to the desired result:

$$k_{i,1}^{(m+1)} = \frac{k_{i,1}^{(m)} \left[(A_i^{(m+1)})^T d_i\right]_3 + 2\lambda k_{i,1}^{(m)} \Sigma_{j \in N_i} (k_{i,1}^{(m)} + k_{j,1}^{(m)})}{\left[(A_i^{(m+1)})^T (A_i^{(m+1)}) \theta_i^{(m)}\right]_3 + 4\lambda k_{i,1}^{(m)} |N_i|}, \ i = 1, 2, ..., I \quad (69)$$

The penalty function does not depend on the parameters $c_{i,1}$ and $c_{i,2}$ so the updates $c_{i,1}^{(m+1)}$ and $c_{i,1}^{(m+1)}$ are given by equation (61).

In the PLS method, a choice is made for the penalty parameter $\lambda$. In our experiments, we chose the penalty parameter experimentally. However, the popular L-curve method could be used instead to determine the penalty parameter as discussed in P. C. Hansen, "Analysis of discrete ill-posed problems by means of the L-curve," SIAM Review, vol. 34, pp. 561-580, 1992; P. C. Hansen and D. P. OLeary, "The use of the L-curve in the regularization of discrete ill-posed problems," SIAM Journal Scientific Computing, vol. 14, p. 14871503, 1993; and T. Reginska, "A regularization parameter in discrete ill-posed problems," SIAM Journal Scientific Computing, vol. 17, p. 740749, 1996, each of which are incorporated herein in their entireties.

1. Semi-Parametric Model for Sampled RV and LV Tissue Curves

From an understanding of human physiology, it is well known that the RV and LV tissue curves will decay to zero. With the expectation of more accurate MBF estimation, we incorporate this knowledge by modeling the LV tissue curve as $$s_l[n; n_{0,l}, \beta] \triangleq \begin{cases} l[n], & 0 \leq n \leq n_{0,l} \\ l[n_{0,l}] \beta^{(n-n_{0,l})}, & n_{0,i} < n \leq N-1 \\ 0, & \text{otherwise}, \end{cases} \quad (70)$$

where $n_{0,l}$ and $\beta$ are unknown constants. We refer to this model as a semi-parametric model because only the sampled LV tissue curve values for $n \geq n_{0,l}$ are described by a parametric model. In our semi-parametric model based method, we account for the fact that the myocardium TACs contain little information about the RV tissue curve by combining the initial RV tissue curve estimate, $r(0)$, which is estimated in a non-parametric fashion, with the semi-parametric model for the LV tissue curve in the following manner:

$$s_r[n; n_{0,r}, \beta] \triangleq \begin{cases} r^{(0)}[n], & 0 \leq n \leq n_{0,r} \\ r^{(0)}[n_{0,r}] \beta^{(n-n_{0,r})}, & n_{0,r} < n \leq N-1 \\ 0, & \text{otherwise}, \end{cases} \quad (71)$$

where the parameter $n_{0,r}$ is unknown. For the estimated sampled RV and LV tissue curves to be nonnegative and decay to zero, the parameter $\beta$ must satisfy the constraint $0<\beta<1$.

2. LS Estimation of Sampled RV and LV Tissue Curves for $n_{0,r}$ and $n_{0,l}$ Known For the moment, we will assume that the parameters $n_{0,r}$ and $n_{0,l}$ are known. Using the models for the sampled RV and LV tissue curves expressed by equations (70) and (71), the associated LS objective function is given by $$\overline{L}(l_{n_{0,l}}, \beta, c, k_1, k_2, k_3) = \qquad (72)$$

$$\sum_{i=1}^{I} \sum_{n=0}^{N-1} \{d_i[n] - (c_{i,1}s_r[n; n_{0,r}, \beta] + s_l[n; n_{0,l}, \beta] * h[n; \theta_{i,h}])\}^2$$

where $l_{n_{0,l}} \triangleq [l[0], l[1], \ldots, l[n_{0,l}]]$. Therefore, an alternative approach to Step 1a are the following two steps:

Model Based Step 1a: Find an iterate $l_{n_{0,l}}^{(m+1)}$ such that:

$$\overline{L}(l_{n_{0,l}}^{(m+1)}, \beta^{(m)}, c^{(m)}, k_1^{(m)}, k_2^{(m)}, k_3^{(m)}) \leq \overline{L}(l_{n_{0,l}}^{(m)}, \beta^{(m)}, c^{(m)}, k_1^{(m)}, k_2^{(m)}, k_3^{(m)}) \qquad (73)$$

Model Based Step 1b $$\beta^{(m+1)} \triangleq \arg \min_{\epsilon \leq \beta \leq 1-\epsilon} \overline{L}(l_{n_{0,l}}^{(m+1)}, \beta^{(m)}, c^{(m)}, k_1^{(m)}, k_2^{(m)}, k_3^{(m)}) \qquad (74)$$

where $\epsilon$ is a small positive constant. Note replacing the constraint $0<\beta<1$ with $\epsilon \leq \beta \leq 1-\epsilon$ makes the problem in Model Based Step 1b well defined.

First, we address the problem in Model Based Step 1a. Let the N×1 vectors $s_r^{old}$ and $s_l^{old}$ denote an estimate of the semi-parametric RV and LV tissue curves, respectively:

$$s_r^{old} \triangleq [s_r^{old}[0; n_{0,r}, \beta^{old}], s_r^{old}[1; n_{0,r}, \beta^{old}], \ldots, s_r^{old}[N-1; n_{0,r}, \beta^{old}]] \qquad (75)$$

$$= [r^{(0)}[0], r^{(0)}[1], \ldots, r^{(0)}[n_{0,r}], r^{(0)}[n_{0,r}](\beta^{old})^1, \ldots, r^{(0)}[n_{0,r}](\beta^{old})^{N-1-n_{0,r}}] \qquad (76)$$

$$s_l^{old} \triangleq [s_l^{old}[0; n_{0,l}, \beta^{old}], s_l^{old}[1; n_{0,l}, \beta^{old}], \ldots, s_l^{old}[N-1; n_{0,l}, \beta^{old}]] \qquad (77)$$

$$= [l^{old}[0], l^{old}[1], \ldots, l^{old}[n_{0,l}], l^{old}[n_{0,l}](\beta^{old})^1, \ldots, l^{old}[n_{0,l}](\beta^{old})^{N-1-n_{0,l}}] \qquad (78)$$

Mimicking the steps used to derive equation (38), a majorizing function for $\overline{L}$ at $(s_r^{old}, s_l^{old})$ is:

$$q_{\overline{L}}(l_{n_{0,l}}, \beta, c, k_1, k_2, k_3; s_r^{old}, s_l^{old}) = \sum_{i=1}^{I} \sum_{n=0}^{N-1} \Bigg\{ d_i[n]^2 - \qquad (79)$$

$$2d_i[n](c_{i,1}s_r[n; n_{0,r}, \beta] + s_l[n; n_{0,l}, \beta] * h[n; \theta_{i,h}]) +$$

$$(c_{i,1}s_r^{old}[n; n_{0,r}, \beta^{old}] + s_l^{old}[n; n_{0,l}, \beta^{old}] * h[n; \theta_{i,h}]) \times$$

$$\Bigg( \frac{(c_{i,1}s_r[n; n_{0,r}, \beta])^2}{c_{i,1}s_r^{old}[n; n_{0,r}, \beta^{old}]} +$$

$$\sum_{k=0}^{N-1} h[n-k; \theta_{i,h}] \frac{(s_l[k; n_{0,l}, \beta])^2}{s_l^{old}[k; n_{0,l}, \beta^{old}]} \Bigg) \Bigg\}$$

For $v=0, 1, \ldots, n_{0,l}$, the derivative of $q_{\overline{L}}$ with respect to $s_l[v; n_{0,l}, \beta_l]$ follows from equation (44) and is equal to $$\frac{\partial q_{\overline{L}}(l_{n_{0,l}}^{(m)}, \beta^{(m)}, c^{(m)}, k_1^{(m)}, k_2^{(m)}, k_3^{(m)}; s_r^{(m)}, s_l^{(m)})}{\partial s_l[v; n_{0,l}, \beta]} = \qquad (80)$$

$$\sum_{i=1}^{I} \sum_{n=0}^{N-1} \Bigg\{ -2d_i[n]h[n-v; \theta_{i,h}^{(m)}] +$$

$$2\overline{d}_i[n; s_r^{(m)}, s_l^{(m)}, c_{i,1}^{(m)}, \theta_{i,h}^{(m)}]h[n-v; \theta_{i,h}^{(m)}] \frac{s_l[v; n_{0,l}, \beta^{(m)}]}{s_l^{(m)}[v; n_{0,l}, \beta^{(m)}]} \Bigg\}$$

$$= \sum_{i=1}^{I} \Bigg\{ -2d_i[v] * h[-v; \theta_{i,h}^{(m)}] + \qquad (81)$$

$$2 \frac{s_l[v; n_{0,l}\beta^{(m)}]}{s_l^{(m)}[v; n_{0,l}, \beta^{(m)}]} (\overline{d}_i[v; s_r^{(m)}, s_l^{(m)}, c_{i,1}^{(m)}, \theta_{i,h}^{(m)}] * h[-v; \theta_{i,h}^{(m)}]) \Bigg\}$$

where $s_r^{(m)}$ and $s_l^{(m)}$ are derived in a similar way as $s_r^{(old)}$ and $s_l^{(old)}$, respectively, and $$\overline{d}_i[n; s_r^{(m)}, s_l^{(m)}, c_{i,1}^{(m)}, \theta_{i,h}^{(m)}] \triangleq c_{i,1}^{(m)} s_r^{(m)}[n; n_{0,r}, \beta^{(m)}] + s_l^{(m)}[n; n_{0,l}, \beta^{(m)}] * h[n; \theta_{i,h}^{(m)}] \qquad (82)$$

is an estimate for the data point $d_i[n]$ using the semi-parametric model for the sampled RV and LV tissue curves in equations (70) and (71). From the definition in equation (70), for $n=0, 1, \ldots, n_{0,l}$, it follows that $s_l[v; n_{0,l}, \beta] = l[v]$ and $s_l^{(m)}[v; n_{0,l}, \beta^{(m)}] = l^{(m)}[v]$. Thus, for $n=0, 1, \ldots, n_{0,l}$, the partial derivative in equation (82) becomes $$\frac{\partial q_{\overline{L}}(l_{n_{0,l}}^{(m)}, \beta^{(m)}, c^{(m)}, k_1^{(m)}, k_2^{(m)}, k_3^{(m)}; s_r^{(m)}, s_l^{(m)})}{\partial s_l[v; n_{0,l}, \beta]} = \qquad (83)$$

$$\frac{\partial q_{\overline{L}}(l_{n_{0,l}}, \beta^{(m)}, c^{(m)}, k_1^{(m)}, k_2^{(m)}, k_3^{(m)}; s_r^{(m)}, s_l^{(m)})}{\partial l[v]}$$

$$= \sum_{i=1}^{I} \Bigg\{ -2d_i[v] * h[-v; \theta_{i,h}^{(m)}] + \qquad (84)$$

$$2 \frac{l[v]}{l^{(m)}[v]} (\overline{d}_i[v; s_r^{(m)}, s_l^{(m)}, c_{i,1}^{(m)}, \theta_{i,h}^{(m)}] * h[-v; \theta_{i,h}^{(m)}]) \Bigg\}$$

Setting equation (85) to zero leads to the desired update for the sampled LV tissue curve for $n=0, 1, \ldots, n_{0,l}$ $$l^{(m+1)}[n] = l^{(m)}[n] \frac{\sum_{i=1}^{I} d_i[n] * h[-n; \theta_{i,h}^{(m)}]}{\sum_{i=1}^{I} \overline{d}_i[n; s_r^{(m)}, s_l^{(m)}, c_{i,1}^{(m)}, \theta_{i,h}^{(m)}] * h[-n; \theta_{i,h}^{(m)}]} \qquad (85)$$

The next update for $\beta$ is obtained by solving the minimization problem in Model Based Step 1b by applying a one-dimensional line search such as described by M. S. Bazaraa, H. D. Sherali, and C. M. Shetty, Nonlinear Programming Theory and Algorithms. New York, N.Y.: John Wiley & Sons, Second Edition, Chapter 8, 1993, which is incorporated by reference. Finally, given $\beta^{(m+1)}$, the next estimates for the RV and LV tissue curve at the same point $n=n_{0,r}+1, n_{0,r}+2, \ldots N-1$ and $n=n_{0,l}+1, n_{0,l}+2, \ldots N-1$, respectively, are given by:

$$r^{(m+1)}[n] = r^{(0)}[n_{0,r}](\beta^{(m+1)})^{(n-n_{0,r})} \qquad (86)$$

$$l^{(m+1)}[n] = l^{(m+1)}[n_{0,l}](\beta^{(m+1)})^{(n-n_{0,l})} \qquad (87)$$

Summarizing, the updates for the sampled RV and LV tissue curves when the semi-parametric model is assumed are given by $$r^{(m+1)}[n] = \begin{cases} r^{(0)}[n], & 0 \le n \le n_{0,r} \\ r^{(0)}[n_{0,r}](\beta^{(m+1)})^{(n-n_{0,r})}, & n_{0,r} < n \le N-1 \\ 0, & \text{otherwise,} \end{cases} \quad (88)$$

$$l^{(m)}[n] = \begin{cases} l^{(m)}[n] \frac{\sum_{i=1}^{I} d_i[n] * h[-n; \theta_{i,h}^{(m)}]}{\sum_{i=1}^{I} \bar{d}_i[n; s_r^{(m)}, s_l^{(m)}, c_{i,1}^{(m)}, \theta_{i,h}^{(m)}] * h[-n; \theta_{i,h}^{(m)}]}, & 0 \le n \le n_{0,l} \\ l^{(m+1)}[n_{o,l}](\beta^{(m+1)})^{(n-n_{0,l})}, & n_{0,l} < n \le N-1 \\ 0, & \text{otherwise} \end{cases} \quad (89)$$

3. Estimation of the Parameters: $n_{0,r}$ and $n_{0,l}$

We define $d_{avg,r}[n]$ and $d_{avg,l}[n]$ to be the average of the RV and LV TACs, respectively. Let $n_{r,max}$ and $n_{l,max}$ equal the time points where $d_{avg,r}[n]$ and $d_{avg,l}[n]$ equal their maximum values, respectively. Additionally, let $n_{r,half}$ represent the time point after $n_{r,max}$ where $d_{avg,r}[n]$ is halfway down from its maximum value (note: $n_{l,half}$ is defined similarly). A reasonable assumption is that the time points where the sampled RV and LV tissues curves begin to decay exponentially are $n_{r,half}$ and $n_{l,half}$ respectively.

Another approach would be to first compute the K-FADS-II parameters for each $(n_{0,r}, n_{0,l})$ pair that comes from a set of $(n_{\phi,r}, n_{\phi,l})$ pairs, such as the set $$\{(n_{r,half},n_{l,half}),(n_{r,half}+1,n_{l,half}+1), \ldots ,(n_{r,half}+T_{max}, n_{l,half}+T_{max})\} \quad (90)$$

where $T_{max}$ would be specific by the user. Then, an error criterion known as the minimum description criterion such as that described in B. Porat, Digital Processing of Random Signals: Theory and Methods. New York, N.Y.: Prentice Hall, 1994, which is incorporated by reference, would be used to determine the optimal estimates for $n_{0,r}$ and $n_{0,l}$ and then the K-FADS-II parameters would be estimated using the proposed algorithm.

E. Initialization Procedure

In this section, we first discuss a straightforward way to obtain initial estimates of the RV and LV tissue curves. Then, given these initial estimates, we present a reliable way to generate initial estimates for $c$, $k_1$, $k_2$, and $k_3$.

1. Initial RV and LV Tissue Curves

Due to the motion of the heart and the finite resolution of PET imaging, the RV and LV TACs are corrupted by activity in the myocardium so they do not decay to zero. Keeping in mind the reasoning behind the semi-parametric model for the RV and LV tissue curves, the initial RV and LV tissue curves are chosen to be $$r^{(0)}[n] = \begin{cases} d_{avg,r}[n], & 0 \le n \le n_{0,r} \\ d_{avg,r}[n_{0,r}](\beta^{(0)})^{(n-n_{0,r})}, & n_{0,r} < n \le N-1 \\ 0, & \text{otherwise,} \end{cases} \quad (91)$$

$$l^{(0)}[n] = \begin{cases} d_{avg,l}[n], & 0 \le n \le n_{0,l} \\ d_{avg,l}[n_{0,l}](\beta^{(0)})^{(n-n_{0,l})}, & n_{0,l} < n \le N-1 \\ 0, & \text{otherwise} \end{cases} \quad (92)$$

where $\beta^{(0)}$ is the initial estimate of the parameter $\beta$.

An extension of this initialization procedure is to first determine the maximum value of each of RV TAC and then scale $r^{(0)}[n]$ in equation (91) so that its maximum value equals the average of the Q largest maximum values. The corresponding scale factor would be applied to $l^{(0)}[n]$ in equation (92). The underlying assumption behind this extension is that the RV and LV TACs with the largest maximum values have the least amount of noise due to activity in the myocardium. Note, in the experiments discussed in Section VIII we used $\beta^{(0)}=0.95$ and $Q=3$.

2. Initial Estimates for the Parameters: $k_2$, and $k_3$

Now, we will describe a method for finding initial estimates for $k_2$ and $k_3$ given the initial estimates $r^{(0)}$ and $l^{(0)}$. The model in equation (14) can be written as:

$$D_i(z) = c_{i,1}R(z) + L(z)\frac{c_{i,2}(1-p_i z^{-1})(1-z^{-1}) + \bar{c}_{i,3}(1-z^{-1})(1+z^{-}) + \bar{c}_{i,4}(1+z^{-1})^2}{(1-p_i z^{-1})(1-z^{-1})} \quad (93)$$

where $\bar{c}_{i,3} \triangleq c_{i,3}k_{i,1}(2/T_s+k_i)^{-1}$ and $\bar{c}_{i,4} \triangleq c_{i,4}k_{i,1}k_{i,3}(2/T_s+k_i)^{-1}(2/T_s)^{-1}$. Thus, for some second-order polynomial $B_i(z)=b_i[0]+b_i[1]z^{-1}+b_i[2]z^{-2}$ and first-order polynomial $M_i(z)=m_i[0]+m_i[1]z^{-1}$, and first order polynomial $A_i(z)=a_i[0]+a_i[1]z^{-1}$ with $a_i[0]=1$, it follows that:

$$D_i(z) = \frac{M_i(z)R(z) + \bar{L}(z)B_i(z)}{A_i(z)} \quad (94)$$

where $$\bar{L}(z) = \frac{L(z)}{1-z^{-1}} \quad (95)$$

Comparing equations (93) and (94) it can be seen that $a_i[1]=p_i$. Given the myocardium TACs $\{d_i[n]\}$ and initial estimates for the sampled RV and LV tissue curves, the problem is to estimate the parameter vector $\phi \triangleq [a_i[1], b_i[0], b_i[1], b_i[2], m_i[0], m_i[1]]$.

To estimate $\phi$, we propose an equation-error method that is a modification of the well-known Steiglitz-McBride algorithm and based on $$D_i(z)A_i(z)=M_i(z)R(z)+\bar{L}(z)B_i(z) \quad (96)$$

which follows from equation (94). The advantage of using equation (95) instead of equation (94) is that the former equation leads to a linear LS method while the latter results in a nonlinear LS formulation. The corresponding time-domain expression for equation (96) is $$d_i[n]*a_i[n]=r[n]*m_i[n]+l[n]*u[n]*b_i[n] \quad (97)$$

where $u[n]$ is the discrete-time unit step function. It follows from equation (97) that the parameter $\phi$ could be estimated by minimizing $L_{i,init}(\phi)$ where $$L_{i,init}(\phi) \triangleq \sum_{n=0}^{N-1} \{d_i[n] * a_i[n] - (\bar{r}[n] * m_i[n] + \bar{l}[n] * b_i[n])\}^2 \quad (98)$$

where $\bar{r}[n] \triangleq r^{(0)}[n]$ and $\bar{l}[n] \triangleq l^{(0)}[n]*u[n]$. Instead, we modify a method suggested by Steiglitz and McBride for estimating the parameters of the rational system function of a discrete-time, linear time-invariant system given input-output data from the system.

Algorithm 1 below is a summary of the method proposed for determining initial values for the parameters $p \triangleq [p_1, p_2, \ldots, p_I]$, $k_2$, and $k_3$. The reader should keep in mind the following relationships from above: $\bar{k} \triangleq k_{i,2} + k_{i,3}$ and $p_i \triangleq (2/T_S - k_i)(2/T_S - k_i)^{-1}$.

---

Algorithm 1 Initialization Procedure for the Parameteres p, $k_2$, and $k_3$

---

Get $d_{avg,r}[n]$ and $d_{avg,l}[n]$ for $n = 0, 1, \ldots, N - 1$
$n_{0,r} \leftarrow n_{r,half}$
$n_{0,l} \leftarrow n_{l,half}$
Choose $0 < \beta^{(0)} < 1$
Get $r^{(0)}$ and $l^{(0)}$ using equations (92) and (93)
For all $i = 1, 2, \ldots, I$ do $$\phi_i^{(0)} \leftarrow \arg\min_{\phi_i} L_{i,init}(\phi_i), \quad (99)$$

For all $j = 0, 1, \ldots, J_1 - 1$
    Get the sequence $h[n; a^{(s)}[1]]$ where $h[n; \alpha] \triangleq \mathcal{Z}^{-1}\left[\dfrac{1}{1-\alpha z^{-1}}\right] = \alpha^n u[n]$ Compute $d_i^{(s)}[n] \leftarrow d_i[n] * h[n; a_i^{(s)}[1]]$
    Compute $\bar{r}^{(s)}[n] \leftarrow \bar{r}[n] * h[n; a_i^{(s)}[1]]$
    Compute $\bar{l}^{(s)}[n] \leftarrow \bar{l}[n] * h[n; a_i^{(s)}[1]]$
    Get new estimate for $\varphi_i$ $$\phi_i^{(s+1)} \triangleq \arg\min_{\phi_i} L_{i,init}^{(s)}(\phi_i), \quad (100)$$

where $L_{i,init}^{(s)}(\phi_i) \triangleq \sum_{n=0}^{N-1} (d_i^{(s)}[n] * a_i[n] - (\bar{r}^{(s)}[n] * m_i[n] + \bar{l}^{(s)}[n] * b_i[n]))^2$ end for
$p_i^{(0)} \leftarrow \hat{a}[1]$ where $\hat{\varphi}_i \triangleq (\hat{a}_i[1], \hat{b}_i[0], \hat{b}_i[1], \hat{\bar{b}}_i[2], \hat{m}_i[0], \hat{m}_i[1])$ is the resulting estimate for $\varphi_i$ $k_i^{(0)} \leftarrow \dfrac{2}{T_S} \dfrac{1 - p_i^{(0)}}{1 + p_i^{(0)}}$ $k_{i,2}^{(0)} \leftarrow k_i^{(0)} \dfrac{\text{factor}}{1 + \text{factor}}$, $k_{i,3}^{(0)} \leftarrow k_i^{(0)} \dfrac{1}{1 + \text{factor}}$, end for

---

The optimization problem in (99) and (100) are straightforward because they are in the form of an unconstrained, linear LS estimation problem, which has a known solution. Specifically, the problems are of the form:

$$\hat{x} \triangleq \arg\min_x \|y - Ax\|_2^2 \quad (101)$$

where y is the data and A is a known matrix. The unique minimum $L_2$ norm solution is given by $\hat{x} = A^+ b$, where $A^+$ is the pseudoinverse of A per known applied linear algebra techniques.

It can be shown using K. Steiglitz and L. McBride. "A technique for the identification of linear systems," IEEE Transactions on Automatic Controls, vol. 10, pp. 461-464, 1965, which is incorporated herein by reference, that the objective function $L_{i,init}^{(s)}$ can be viewed as a suitable approximation to the nonlinear LS objective function that follows from the relation in equation (94). Also, it should be noted that $k_{i,2}^{(0)} + k_{i,2}^{(0)} = \bar{k}_i^{(0)}$. In our experiments, we chose $J_1 = 20$, $\beta^{(0)} = 0.95$, and the scalar "factor" to be 0.1 because typically $k_{i,2}$ is about 10% of $k_{i,3}$.

3. Initial Estimates for the Parameters: c, $k_1$

Given the initial estimates $r^{(0)}$, $l^{(0)}$, $k_{i,2}^{(0)}$, $k_{i,3}^{(0)}$, we generate initial estimates for c and k by solving the following minimization problem $$(c^{(0)}, k_1^{(0)}) \triangleq \arg\min_{c \geq 0, k_1 \geq 0} J(r^{(0)}, l^{(0)}, c, k_1, k_2^{(0)}, k_3^{(0)}) \quad (103)$$

As discussed above, this problem can be solved using the ISRA algorithm as shown below in Algorithm 2 (see also equations (61) and (62)).

---

Algorithm 2 Initialization Procedure for the Parameters c and $k_1$

---

Run Algorithm 1 to get initial estimates: $r^{(0)}$, $l^{(0)}$, $k_2^{(0)}$, and $k_3^{(0)}$
For all $i = 0, 1, \ldots, I - 1$ do
    $\theta_i^{(0)} \leftarrow [1,1,1]^T$
    Get $A_i^{(0)}$ using equation (57)
    For all $j = 1, 2, \ldots, J_2 - 1$ $$\theta_{i,k}^{(0)} \leftarrow \theta_{i,k}^{(0)} \dfrac{[(A_i^{(0)})^T d_i]_k}{[(A_i^{(0)})^T (A_i^{(0)} \theta_i^{(0)})]_k}, \ k = 1, 2, 3$$

end for
end for

---

In our experiments, we used $J_2 = 500$.

F. Experimental Results

We tested the IV-MBF algorithm, which is summarized in Algorithm 3 below, using real patient data provided by Dr. John Votaw, Professor and Vice Chair for Research, Director of Physics and Computing in Radiology, and Professor of Radiology and Physics at the Emory University School of Medicine.

---

Algorithm 3 IV-MBF Algorithm

---

Run Algorithm 1 and Algorithm 2 to get initial estimates for $r^{(0)}$, $l^{(0)}$, $c^{(0)}$, $k_1^{(0)}$, $k_2^{(0)}$, and $k_3^{(0)}$
for all $j = 0, 1, \ldots, J_3 - 1$ do
    for all $n = 0, 1, \ldots, n_{0,r}$ do
        $r^{(m+1)}[n] \leftarrow r^{(0)}[n]$
    end for
    for all $n = 0, 1, \ldots, n_{0,l}$ do -continued Algorithm 3 IV-MBF Algorithm $$l^{(m+1)}[n] \leftarrow l^{(m)}[n] \frac{\sum_{i=1}^{I} d_i[n] * h[-n; \theta_{i,h}^{(m)}]}{\sum_{i=1}^{I} \bar{d}_i[n; s_r^{(m)}, s_l^{(m)}, c_{i,l}^{(m)}, \theta_{i,h}^{(m)}] * h[-n; \theta_{i,h}^{(m)}]},$$

end for
Compute $\beta^{(m+1)}$ using (74) and one-dimensional line search
for all n = $n_{0,r}$ + 1, $n_{0,r}$ + 2, ..., N − 1 do
$\quad r^{(m+1)}[n] \leftarrow r^{(0)}[n_{0,r}](\beta^{(m+1)})^{(n-n_{0,r})}$
end for
for all n = $n_{0,l}$ + 1, $n_{0,l}$ + 2, ..., N − 1 do
$\quad l^{(m+1)}[n] \leftarrow l^{(m+1)}[n_{0,l}](\beta^{(m+1)})^{(n-n_{0,l})}$
end for
for all I = 1, 2, ..., I do
$\quad$ Compute $k_{i,2}^{(m+1)}$ and $k_{i,3}^{(m+1)}$ using equations (47) and
$\quad$ (48), and a one-dimensional line search $$c_{i,k}^{(m+1)} \leftarrow c_{i,k}^{(m)} \frac{\left[(A_i^{(m+1)})^T d_i\right]_k}{\left[(A_i^{(m+1)})^T (A_i^{(m+1)} \theta_i^{(m)})\right]_k}, k = 1, 2$$

$$k_{i,1}^{(m+1)} \leftarrow \frac{k_{i,1}^{(m)} \left[(A_i^{(m+1)})^T d_i\right]_3 + 2\lambda k_{i,1}^{(m)} \Sigma_{j \in N_i}(k_{i,1}^{(m)} + k_{j,1}^{(m)})}{\left[(A_i^{(m+1)})^T (A_i^{(m+1)} \theta_i^{(m)})\right]_3 + 4\lambda k_{i,1}^{(m)} |N_i|}$$

end for
end for

An alternative implementation simply uses the initial estimates $r^{(0)}$, $l^{(0)}$ after subtracting off activity due to the myocardium, as the final RV and LV tissue curves, respectively.

1. Description of Experimental Results Analysis

The dynamic PET data set comes from scanning an unhealthy patient at rest using a standard protocol consisting of 20 scans of duration 3 sec, followed by 5 scans of duration 12 sec, and ending with 6 scans of duration 30 sec (i.e., 31 sub-scans in total). The scanner used in the study has 22 planes and the reconstructed cardiac images are of size 42×30. Therefore, the data set consists of 31 images of size 42×30 per plane.

Let $a_{i,j}$ denote the measured activity in the $i^{th}$ myocardium voxel during the $j^{th}$ sub-scan. Then, $\{a_{i,1}, a_{i,2}, \ldots, a_{i,J}\}$ for J=31 is the $i^{th}$ myocardium TAC in the dynamic PET data set. The measured $\{a_{i,j}\}$ can be modeled as $$a_{i,j} = \begin{cases} \frac{1}{T_1} \int_{u_{j,1}-T_1}^{u_{j,1}} a_i(t) dt, & j = 1, 2, \ldots, 20 \\ \frac{1}{T_2} \int_{u_{j,2}-T_2}^{u_{j,2}} a_i(t) dt, & j = 21, 22, \ldots, 25 \\ \frac{1}{T_3} \int_{u_{j,3}-T_3}^{u_{j,3}} a_i(t) dt, & j = 26, 27, \ldots, 31 \end{cases} \quad (103)$$

where $a_i(t)$ is the $i^{th}$ ideal continuous-time myocardium TAC (see (6)), and $T_1$=3 sec, $T_2$=12 sec, and $T_3$=30 sec are the sub-scan durations, and $u_{j,1} \triangleq jT_1$, $u_{j,2} \triangleq 20T_1 + (j-20)T_2$, and $u_{j,3} \triangleq 20T_1 + 5T_2 + (j-25)T_3$. The IV-MBF algorithm is based on regularly sampled myocardium TAC data (i.e., $d_i[n] = a_i(nT)$). Consequently, the measured myocardium data, $\{a_{i,j}\}$, must be pre-processed in order to estimate the regularly sampled myocardium TAC data $\{d_i[n]\}$. A popular approach is to first assume the measured myocardium TAC data is nearly piece-wise linear. Under this assumption and as discussed in W. G. Kuhle, G. Porenta, S. C. Huang, D. Buxton. S. S. Gambhir, H. Hansen, M. E. Phelps, and H. R. Schelbert, "Quantification of regional myocardial blood flow using 13N-ammonia and reoriented dynamic positron emission tomographic imaging," Circulation, vol. 86, pp. 1004-17, 1992, which is incorporated by reference, it follows that the values of $a_i(t)$ at the midpoints of the sub-scan windows are approximately equal to $$a_i(u_{j,1} - T_1/2) \approx a_{i,j}, j = 1, 2, \ldots 20 \quad (104)$$

$$a_i(u_{j,2} - T_2/2) \approx a_{i,j}, j = 21, 22, \ldots 25 \quad (105)$$

$$a_i(u_{j,3} - T_3/2) \approx a_{i,j}, j = 26, 27, \ldots 31 \quad (106)$$

Thus, the regularly sampled myocardium TAC data can be estimated from the measured myocardium TAC data using interpolation. Specifically, we use the "known" values for $a_i(t)$, which are $\{a_i(u_{j,1} - T_1/2)\}_{j=1}^{20}$, $\{a_i(u_{j,2} - T_2/2)\}_{j=21}^{25}$, and $\{(a_i(u_{j,3} - T_3/2)\}_{j=26}^{31}$, and linear interpolation to obtain estimates for the regularly sampled myocardium TACs. Note, in our experiment we used $T_s$=0.5 sec for the sampling interval. It should be mentioned that the approach described above for generating regularly sampled myocardium TACs from the measured myocardium TAC data would also be used to generate the regularly sampled RV and LV TACs.

In the initialization procedure, the initial sampled RV and LV tissue curves were obtained using equations (92) and (93), and the modified Steiglitz-McBride algorithm was run for $J_1$=20 iterations to get initial estimates for $k_2$ and $k_3$ (see Algorithm 1). Also, $J_2$=500 iterations of the ISRA algorithm were used to determine initial estimates for c and $K_1$ (see Algorithm 2). The IV-MBF algorithm was run for $J_3$=300 iterations and all one-dimensional line searches were performed using a variant of the golden section method. Finally, the penalty parameter was chosen experimentally to be $\lambda$=100.

2. Discussion of FIGS.

Some results for the IV-MBF algorithm are shown in FIGS. 3 and 4. In FIG. 3, the MBF estimates for the $9^{th}$ plane are displayed as an image in FIG. 3A while the corresponding myocardium mask, which specifies the myocardium voxels, is shown in FIG. 3B. Also, the PET image that results from averaging the images for the last six sub-scans and the histogram of the MBF estimates are shown in FIGS. 3C and 3D, respectively. The same information for plane 16 is provided in FIG. 4. Because the data is from a patient the true MBF values are not known. However, Dr. Votaw reviewed the results and considered them to be promising and noted that the range of the MBF estimates was consistent with his expectation and human physiology.

Figure 5A:
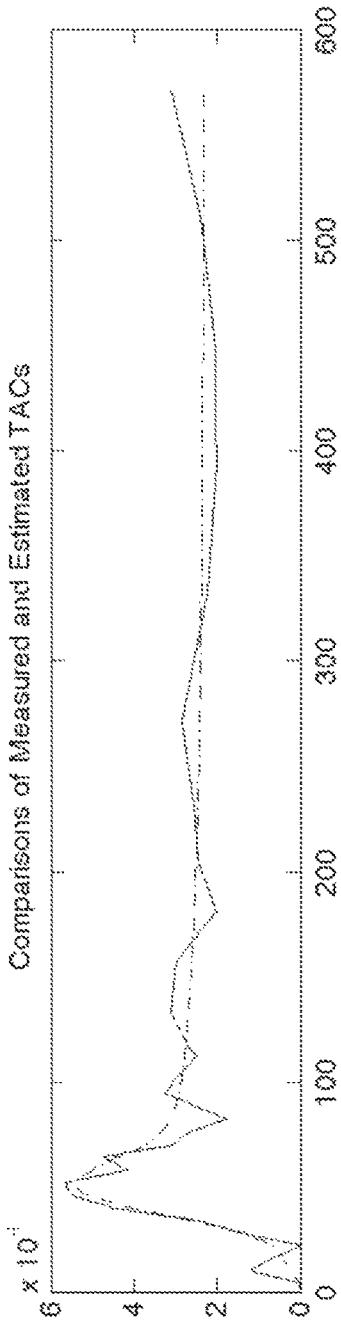
FIG. 5A illustrates a plot of the measured interpolated TAC (solid) and corresponding estimated TAC using the IV-MBF algorithm (dashed-dotted)
Figure 5B:
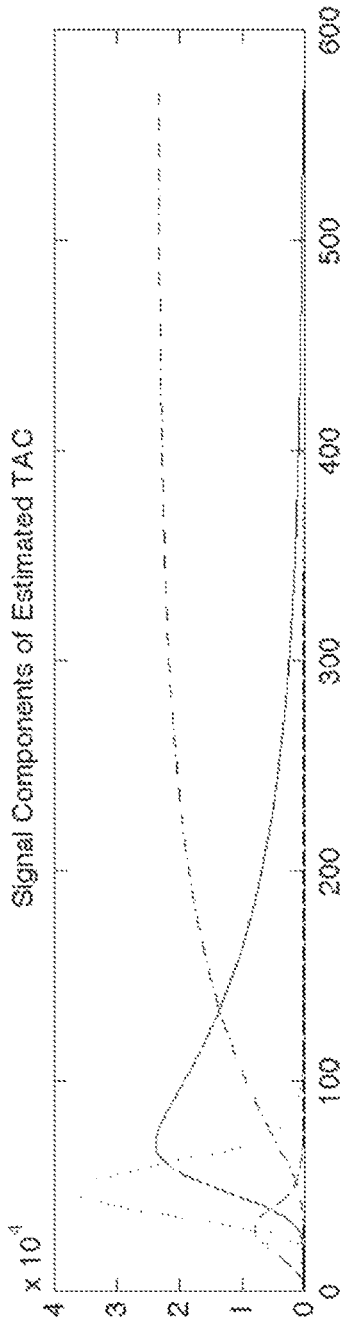
FIG. 5B illustrates signal components that combine to form estimated TAC: sampled RV and LV tissue curves, and curves due to activity in the free and bound states are represented by the dashed, dotted, solid, and dashed-dotted lines, respectively, and 5C illustrates the LS objective function.
Figure 5C:
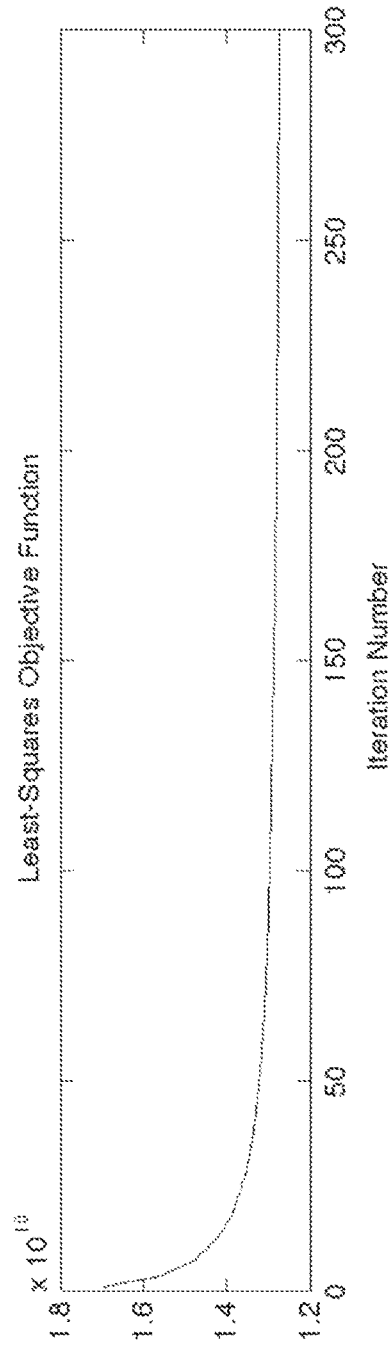
FIG. 5 illustrates example results for a specific myocardium voxel, where

For a specific myocardium voxel, FIG. 5A is a plot of the measured interpolated TAC (solid) and the corresponding estimated TAC using the IV-MBF algorithm (dashed-dotted). Also, the signal components due to activity in the RV (dashed) and LV (dotted), and activity in the free (solid) and trapped (dashed-dotted) states are shown in FIG. 5B. Lastly, a plot of the LS objective function, which decreases monotonically as expected, is shown in FIG. 5C.

G. Proof of Result 1

Let $z_1[n]$, $z_2[n]$, and w[n] be positive, casual sequences of length K. The term $(z_1[n] + z_2[n] * w[n])^2$ can be expressed as $$(z_1[n] + z_2[n]*w[n])^2 = \quad (107)$$
$$\left\{\Delta^{old}[n]\left(\frac{z_1^{old}[n]}{\Delta^{old}[n]}\frac{z_1[n]}{z_1^{old}[n]} + \frac{z_2^{old}[n]*w[n]}{\Delta^{old}[n]}\frac{z_n[n]*w[n]}{z_2^{old}[n]*w[n]}\right)\right\}^2$$

where $\Delta^{old}[n] \triangleq z_1^{old}[n] + z_2^{old}[n]*w[n]$), and $z_1^{old}[n]$ and $z_2^{old}[n]$ are nonnegative, casual sequences. Due to the convex combination on the right hand side of equation (107) and the convexity of the square function, it follows that $$(z_1[n] + z_2[n]*w[n])^2 \leq \quad (108)$$
$$\frac{z_1^{old}[n]}{\Delta^{old}[n]}\left(\frac{z_1[n]\Delta^{(old)}[n]}{z_1^{old}[n]}\right)^2 + \frac{z_2^{old}[n]*w[n]}{\Delta^{old}[n]}\left(\frac{(z_2[n]*w[n])\Delta^{old}[n]}{z_2^{old}[n]*w[n]}\right)^2$$

$$\leq \Delta^{(old)}[n]\left\{\frac{(z_1[n])^2}{z_1^{old}[n]} + \frac{(z_2[n]*w[n])^2}{z_2^{old}[n]*w[n]}\right\} \quad (109)$$

Now, we determine a majorizing function for the sequence $(z_2[n]*w[n])^2$.

The square of the convolution of casual, nonnegative sequences $z_2[n]$ and $w[n]$ can be written as $$(z_2[n]*w[n])^2 = \left(\sum_{k=0}^{K-1} z_2[k]w[n-k]\right)^2 \quad (110)$$

$$= \left\{\sum_{k=0}^{K-1} \gamma_{nk}(z_2^{old}[n]*w[n])\left(\frac{z_2[k]}{z_2^{old}[k]}\right)\right\}^2 \quad (111)$$

where $z^{old}[n]$ is a casual, nonnegative sequence and $$\gamma_{nk} \triangleq \frac{z^{old}[k]w[n-k]}{z^{old}[n]*w[n]} \quad (112)$$

Because $\gamma_{nk} \geq 0$ for all n, k, and $\Sigma_{k=0}^{K} \gamma_{nk}=1$ for all n, the convexity property of the square function can be exploited to yield the desired result $$(z[n]*w[n])^2 \leq \sum_{k=0}^{K-1} \gamma_{nk}\left\{z^{old}[n]*w[n]\left(\frac{z[k]}{z_2^{old}[k]}\right)\right\}^2 \quad (113)$$

$$\leq (z^{old}[n]*w[n])\sum_{k=0}^{K-1} w[n-k]\frac{(z[k])^2}{z_2^{old}[k]} \quad (114)$$

Finally, Result 1 is obtained by replacing $(z[n]*w[n])^2$ in (109) with the majorizing function defined by (114).

VII. Implementation of the Algorithms

Figure 6:
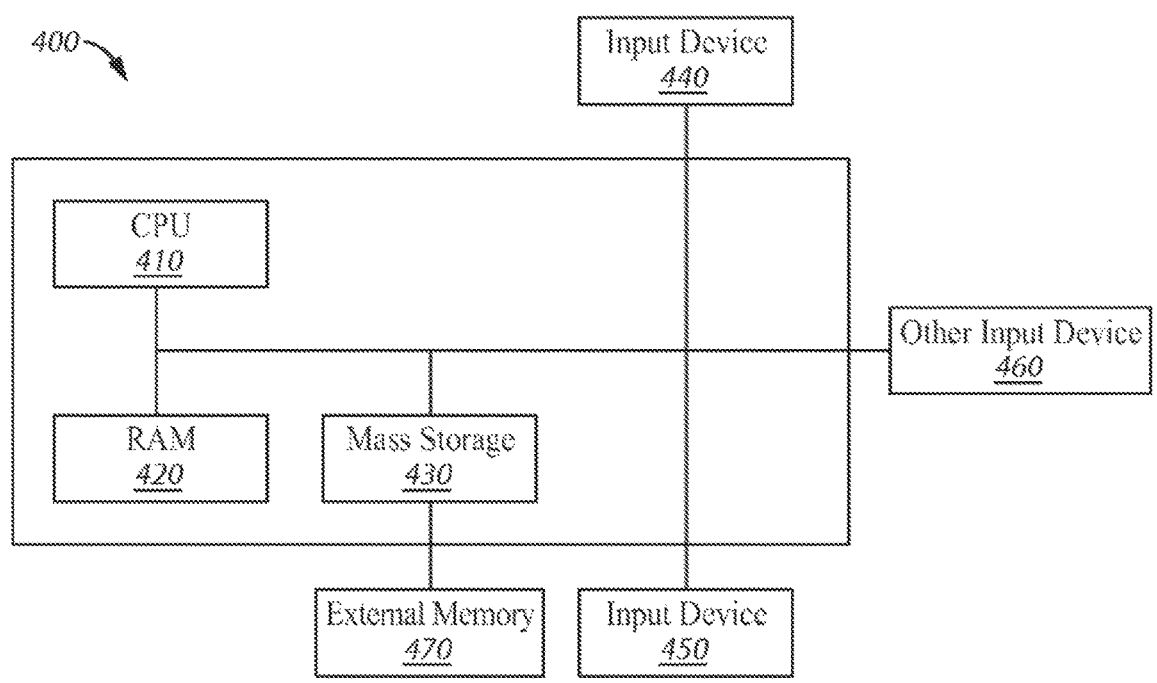
FIG. 6 illustrates an embodiment of a illustrative system that can incorporate the present embodiments.

The methods and techniques described in the various approaches above may be utilized, implemented, and/or run on many different types of systems, including for example computers, game consoles, entertainment systems, etc. Referring to FIG. 6, a system 400 is illustrated that may be used for any such implementations. One or more components of the system 400 may be used for implementing any system or device mentioned above, such as for example even a handheld device. However, the use of the system 400 or any portion thereof is not necessarily required.

By way of example, the system 400 may include, but is not required to include, a central processing unit (CPU) 410, a random access memory (RAM) 420, and a mass storage unit 430, such as a disk drive. The system 400 may be coupled to, or integrated with, any of the other components described herein, such as an input device 450, 460 and other input device 470. The system 400 comprises an example of a processor based system. The CPU 410 may be used to execute or assist in executing the steps of the methods and techniques described herein. In one approach, the system 400 may further comprise a graphics processing unit to execute or assist in executing the steps of the methods and techniques described herein. In some embodiments, the input device 450 may comprise a first touch sensitive panel and the input device 460 may comprise a second touch sensitive panel. Furthermore, in another aspect, the system 400 comprises another input device 460 that may comprise other user input means such as buttons, keyboard, mouse, joystick, and the like. In another aspect, other input device 460 may further comprise output means, such as displays, sound emitters, light emitters, and the like configured to provide feedback or output to a user. In one embodiment one or more of the input device 450, input device 460 and other input device 470 comprise display functionality. In one embodiment various program content, images, shadows, lighting, and the like may be rendered on one or more of the input device 450, 460 and other input device 470.

The mass storage unit 430 may include or comprise any type of computer readable storage or recording medium or media. The computer readable storage or recording medium or media may be fixed in the mass storage unit 430, or the mass storage unit 430 may optionally include external memory 470, such as a digital video disk (DVD). Blu-ray disc, compact disk (CD), USB storage device, floppy disk, or other media. By way of example, the mass storage unit 430 may comprise a disk drive, a hard disk drive, flash memory device, USB storage device, Blu-ray disc drive, DVD drive, CD drive, floppy disk drive, and the like. The mass storage unit 430 or external memory 470 may be used for storing program code or macros that implement the methods and techniques described herein.

Thus, external memory 470 may optionally be used with the mass storage unit 430, which may be used for storing program code that implements the methods and techniques described herein. However, any of the storage devices, such as the RAM 420 or mass storage unit 430, may be used for storing such program code. For example, any of such storage devices may serve as a tangible computer readable storage medium for storing or embodying a computer program for causing a console, system, computer, or other processor based system to execute or perform the steps of any of the methods, code, and/or techniques described herein. Furthermore, any of the storage devices, such as the RAM 420 or mass storage unit 430, may be used for storing any needed database(s), gestures, lists, macros, etc.

In some embodiments, one or more of the embodiments, methods, approaches, and/or techniques described above may be implemented in a computer program executable by a processor based system. By way of example, such processor based system may comprise the processor based system 400, or a computer, console, graphics workstation, and the like. Such computer program may be used for executing various steps and/or features of the above-described methods and/or techniques. That is, the computer program may be adapted to cause or configure a processor based system to execute and achieve the functions described above. For example, such computer program may be used for implementing any embodiment of the above-described steps or techniques for performing a task at the handheld device. As another example, such computer program may be used for implementing any type of tool or similar utility that uses any one or more of the above described embodiments, methods, approaches, and/or techniques. In some embodiments, the computer program may comprise a computer simulation, or system software such as an operating system, BIOS, macro, or other utility. In some embodiments, program code macros, modules, loops, subroutines, etc., within the computer program may be used for executing various steps and/or features of the above-described methods and/or techniques. In some embodiments, the computer program may be stored or embodied on a computer readable storage or recording medium or media, such as any of the computer readable storage or recording medium or media described herein.

Therefore, in some embodiments a computer program product comprising a non-transitory medium for embodying a computer program for input to a computer and a computer program embodied in the medium for causing the computer to perform or execute steps comprising any one or more of the steps involved in any one or more of the embodiments, methods, approaches, and/or techniques described herein.

While the methods and systems have been described in conjunction with specific embodiments, it is evident that many alternatives, modifications, and variations will be apparent to those skilled in the art in light of the foregoing description.

What is claimed is:

1. A method for estimating myocardial blood flow, the method comprising:
   a processing device applying a pharmacological kinetic model to a data set stored in a storage device, the data set derived from an imaging technique based on monitoring fluid based tracers in a left ventricle, a right ventricle, and myocardium, wherein the pharmacological kinetic model includes:
      incorporating a three-compartment kinetic model of changing concentrations of bound fluid based tracers, unbound fluid based tracers, and blood plasma fluid based tracers into a standard factor analysis of dynamic structures model without assumption that a right ventricle tissue curve and a left ventricle tissue curve obey a particular mathematical relationship by discretizing a continuous time model of the changing concentrations of the bound fluid based tracers, the unbound fluid based tracers, and the blood plasma into a discrete time model using non-negative iterate values for the right ventricle tissue curve and the left ventricle tissue curve and non-negative factor weights, and;
   the processing device outputting a processed data set based on the application of the pharmacological kinetic model to the data set for providing a representation of blood flow in the myocardium.

2. The method of claim 1 further comprising the processing device applying a least squares objective function to obtain estimates for parameters of the pharmacological kinetic model.

3. The method of claim 2 further comprising the processing device minimizing the least squares objective function.

4. The method of claim 3 further comprising the processing device minimizing the least squares objective function by applying a majorize-minimize optimization technique to iteratively estimate the right ventricle tissue curve and the left ventricle tissue curve in combination with estimating the blood flow in the myocardium, wherein estimating the blood flow in the myocardium using iteratively updated estimates of the right ventricle tissue curve and the left ventricle tissue curve.

5. The method of claim 1 further comprising the processing device smoothing estimates for blood flow for a given voxel by applying a limiting factor or penalty factor on data from voxels located within a given distance from the given voxel.

6. The method of claim 1 further comprising the processing device determining initial estimates for an initial estimated right ventricle time activity curve and an initial estimated left ventricle time activity curve and using the initial estimates for the initial estimate right ventricle time activity curve and the initial estimated left ventricle time activity curve to determine initial parameters of the pharmacological kinetic model.

7. The method of claim 1 wherein the pharmacological kinetic model includes a semi-parametric model configured to drive time activity curves for the right ventricle imaging activity from the fluid based tracers and the left ventricle imaging activity from the fluid based tracers to zero over time.

8. A non-transitory computer readable medium storing instructions that cause a processing device, in response to executing the instructions, to perform operations comprising:
   the processing device applying a pharmacological kinetic model to a data set stored in a storage device, the data set derived from an imaging technique based on monitoring fluid based tracers in a left ventricle, a right ventricle, and myocardium, wherein the pharmacological kinetic model includes:
      incorporating a three-compartment kinetic model of changing concentrations of bound fluid based tracers, unbound fluid based tracers, and blood plasma fluid based tracers into a standard factor analysis of dynamic structures model without assumption that a right ventricle tissue curve and a left ventricle tissue curve obey a particular mathematical relationship by discretizing a continuous time model of the changing concentrations of the bound fluid based tracers, the unbound fluid based tracers, and the blood plasma into a discrete time model using non-negative iterate values for the right ventricle tissue curve and the left ventricle tissue curve and non-negative factor weights, and;
   the processing device outputting a processed data set based on the application of the pharmacological kinetic model to the data set for providing a representation of blood flow in the myocardium.

9. The non-transitory computer readable medium of claim 8 further comprising instructions to cause the processing device to perform operations comprising applying a least squares objective function to obtain estimates for parameters of the pharmacological kinetic model.

10. The non-transitory computer readable medium of claim 9 further comprising instructions to cause the processing device to perform operations comprising minimizing the least squares objective function.

11. The non-transitory computer readable medium of claim 10 further comprising instructions to cause the processing device to perform operations comprising minimizing the least squares objective function by applying a majorize-minimize optimization technique to iteratively estimate the right ventricle tissue curve and the left ventricle tissue curve in combination with estimating the blood flow in the myocardium, wherein estimating the blood flow in the myocardium using iteratively updated estimates of the right ventricle tissue curve and the left ventricle tissue curve.

12. The non-transitory computer readable medium of claim 8 further comprising instructions to cause the processing device to perform operations comprising smoothing estimates for blood flow for a given voxel by applying a limiting factor or penalty factor on data from voxels located within a given distance from the given voxel.

13. The non-transitory computer readable medium of claim 8 further comprising instructions to cause the processing device to perform operations comprising determining initial estimates for an initial estimated right ventricle time activity curve and an initial estimated left ventricle time activity curve and using the initial estimates for the initial estimate right ventricle time activity curve and the initial estimated left ventricle time activity curve to determine initial parameters of the pharmacological kinetic model.

14. The non-transitory computer readable medium of claim 8 wherein the pharmacological kinetic model includes a semi-parametric model configured to drive time activity curves for the right ventricle imaging activity from the fluid based tracers and the left ventricle imaging activity from the fluid based tracers to zero over time.

15. An apparatus comprising:
 a processing device configured to apply a pharmacological kinetic model to a data set stored in a storage device, the data set derived from an imaging technique based on monitoring fluid based tracers in a left ventricle, a right ventricle, and myocardium, wherein the pharmacological kinetic model includes:
  incorporating a three-compartment kinetic model of changing concentrations of bound fluid based tracers, unbound fluid based tracers, and blood plasma fluid based tracers into a standard factor analysis of dynamic structures model without assumption that a right ventricle tissue curve and a left ventricle tissue curve obey a particular mathematical relationship by discretizing a continuous time model of the changing concentrations of the bound fluid based tracers, the unbound fluid based tracers, and the blood plasma into a discrete time model using non-negative iterate values for the right ventricle tissue curve and the left ventricle tissue curve and non-negative factor weights, and;
 the processing device configured to output a processed data set based on the application of the pharmacological kinetic model to the data set for providing a representation of blood flow in the myocardium.

16. The apparatus of claim 15 wherein the processing device is configured to apply a least squares objective function to obtain estimates for parameters of the pharmacological kinetic model.

17. The apparatus of claim 16 wherein the processing device is configured to minimize the least squares objective function by applying a majorize-minimize optimization technique to iteratively estimate the right ventricle tissue curve and the left ventricle tissue curve in combination with estimating the blood flow in the myocardium, wherein estimating the blood flow in the myocardium using iteratively updated estimates of the right ventricle tissue curve and the left ventricle tissue curve.

18. The apparatus of claim 15 wherein the processing device is configured to smooth estimates for blood flow for a given voxel by applying a limiting factor or penalty factor on data from voxels located within a given distance from the given voxel.

19. The apparatus of claim 15 wherein the processing device is further configured to determine initial estimates for an initial estimated right ventricle time activity curve and an initial estimated left ventricle time activity curve and to use the initial estimates for the initial estimate right ventricle time activity curve and the initial estimated left ventricle time activity curve to determine initial parameters of the pharmacological kinetic model.

20. The apparatus of claim 15 wherein the pharmacological kinetic model includes a semi-parametric model configured to drive time activity curves for the right ventricle imaging activity from the fluid based tracers and the left ventricle imaging activity from the fluid based tracers to zero over time.

\* \* \* \* \*